United States Patent
Von Coburg et al.

(10) Patent No.: US 10,071,089 B2
(45) Date of Patent: Sep. 11, 2018

(54) COMBINATION OF OXYCODONE AND NALOXONE FOR USE IN TREATING PAIN IN PATIENTS SUFFERING FROM PAIN AND A DISEASE RESULTING IN INTESTINAL DYSBIOSIS AND/OR INCREASING THE RISK FOR INTESTINAL BACTERIAL TRANSLOCATION

(71) Applicant: Euro-Celtique S.A., Luxembourg (LU)

(72) Inventors: Yvonne Von Coburg, Limburg (DE);
Karen Reimer, Limburg (DE);
Alexander Oksche, Limburg (DE);
Peter Holzer, Graz (AT)

(73) Assignee: Euro-Celtique S.A., Luxembourg (LU)

( * ) Notice: Subject to any disclaimer, the term of this patent is extended or adjusted under 35 U.S.C. 154(b) by 0 days.

(21) Appl. No.: 14/907,265

(22) PCT Filed: Jul. 23, 2014

(86) PCT No.: PCT/EP2014/065816
§ 371 (c)(1),
(2) Date: Jan. 22, 2016

(87) PCT Pub. No.: WO2015/011189
PCT Pub. Date: Jan. 29, 2015

(65) Prior Publication Data
US 2016/0184293 A1    Jun. 30, 2016

(30) Foreign Application Priority Data
Jul. 23, 2013 (EP) .................................... 13177646

(51) Int. Cl.
*A61K 31/485* (2006.01)
*A61K 9/20* (2006.01)
*A61K 9/48* (2006.01)

(52) U.S. Cl.
CPC .......... *A61K 31/485* (2013.01); *A61K 9/2054* (2013.01); *A61K 9/4866* (2013.01)

(58) Field of Classification Search
None
See application file for complete search history.

(56) References Cited

U.S. PATENT DOCUMENTS

| | | |
|---|---|---|
| 2,770,569 A | 11/1956 | Fromherz et al. |
| 3,133,132 A | 5/1964 | Loeb et al. |
| 3,173,876 A | 3/1965 | Zobrist |
| 3,173,877 A | 3/1965 | Jackson et al. |
| 3,276,586 A | 10/1966 | Rosaen |
| 3,332,950 A | 7/1967 | Blumberg et al. |
| 3,493,657 A | 2/1970 | Lewenstein et al. |
| 3,541,005 A | 11/1970 | Strathmann et al. |
| 3,541,006 A | 11/1970 | Bixler et al. |
| 3,546,876 A | 12/1970 | Fokker et al. |
| 3,676,557 A | 7/1972 | Lachman et al. |
| 3,773,955 A | 11/1973 | Pachter et al. |
| 3,845,770 A | 11/1974 | Theeuwes et al. |
| 3,879,555 A | 4/1975 | Pachter et al. |
| 3,916,889 A | 11/1975 | Russell |
| 3,916,899 A | 11/1975 | Theeuwes et al. |
| 3,950,508 A | 4/1976 | Mony et al. |
| 3,965,256 A | 6/1976 | Leslie |
| 3,966,940 A | 6/1976 | Patcher |
| 4,063,064 A | 12/1977 | Saunders et al. |
| 4,088,864 A | 5/1978 | Theeuwes et al. |
| 4,126,684 A | 11/1978 | Robson et al. |
| 4,160,020 A | 7/1979 | Ayer et al. |
| 4,176,186 A | 11/1979 | Goldberg |
| 4,200,098 A | 4/1980 | Ayer et al. |
| 4,216,314 A | 8/1980 | Raabe et al. |
| 4,237,140 A | 12/1980 | Dudzinski |
| 4,285,987 A | 8/1981 | Ayer et al. |
| 4,293,539 A | 10/1981 | Ludwig et al. |
| 4,366,310 A | 12/1982 | Leslie |
| 4,401,672 A | 8/1983 | Portoghese et al. |
| 4,443,428 A | 4/1984 | Oshlack et al. |
| 4,451,470 A | 5/1984 | Ganti |

(Continued)

FOREIGN PATENT DOCUMENTS

| | | |
|---|---|---|
| AU | 2002305559 | 11/2002 |
| CA | 2382648 | 3/2001 |

(Continued)

OTHER PUBLICATIONS

Abdulla et al., "Axotomy reduces the effect of analgesic opioids yet increases the effect of nociceptin on dorsal root ganglion neurons"; J of Neuro Sci (1998) vol. 18, pp. 9685-9694.
Abernethy et al., "Randomised, double blind, placebo controlled crossover trial of sustained release morphine for the management of refractory dyspnoea," BMJ, vol. 327, pp. 1-6 (2003).
Alvarez-Fuentes et al. "Effectiveness of Repeated Administration of a New Oral Naltrexone Controlled-Release System in Morphine Analgesia"; J. Pharm Pharmacol (2001), 53:1201-1205.
Alvarez-Fuentes, et al., "Preclinical Study of an Oral Controlled Release Naltrexone Complex in Mice"; J. Pharm Pharmacol (2000), 52:659-663.
Amass et al., "Efficacy of daily and alternate-day dosing regimens with the combination buprenorphine-naloxone tablet"; Drug and Alcohol Dependence (2000) vol. 58, pp. 143-152.

(Continued)

*Primary Examiner* — Jessica N Worsham
(74) *Attorney, Agent, or Firm* — Dechert LLP; Carl A. Morales; Blaine M. Hackman

(57) ABSTRACT

The present invention is concerned with an oral pharmaceutical dosage form comprising oxycodone or a pharmaceutically acceptable salt thereof and naloxone or a pharmaceutically acceptable salt thereof for use in the treatment of pain in patients suffering from i) pain and at least one further disease ii), wherein said at least one further disease ii) results in intestinal dysbiosis, or for use in the treatment of pain in patients suffering from i) pain and at least one further disease iii), wherein said at least one further disease iii) increases the risk for intestinal bacterial translocation and thus for peritonitis, SIRS and/or sepsis.

21 Claims, 13 Drawing Sheets

(56) References Cited

U.S. PATENT DOCUMENTS

| | | |
|---|---|---|
| 4,457,933 A | 7/1984 | Gordon |
| 4,464,378 A | 8/1984 | Hussain et al. |
| 4,573,995 A | 3/1986 | Chen et al. |
| 4,582,835 A | 4/1986 | Lewis et al. |
| 4,608,376 A | 8/1986 | Pasternak |
| 4,661,492 A | 4/1987 | Lewis et al. |
| 4,668,685 A | 5/1987 | Shami |
| 4,719,215 A | 1/1988 | Goldberg |
| 4,722,928 A | 2/1988 | Boswell et al. |
| 4,730,048 A | 3/1988 | Portoghese et al. |
| 4,760,069 A | 7/1988 | Rzeszotarski et al. |
| 4,769,372 A | 9/1988 | Kreek |
| 4,785,000 A | 11/1988 | Kreek et al. |
| 4,803,208 A | 2/1989 | Pasternak |
| 4,806,341 A | 2/1989 | Chien et al. |
| 4,806,543 A | 2/1989 | Choi |
| 4,806,558 A | 2/1989 | Wuest et al. |
| 4,828,836 A | 5/1989 | Elger et al. |
| 4,834,965 A | 5/1989 | Martani et al. |
| 4,834,984 A | 5/1989 | Goldie et al. |
| 4,834,985 A | 5/1989 | Elger et al. |
| 4,844,907 A | 7/1989 | Elger et al. |
| 4,844,909 A | 7/1989 | Goldie et al. |
| 4,844,910 A | 7/1989 | Leslie et al. |
| 4,861,598 A | 8/1989 | Oshlack |
| 4,861,781 A | 8/1989 | Goldberg |
| 4,867,985 A | 9/1989 | Heafield et al. |
| 4,873,076 A | 10/1989 | Fishman et al. |
| 4,882,335 A | 11/1989 | Sinclair |
| 4,889,860 A | 12/1989 | Rzeszotarski et al. |
| 4,935,428 A | 6/1990 | Lewis |
| 4,940,587 A | 7/1990 | Jenkins et al. |
| 4,957,681 A | 9/1990 | Klimesch et al. |
| 4,970,075 A | 11/1990 | Oshlak |
| 4,987,136 A | 1/1991 | Kreek et al. |
| 4,990,341 A | 2/1991 | Goldie et al. |
| 5,071,646 A | 12/1991 | Malkowska et al. |
| 5,075,341 A | 12/1991 | Mendelson et al. |
| 5,086,058 A | 2/1992 | Sinclair et al. |
| 5,091,189 A | 2/1992 | Heafield et al. |
| 5,096,715 A | 3/1992 | Sinclair |
| 5,102,887 A | 4/1992 | Goldberg |
| 5,130,311 A | 7/1992 | Guillaumet et al. |
| 5,149,538 A | 9/1992 | Granger et al. |
| 5,215,758 A | 6/1993 | Krishnamurthy |
| 5,225,440 A | 7/1993 | London et al. |
| 5,236,714 A | 8/1993 | Lee et al. |
| 5,256,669 A | 10/1993 | Askanazi et al. |
| 5,266,331 A | 11/1993 | Oshlack et al. |
| 5,273,760 A | 12/1993 | Oshlack et al. |
| 5,286,493 A | 2/1994 | Oshlack et al. |
| 5,316,759 A | 5/1994 | Rose et al. |
| 5,317,022 A | 5/1994 | Borsodi et al. |
| 5,321,012 A | 6/1994 | Mayer et al. |
| 5,324,351 A | 6/1994 | Oshlack et al. |
| 5,336,691 A | 8/1994 | Raffa et al. |
| 5,352,680 A | 10/1994 | Portoghese et al. |
| 5,352,683 A | 10/1994 | Mayer et al. |
| 5,356,467 A | 10/1994 | Oshlack et al. |
| 5,356,900 A | 10/1994 | Bihari et al. |
| 5,376,662 A | 12/1994 | Ockert |
| 5,409,944 A | 4/1995 | Black et al. |
| 5,411,745 A | 5/1995 | Oshlack et al. |
| 5,426,112 A | 6/1995 | Zagon et al. |
| 5,436,265 A | 7/1995 | Black et al. |
| 5,457,208 A | 10/1995 | Portoghese et al. |
| 5,460,826 A | 10/1995 | Merrill et al. |
| 5,472,712 A | 12/1995 | Oshlack et al. |
| 5,472,943 A | 12/1995 | Crain |
| 5,474,995 A | 12/1995 | Ducharme et al. |
| 5,478,577 A | 12/1995 | Sackler et al. |
| 5,486,362 A | 1/1996 | Kitchell et al. |
| 5,500,227 A | 3/1996 | Oshlack et al. |
| 5,502,058 A | 3/1996 | Mayer et al. |
| 5,508,042 A | 4/1996 | Oshlack et al. |
| 5,508,043 A | 4/1996 | Krishnamurthy |
| 5,510,368 A | 4/1996 | Lau et al. |
| 5,512,578 A | 4/1996 | Crain |
| 5,514,680 A | 5/1996 | Weber et al. |
| 5,521,213 A | 5/1996 | Prasit et al. |
| 5,534,492 A | 7/1996 | Aston et al. |
| 5,536,752 A | 7/1996 | Ducharme et al. |
| 5,549,912 A | 8/1996 | Oshlack et al. |
| 5,550,142 A | 8/1996 | Ducharme et al. |
| 5,552,422 A | 9/1996 | Gauthier et al. |
| 5,556,838 A | 9/1996 | Mayer et al. |
| 5,574,052 A | 11/1996 | Rose et al. |
| 5,578,725 A | 11/1996 | Portoghese et al. |
| 5,580,578 A | 12/1996 | Oshlack et al. |
| 5,580,876 A | 12/1996 | Crain |
| 5,585,348 A | 12/1996 | Crain et al. |
| 5,591,452 A | 1/1997 | Miller et al. |
| 5,592,310 A | 1/1997 | Sugiura |
| 5,593,994 A | 1/1997 | Batt et al. |
| 5,601,845 A | 2/1997 | Buxton et al. |
| 5,604,253 A | 2/1997 | Lau et al. |
| 5,604,260 A | 2/1997 | Guay et al. |
| 5,616,601 A | 4/1997 | Khanna et al. |
| 5,622,722 A | 4/1997 | Knott et al. |
| 5,624,932 A | 4/1997 | Qin et al. |
| 5,633,259 A | 5/1997 | Qin et al. |
| 5,639,476 A | 6/1997 | Oshlack et al. |
| 5,639,780 A | 6/1997 | Lau et al. |
| 5,656,295 A | 8/1997 | Oshlack et al. |
| 5,670,172 A | 9/1997 | Buxton et al. |
| 5,672,360 A | 9/1997 | Sackler et al. |
| 5,681,585 A | 10/1997 | Oshlack et al. |
| 5,692,500 A | 12/1997 | Gaston-Johansson |
| 5,763,452 A | 6/1998 | Miller et al. |
| 5,767,125 A | 6/1998 | Crain |
| 5,780,479 A | 7/1998 | Kim |
| 5,811,126 A | 9/1998 | Krishnamurthy |
| 5,834,477 A | 11/1998 | Mioduszewski |
| 5,843,480 A | 12/1998 | Miller et al. |
| 5,849,240 A | 12/1998 | Miller et al. |
| 5,858,017 A | 1/1999 | Demopulos et al. |
| 5,860,950 A | 1/1999 | Demopulos et al. |
| 5,866,154 A | 2/1999 | Bahal et al. |
| 5,866,164 A | 2/1999 | Kuczynski et al. |
| 5,869,097 A | 2/1999 | Wong et al. |
| 5,879,705 A | 3/1999 | Heafield et al. |
| 5,880,132 A | 3/1999 | Hill |
| 5,891,471 A | 4/1999 | Miller et al. |
| 5,908,848 A | 6/1999 | Miller et al. |
| 5,942,241 A | 8/1999 | Chasin et al. |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,547 A | 10/1999 | Reder et al. |
| 5,968,551 A | 10/1999 | Oshlack et al. |
| 5,972,310 A | 10/1999 | Sachetto |
| 5,972,954 A | 10/1999 | Foss |
| 5,998,434 A | 12/1999 | Mitch et al. |
| 6,024,982 A | 2/2000 | Oshlack et al. |
| 6,068,855 A | 5/2000 | Leslie et al. |
| 6,077,532 A | 6/2000 | Malkowska et al. |
| 6,077,533 A | 6/2000 | Oshlack et al. |
| 6,096,756 A | 8/2000 | Crain et al. |
| 6,103,258 A | 8/2000 | Simon |
| 6,103,261 A | 8/2000 | Chasin et al. |
| 6,114,326 A | 9/2000 | Schueler |
| 6,143,322 A | 11/2000 | Sackler et al. |
| 6,143,328 A | 11/2000 | Heafield et al. |
| 6,159,501 A | 12/2000 | Skinhoj |
| 6,162,467 A | 12/2000 | Miller et al. |
| 6,194,382 B1 | 2/2001 | Crain et al. |
| 6,207,142 B1 | 3/2001 | Odds et al. |
| 6,210,714 B1 | 4/2001 | Oshlack et al. |
| 6,228,863 B1 | 5/2001 | Palermo |
| 6,254,887 B1 | 7/2001 | Miller et al. |
| 6,258,042 B1 | 7/2001 | Factor et al. |
| 6,261,599 B1 | 7/2001 | Oshlack et al. |
| 6,277,384 B1 | 8/2001 | Kaiko |

(56) References Cited

U.S. PATENT DOCUMENTS

| | | |
|---|---|---|
| 6,294,195 B1 | 9/2001 | Oshlack et al. |
| 6,306,438 B1 | 10/2001 | Oshlack et al. |
| 6,310,072 B1 | 10/2001 | Smith et al. |
| 6,326,027 B1 | 12/2001 | Miller et al. |
| 6,335,033 B2 | 1/2002 | Oshlack et al. |
| 6,362,194 B1 | 3/2002 | Crain et al. |
| 6,375,957 B1 | 4/2002 | Kaiko et al. |
| 6,387,404 B2 | 5/2002 | Oshlack |
| 6,395,705 B2 | 5/2002 | Crain et al. |
| 6,399,096 B1 | 6/2002 | Miller et al. |
| 6,419,959 B1 | 7/2002 | Walter et al. |
| 6,451,806 B2 | 9/2002 | Farrar |
| 6,475,494 B2 | 11/2002 | Kaiko et al. |
| 6,579,536 B1 | 6/2003 | Hirsch et al. |
| 6,596,900 B2 | 7/2003 | Blakemore et al. |
| 6,602,868 B2 | 8/2003 | McBrinn et al. |
| 6,627,635 B2 | 9/2003 | Palermo et al. |
| 6,696,066 B2 | 2/2004 | Kaiko et al. |
| 6,696,088 B2 | 2/2004 | Oshlack et al. |
| 6,706,281 B2 | 3/2004 | Oshlack et al. |
| 6,716,449 B2 | 4/2004 | Oshlack et al. |
| 6,743,442 B2 | 6/2004 | Oshlack |
| 6,765,010 B2 | 7/2004 | Crain et al. |
| 7,172,767 B2 | 2/2007 | Kaiko et al. |
| 7,332,182 B2 | 2/2008 | Sackler |
| 7,419,686 B2 | 9/2008 | Kaiko et al. |
| 7,749,542 B2 | 7/2010 | Kaiko et al. |
| 8,105,631 B2 | 1/2012 | Kaiko et al. |
| 8,673,355 B2 | 3/2014 | Kaiko et al. |
| 8,822,487 B2 | 9/2014 | Kaiko et al. |
| 8,846,090 B2 | 9/2014 | Brögmann et al. |
| 8,846,091 B2 | 9/2014 | Brögmann et al. |
| 2001/0006967 A1 | 7/2001 | Crain et al. |
| 2001/0018413 A1 | 8/2001 | Crain et al. |
| 2001/0053777 A1 | 12/2001 | Brecht |
| 2002/0006964 A1 | 1/2002 | Young et al. |
| 2002/0010127 A1 | 1/2002 | Oshlack et al. |
| 2002/0031552 A1 | 3/2002 | McTeigue et al. |
| 2002/0058673 A1 | 5/2002 | Kaiko et al. |
| 2003/0004177 A1 | 1/2003 | Kao |
| 2003/0044458 A1 | 3/2003 | Wright, IV et al. |
| 2003/0065002 A1 | 4/2003 | Caruso et al. |
| 2003/0069263 A1 | 4/2003 | Breder et al. |
| 2003/0073714 A1 | 4/2003 | Breder et al. |
| 2003/0092759 A1 | 5/2003 | Abuzzahab, Sr. |
| 2003/0118641 A1 | 6/2003 | Maloney et al. |
| 2003/0143269 A1 | 7/2003 | Oshlack |
| 2003/0178031 A1 | 9/2003 | DuPen et al. |
| 2003/0191147 A1 | 10/2003 | Sherman et al. |
| 2003/0229111 A1 | 12/2003 | Oshlack et al. |
| 2004/0052731 A1 | 3/2004 | Hirsh et al. |
| 2004/0092542 A1 | 5/2004 | Oshlack et al. |
| 2004/0176402 A1 | 9/2004 | Oshlack et al. |
| 2004/0186121 A1 | 9/2004 | Oshlack et al. |
| 2005/0063909 A1 | 3/2005 | Wright et al. |
| 2005/0095291 A1 | 5/2005 | Oshlack et al. |
| 2005/0163856 A1 | 7/2005 | Maloney et al. |
| 2005/0181046 A1 | 8/2005 | Oshlack et al. |
| 2005/0245483 A1 | 11/2005 | Brogmann et al. |
| 2005/0245556 A1 | 11/2005 | Brogmann et al. |
| 2005/0272776 A1 | 12/2005 | Buehler |
| 2006/0039970 A1 | 2/2006 | Oshlack et al. |
| 2006/0182801 A1 | 8/2006 | Breder et al. |
| 2007/0122348 A1 | 5/2007 | Kaiko et al. |
| 2007/0185146 A1 | 8/2007 | Fleischer et al. |
| 2008/0145429 A1 | 6/2008 | Leyendecker et al. |
| 2009/0192157 A1* | 7/2009 | Maddaford ......... A61K 31/404 514/235.2 |
| 2011/0142939 A1 | 6/2011 | Bennette-Kerr et al. |
| 2011/0172259 A1 | 7/2011 | Leyendecker et al. |
| 2012/0108621 A1 | 5/2012 | Brögmann et al. |
| 2012/0165359 A1 | 6/2012 | Kaiko et al. |
| 2012/0183612 A1 | 7/2012 | Brögmann et al. |
| 2012/0225901 A1 | 9/2012 | Leyendecker et al. |
| 2013/0165418 A1 | 6/2013 | Kaiko et al. |

FOREIGN PATENT DOCUMENTS

| | | |
|---|---|---|
| CA | 2478515 | 10/2003 |
| CA | 2478523 | 10/2003 |
| CA | 2372025 | 9/2007 |
| DE | 4325465 | 2/1995 |
| EP | 0193355 | 9/1986 |
| EP | 0205282 | 12/1986 |
| EP | 0319243 | 6/1989 |
| EP | 352361 | 1/1990 |
| EP | 527638 | 2/1993 |
| EP | 0576643 | 6/1993 |
| EP | 624366 | 11/1994 |
| EP | 631781 | 1/1995 |
| EP | 0647448 | 4/1995 |
| EP | 699436 | 3/1996 |
| EP | 0880352 | 2/1998 |
| EP | 0913152 | 5/1999 |
| EP | 1604666 | 12/2000 |
| EP | 1201233 | 5/2002 |
| EP | 1348429 | 10/2003 |
| EP | 1364649 | 11/2003 |
| EP | 1041987 B1 | 4/2006 |
| EP | 1695700 | 8/2006 |
| EP | 1813276 | 8/2007 |
| GB | 1353815 | 5/1974 |
| GB | 139072 A1 | 4/1975 |
| JP | H10-251149 | 9/1998 |
| NZ | 260408 | 5/1996 |
| NZ | 264953 | 11/1996 |
| NZ | 260883 | 6/1997 |
| NZ | 294897 | 10/1998 |
| NZ | 544181 | 12/2008 |
| RU | 98102450 | 7/1996 |
| RU | 2222260 | 1/2004 |
| WO | WO1983/03197 | 9/1983 |
| WO | WO1987/01282 | 3/1987 |
| WO | WO1990/04965 | 5/1990 |
| WO | WO1993/010765 | 6/1993 |
| WO | WO1994/06426 | 3/1994 |
| WO | WO1995/03804 | 2/1995 |
| WO | WO1996/02251 | 2/1996 |
| WO | WO1996/014058 | 5/1996 |
| WO | WO1996/014059 | 5/1996 |
| WO | WO1997/33566 | 9/1997 |
| WO | WO1997/045091 | 12/1997 |
| WO | WO1998/025613 | 6/1998 |
| WO | WO1998/35679 | 8/1998 |
| WO | WO1999/001111 | 1/1999 |
| WO | WO1999/005960 | 2/1999 |
| WO | WO1999/11250 A2 | 3/1999 |
| WO | WO1999/022737 | 5/1999 |
| WO | WO1999/32119 A1 | 7/1999 |
| WO | WO1999/32120 A1 | 7/1999 |
| WO | WO2000/01377 | 1/2000 |
| WO | WO2000/025821 | 5/2000 |
| WO | WO2000/38649 | 7/2000 |
| WO | WO2000/41683 | 7/2000 |
| WO | WO2000/051592 | 9/2000 |
| WO | WO2000/067739 | 11/2000 |
| WO | WO2001/032180 | 5/2001 |
| WO | WO2001/37785 | 5/2001 |
| WO | WO2001/52851 | 7/2001 |
| WO | WO2001/58447 A1 | 8/2001 |
| WO | WO2001/58451 A1 | 8/2001 |
| WO | WO2001/68080 | 9/2001 |
| WO | WO2001/85150 | 11/2001 |
| WO | WO2001/85257 | 11/2001 |
| WO | WO2001/93852 | 12/2001 |
| WO | WO2002/087512 | 11/2002 |
| WO | WO2002/092059 | 11/2002 |
| WO | WO2002/092060 | 11/2002 |
| WO | WO2003/003541 | 1/2003 |
| WO | WO2003/004009 | 1/2003 |
| WO | WO2003/007802 | 1/2003 |
| WO | WO2003/013476 | 2/2003 |
| WO | WO2003/013479 | 2/2003 |
| WO | WO2003/013538 | 2/2003 |
| WO | WO2003/020124 | 3/2003 |

(56) References Cited

FOREIGN PATENT DOCUMENTS

| WO | WO2003/024429 | 3/2003 |
|---|---|---|
| WO | WO2003/024430 | 3/2003 |
| WO | WO2003/026676 | 4/2003 |
| WO | WO2003/070191 | 8/2003 |
| WO | WO2003/073937 | 9/2003 |
| WO | WO2003/084504 | 10/2003 |
| WO | WO-2003084520 A2 | 10/2003 |
| WO | WO2004/026262 | 4/2004 |
| WO | WO2004/064807 | 8/2004 |
| WO | WO2004/091623 | 10/2004 |
| WO | WO2005/000310 | 1/2005 |
| WO | WO2005/025621 | 3/2005 |
| WO | WO2005/079760 | 9/2005 |
| WO | WO2005/120506 | 12/2005 |
| WO | WO2005/120507 | 12/2005 |
| WO | WO2006/024881 | 3/2006 |
| WO | WO2006/079550 | 8/2006 |
| WO | WO2006/089970 | 8/2006 |
| WO | WO2006/089973 | 8/2006 |
| WO | WO2007/047935 | 4/2007 |
| WO | WO2007/085637 | 8/2007 |
| WO | WO2007/088489 | 8/2007 |
| WO | WO2007/111945 | 10/2007 |
| WO | WO2007/123865 | 11/2007 |
| WO | WO2008/025790 | 3/2008 |
| WO | WO2008/030567 | 3/2008 |
| WO | WO2009/040394 | 4/2009 |
| WO | WO2010/003963 | 1/2010 |
| WO | WO2010/103039 | 9/2010 |
| WO | WO2012/020097 | 2/2012 |
| WO | WO2012/089738 | 7/2012 |

OTHER PUBLICATIONS

Amati et al., "In vitro effects of naloxone on T-lymphocyte-dependent antibacterial activity in hepatitis C virus (HCV) infected patients and in inflammatory bowel disease (IBD) patient," Immunopharmacology and Immunotoxicology, vol. 23, No. 1, pp. 1-11 (2001).
U.S. Appl. No. 10/143,111, Final Office Action dated Apr. 25, 2006.
U.S. Appl. No. 10/143,111, Final Office Action dated Nov. 8, 2004.
U.S. Appl. No. 10/143,111, Non Final Office Action dated Jan. 29, 2007.
U.S. Appl. No. 10/143,111, Non Final Office Action dated Sep. 30, 2005.
U.S. Appl. No. 10/143,111, Non Final Office Action dated Jan. 28, 2004.
U.S. Appl. No. 11/901,232, Final Office Action dated Dec. 16, 2011.
U.S. Appl. No. 11/901,232, Non Final Office Action dated Jul. 15, 2011.
Archer Sydney; "Historical Perspective on the Chemistry and Development of Naltrexone"; Naltrexone Research Monograph 28 (1980) p. 3-9.
Azamari et al., "Thermal treating as a tool for sustained release of indomethacin from Eudragit RS and RL matrices," International Journal of Pharmaceutics, 246, 171-177 (2002).
Barton et al., "Intranasal Administration of Naloxone by Paramedics";Prehospital Emergency Care (2002) vol. 6, No. 1, pp. 54-58.
Bashaw et al., "Relative bioavailability of controlled-release oral morphine sulfate during naltrexone blockade"; Inter J of Clin Pharm and Thea (1995) vol. 33, No. 9, pp. 524-529.
Baum et al., "The Impact of the Addition of Naloxone on the Use and Abuse of Pentazocine"; Public Health Reports (1987) vol. 102, No. 4 p. 426-429.
Beauford et al., "Effects of Nebulized Morphine Sulfate on the Exercise Tolerance Ventilatory Limited COPD Patient," Chest, vol. 104, No. 1, pp. 175-178 (1993).
Benfey "Function of Myocardial-Adrenoceptors" ; Life Sciences (1982) vol. 31, pp. 101-112.

Benziger et al., "Differential effects of food on the bioavailability of cr oxycodone tablets and it oxycodone solution" J. Pharm. Sciences, vol. 85, No. 4, pp. 407-410 (1996).
Berkow, R. (ed.) Merck Manual of Medical Information, pp. 528-530 (1997).
Berkow, R. (ed.) The Merck Manual of Diagnosis and Therapy (1997), extract (English Translation from Russian).
Bigelow et al., "Abuse Liability and Assessment of Buprenorphine-Naloxone Combinations"; Dept of Psychiatry and Behavioral Sciences, The Johns Hopkins University School of Medicine, pp. 145-149, (1987).
Blachly Paul, H., M.D., "Naloxone in Opiate Addiction"; Current Psychiatric Therapies (1976) pp. 209-213.
Bloom et al., "Clinical Studies with Naloxone/Methadone in a Ratio of 1:20"; 5th National Conference on Methadone Treatment (1973) vol. 2, p. 1342-1349.
Brennscheidt et al., "Pharmacokinetics of Nortilidine and Naloxone after Administration of Tilidine/Naloxone Solution or Tilidine/Naloxone Sustained Release Tablets"; Arzeim-Forsch/Drug Res. (2000) vol. 50, pp. 1015-1022.
Briscoe et al., "Methoclocinnamox: Time Course of Changes in Alfetnanil-Reinforced Rhesus Monkeys"; Psychopharmacology (2000) 148:393-399.
Bromim et al., "A Sensitive Method to Evaluate Effects of Analgesics in Man"; Meth and Find Exptl Clin Pharmacol 5 (8) (1983) p. 545-551 (abstract).
Budd, Keith, "Clinical Use of Opioid Antagonists"; Bailliere's Clinical Anesthesiology (1987) vol. 1, No. 4, pp. 993-1011.
Bullingham et al., "Clinical Pharmacokinetics of Narcotic Agonist-Antagonist Drugs"; Clinical Pharm (1983) 8: 332-343.
Bunzow et al., "Molecular cloning and tissue distribution of a putative member of the rat opioid receptor gene family that is not a mu, delta or kappa opioid receptor type." FEBS Lett. Jun. 27, 1994;347 (2-3):284-8.
Bures et al., "Small intestinal bacteria overgrowth syndrome," World J. Gastroenterol, vol. 16, No. 24, pp. 2978-2990 (2010).
Caldwell et al., "Treatment of Osteoarthritis Pain with Controlled Release Oxycodone or Fixed Combination Oxycodone Plus Acetaminophen Added to Nonsteroidal Antiinflammatory Drugs: A Double Blind, Randomized, Multicenter, Placebo Controlled Trial,"J. Rheumatol. vol. 26, No. 4, pp. 862-869 (1999).
Calimlim, et al. "Effect of Naloxone on the Analgesic Activity of Methadone in a 1:10 Oral Combination"; Clin Pharmacol and Ther. (1974) vol. 15; No. 6, pp. 556-564.
Cappel et al., "Enhancement of Naloxone Induced Analgesia by Pretreatment with Morphine" Pharma. Bioch. & Behav. (1989), 34:425-427.
Caruso et al., "Methadone and Naloxone in Combination (Naldone®) for the Treatment of Heroin Addicts"; Bristol Laboratories, pp. 1336-1341 (1973).
Chambers Dictionary of Science and Technology, Ed. P.M.B. Walker, Chambers, 1999, p. 803.
Chen et al., "Challenges and New Technologies of Oral Controlled Release," Oral Controlled Release Formulation Design and Drug Delivery: Theory to Practice (2010) pp. 257-277.
Chen et al., "Oral naloxone reverses opioid-associated constipation," Foreign Medical Sciences: Anesthesiology and Resuscitation, vol. 21, No. 5, p. 319 (2000).
Cherny Nathan I., "Opioid Analgesics"; Drugs May 1996:51 (5) pp. 713-737.
Chiang et al. "Clinical Evaluation of a Naltrexone Sustained-Release Preparation"; Drug and Alcohol Dependence (1985) 16, pp. 1-8.
Chiang et al., "Kinetics of a Naltrexone Sustained-Release Preparation"; Clin Pharmacy Thera (1984) vol. 36 No. 5, pp. 704-708.
Chih-Cheng Chien et al., "Sigma Antagonists Potentiate Opioid Analgesia in Rats", Neuroscience Letters 190 (1995), 137-139.
Chinese Official Action dated Nov. 9, 2011 corresponding to Chinese Application No. 200680005969.1 relating to the instant application.
Choi et al., "Opioid Antagonists: A Review of Their Role in Palliative care, Focusing on Use in Opioid-Related Constipation," J. of Pain and Symptom Management, vol. 24(1): 71-90 (2002).

(56) References Cited

OTHER PUBLICATIONS

Ciccocioppo et al., "Effect of Nociceptin/orphanin FQ on the Rewarding Properties of Morphine"; Eur. J Pharmacol (2000) vol. 404, pp. 153-159.
Citron et al., "Long-term administration of controlled release oxycodone tablets for the treatment of cancer pain," Cancer Investigation, vol. 16, No. 8, pp. 562-571 (1998).
Clark et al., "Symptom indexes to assess outcomes of treatment for early prostate cancer" Medical Care 39(10): 1118-1130 (Oct. 2001).
Clemens et al., "Combined oral prolonged-release oxycodone and naloxone in opioid-induced bowel dysfunction: review of efficacy and safety data in the treatment of patients experiencing chronic pain," Expert Opinion on Pharmacotherapy, 11(2):297-310 (2010).
Cohen, "Statistical Power Analyses for the Behavioral Sciences" ($2^{nd}$ Ed.) Hilsdale, NJ: Erlbaum (1988).
Comer et al., "Depot Naltrexone: Long-lasting Antagonism of the Effects of Heroin un Humans"; Psychopharmacology (2002) 159, pp. 351-360.
Complaint for Declaratory Judgment filed in the United States District Court for the Western District Court of Virginia on Nov. 17, 2008, Civil Action No. 1:08CV00050.
Crabtree et al., "Review of Naltrexone, a long-acting Opiate Antagonist"; Clinical Pharmacy, vol. 3 (1984) pp. 273-280.
Crain et al., "Acute thermal hyperalgesia elicited by low-dose morphine in normal mice is blocked by ultra-low-dose naltrexone, unmasking potent opioid analgesia"; Brain Research (2001) vol. 888, pp. 75-82.
Crain et al., "Ultra-Low Concentrations of Naloxone Selectively Antagonize Excitory Effects of Morphine on Sensory Neurons, Thereby Increasing Its Antinociceptive Potency and Attenuating Tolerance/Dependence During Chronic Cotreatment," Proc. Natl. Acad. Sci. USA (1995) 92:10540-10544.
Crain, SM at al., "Antagonists of excitatory opioid receptor functions enhance morphine's analgesic potency and attenuate opioid tolerance/dependence liability" Pain, 84:121-131 (2000).
Culpepper-Morgan et al., "Treatment of opioid-induced constipation with oral naloxone: A pilot study." Clinical Trials and Therapeutics, (1992) vol. 52(1): 90-95.
Davies, S., "Rising to the pain challenge," Drug News Perspect, 19(10):653-8 (2006).
Delbarre et al., "Naloxone effects on blood pressure, analgesia and dieresis in spontaneous hypertensive and normotensice rats," Neuroscience Letters, vol. 30; pp. 167-172 (1982).
Deyo RA et al., "Reproducibility and responsiveness of health status measures. Statistics and strategies for evaltuttion." Cont. clin. Trials 12: 142S-158S (1991).
Di Giannuario et al., "Orphanin FQ reduces morphine-induced dopamine release in the nucleus accumbens: a microdialysis study in rats"; Neurosci. Lett (1999) vol. 272 pp. 183-186.
Dictionary of Modern Computer Terms, S.-P.: BHV-Petersburg, p. 215 (2004) (English translation).
Drossman DA et al., Rome II: The Functional Gastrointestinal Disorders , ($2^{nd}$ ed.) McLean, VA: Dawson Associates (2000).
Ebell et al., eds. Die Schmerzebehandlung von Tumorpatienten, Thieme 1994 (Supportive Malinahmen in der Onkologie, Band 3) (in German, w/Engl. Translation).
Eissenberg,E et al., "Buprenophine's physical dependence potential: Antagonist-precipitated withdrawal in humans" J. Pharmacol. Exp. Therapeut., 276(2):449 (1996).
Endo Opposition, filed by Mundipharma in AU against AU 2002305559, Oct. 1, 2008.
EP Application No. EP06111805.5: Jul. 10, 2008 Response to Office Communication dated Feb. 19, 2008.
EP Application No. EP10176720.0: Mar. 1, 2011 European Search Opinion and Search Report.
EP Application No. EP10180364.1: Office Communication and European Search Report, dated Dec. 12, 2010 (8 pages).
EP Application No. EP10180425.0: Office Communication and European Search Report, dated Dec. 12, 2010 (8 pages).
EP Application No. EP11177513.6: European Search Report and Search opinion dated Feb. 2, 2012.
EP Application No. EP11177516.9: European Search Report and Search opinion dated Feb. 2, 2012.
EP Application No. EP11177518.5: European Search Report and Search opinion dated Feb. 2, 2012.
EP Application No. EP11177520.1: European Search Report and Search opinion dated Feb. 2, 2012.
Excerpt from Industrial Pharmacy, "Classification of drug delivery systems," 1996 (English translation).
Extended European Search Report dated Apr. 12, 2012 corresponding to European Application No. 10176716.8.
Fink et al., "Naloxone in Heroin Dependence"; Clin Pharm and Thera. vol. 9, No. 5;pp. 568-577, (1968).
Fishman et al., "Disposition of Naloxone-7,8-3H in Normal & Narcotic Dependent Men"; J. Pharm. and Exper. Thera (1973)vol. 10 No. 2;pp. 575-580.
Forth et al., Allgemeine und Spezielle Pharmakologie und Toxikologie, 7. Auflage, 1996, Spektrum Akadcmischer Verlag, Heidelberg Berlin Oxford.
Foss et al., "Dose related Antagonism of the Emetic Effect of Morphine by Methylnaltrexone in Dogs",J. Clin Pharmacol (1993), 33:747-751.
Foss J.F., et al. Abstract, "Prevention of Apomorphine- or Cisplatin-induced emesis in the dog by combination of Methylnaltrexone and Morphine",Cancer Chemother Pharmacol (1998); 42(4):287-91.
Fraser Albert D., et al., "Clinical Toxicology of Drugs Used in the Treatment of Opiate Dependency"; Clinical Toxicology I (1990) vol. 10, No. 2; pp. 375-386.
Freye et al., 'Effects of Tramadol and Tilidine/Naloxone on Oral-Caecal Transit & Pupillary light Reflex'; Arzneim-Forsch/Drug Res. 50(I)(2000)pp. 24-30.
Fudala et al., "Effects of Buprenorphine and Naloxone in Morphine-Stabilized Opioid Addicts"; Drug and Alcohol Dependence 50 (1998) pp. 1-8.
Fudala et al., "Human Pharmacology and Abuse Potential of Nalmefene"; Clin Pharm and Thera (1991) vol. 49, 3, pp. 300-306.
Gal et al., "Prolonged Blockade of Opioid Effect with Oral Nalmefene"; Clin Pharm and Thera (1986) pp. 537-542.
Gan et al., "Opioid-Sparing Effects of a Low-Dose Infusion of Naloxone in Patient-Administered Morphine Sulfate," Anesthesiology (1997), 87(5):1075-1080.
Gerra et al., "Clonidine and Opiate Receptor Antagonists in the Treatment of Heroin Addiction"; J. Substance Abuse Treatment (1995) vol. 12, 1, pp. 35-41.
Ghodse et al., "Opioid analgesics and Narcotic Antagonists"; Side Effects of Drugs (2000) Annual 23, chpt 8 pp. 96-113.
Glatt William, M.D. FACP, "A New Method for Detoxifying Opioid-Dependent Patients"; J. Substance Abuse Treatment (1999) vol. 17, No. 3,pp. 193-197.
Gold et al. "Rapid Opioid Detoxification During General Anesthesia"; Anesthesiology (1999) vol. 91, No. 6, pp. 1639-1647.
Goliber (Benchtop Evaluations of Tampering with Pharmaceutical Dosage Forms, Opioid Abuse Resistance Conference, Oct. 2005—Accessed from http://www.thci.org/opioid/oct05docs/TAB%205.8%20Gober.%20Benchtop%20Evaluations%20of%20Tampering%20with%20Pharmaceutical%20Disage%20Forms.pdf on Nov. 17, 2010.
Gonzalez et al., "Naltrexone: A Review of its Pharmacodynamic and Pharmacokinetic Properties and Therapeutic Efficacy in the Management of Opioid Dependence," Drugs (1988), 35:192-213.
Goodman and Gilman's The Pharmacological Basis of Therapeutics (Tenth Edition (2001), McGraw Hill.
Goodridge et al., "Factors associated with opioid dispensation for patients with COPD and lung cancer in the last year of life: A retrospective analysis," Int. J. of COPD, 2010, 5:99-105.
Greenwald et al., "Comparative Clinical Pharmacology of Short-Acting Opioids in Drug Abusers"; J. Pharm and Exper Thera (1996) vol. 277, No. 3, pp. 1228-1236.
Grimm, "Extension of the International Conference on Harmonization Tripartite Guideline for Stability Testing of New Drug

(56) References Cited

OTHER PUBLICATIONS

Substances and Products to Countries of Climatic Zones III and IV," Drug Development and Industrial Pharmacy, vol. 24, No. 4, pp. 312-324 (1998).
Gupta et al., "Morphine Combined with Doxapram or Naloxone"; Anesthesia (1974) vol. 29, pp. 33-39.
Guyatt et al., "Interpreting treatment effects in randomized trials" Br. Med. J. 316(7132): 690-693 (1998).
Guyatt et al., "Measuring change over tune: assessing the usefulness of evaluative instruments" J. Chronic Dis. 40(2): 171-178 (1987).
Hagen, et al. "Efficacy, Safety, and Steady-State Pharmacokinetics of Once-A-Day Controlled-Release Morphine (MS Contin XL) in Cancer Pain," Journal of Pain and Symptom Management (2005) vol. 29, No. 1, pp. 80-90.
Han et al., "Muccoadhesive buccal disks for novel nalbuphine prodrug controlled delivery; effect of formulation variable on drug release and mucoadhesive performance"; International J. Pharm (1999) vol. 177, pp. 201-209.
Handal et al., "Naloxone"; Annals of Emergency Medicine (1983) vol. 12:7, pp. 438-445.
Hanson Analgesic, Antipyretic and Anti-Inflammatory Drugs in Remington's Science and Practice of Pharmacy (1995), 2:1207.
Harris et al., "Buprenorphine and Naloxone co-administration in opiate dependent patients stabilized on sublingual buprenorphine"; Drug and Alcohol Dependence (2000) vol. 61, pp. 85-94.
Hawkes et al., "Effect of enteric-release formulation of naloxone on intestinal transit in volunteers taking codeine"; Aliment Pharm Ther (2001) vol. 15, pp. 625-630.
Hays et al., "Assessing reliability and validity of measurement in clinical trials" in: Staquet at al., (eds.) Quality of Life in Clinical Trials: Methods and Practice Oxford: Oxford University Press (1998).
Hening et al., "Dyskinesias while awake and periodic movements in sleep in restless legs syndrome: Treatment with opioids," Neurology, vol. 36, pp. 1363-1366 (1986).
Hermanns et al., "Prolonged-release oxycodone/naloxone in the treatment of neuropathic pain results from a large observational study," Expert Opin. Pharmacother. vol. 13, No. 3, pp. 299-311 (2012).
Hexal Opposition to related application EP 1492506, dated Sep. 30, 2009.
Hiroshi K., et al., "Pharmacology," Hirokawa Bookstore, 1992, p. 70-72.
Hogger et al., "Comparison of tilidine/naloxone, tramadol and bromfenac in experimental pain: a double-blind randomized crossover study in healthy human volunteers"; International J. Clin Pharm and Thera (1999) vol. 37, No. 8,pp. 377-385.
Holmes et al., "Inhibiting Spinal Dynorphin A Component Enhances Intrathecal Morphine Antinociception in Mice", Anesth. Analg. (1993), 77:1166-73.
Holzer et al., "Opioid-induced bowel dysfunction in cancer-related pain: causes, consequences and a novel approach for its management," Journal of Opioid Management, 5(3): 145-151 (2009).
Holzer et al., "Opioid receptors in the gastrointestinal tract," Regulatory Peptides, vol. 155, No. 1-3, pp. 11-17 (2009).
Hopp et al., "Analgesic efficacy of oxycodone in combination with naloxone as prolonged release (PR) tablets in patients with moderate to severe chronic pain [abstract PT 226]," Presented at the 12th World Congress on Pain, International Association for the Study of Pain (IASP), Glasgow, Scotland, UK, MIS 4789879, Aug. 17-22, 2008.
Hopp et al., "Pain 2: Oral prolonged-release (PR) oxycodone/naloxone combination reduces opiod-induced bowel dysfunction (OIBD) in chronic pain patients [abstract 40]," Presented at the 5th Research Forum of the European Association for Palliative Care, Palliat. Med., 22(4):441 (2008).
Howes et al., "The Pharmacology of TR5109, a new Narcotic Agonist/Antagonist Analgesic"; NIDA Research (1979) pp. 99-105.
Hughes et al., "Buprenorphine for pain relief in a patient with drug abuse," The American Journal of Drug and Alcohol Abuse, vol. 17, No. 4, pp. 451-455 (1991).
Hussain et al., "Buccal and oral bioavailability of naloxone and naltrexone in rats"; Int. J. Pharmaceutics (1987) vol. 36, pp. 127-130.
Hussain, MA. "Improved buccal delivery of opioid analgesics and antagonists with bitterless prodrugs" Pharm. Res. 5(9): 615-618 (1988).
International Search Report and Written Opinion corresponding to International Application No. PCT/EP2014/065816 dated Sep. 12, 2014.
Inoue, "On the Treatment of Restless Legs Syndrome," Progress in RLS Research, vol. 24, No. 3, pp. 892-897 (2004).
Jasinski D.R., "Assessment of the Abuse Potentiality of Morphine-like Drugs (Methods Used in Man)"; Drug Addiction (1977) pp. 197-258.
Jasinski et al., "The human pharmacology and abuse potential of N-allylnoroxymorphone naloxone"; J. Pharm and Exper Thera (1967) vol. 157, No. 2, pp. 420-426.
Johnson et al., "Buprenorphine and Naloxone for Heroin Dependence"; Substance Use Disorders (2000) pp. 519-526.
Jones et al., "Nalmefene:blockade of intravenous morphine challenge effects in opioid abuse in humans"; Drug and Alcohol Dependence (2000) vol. 60, pp. 29-37.
Judson et al., "The Naloxone Test for Opiate Dependence," Clin. Pharmacol. Ther., vol. 27, No. 4, pp. 492-501, (1980).
Kaasa et al., "New therapeutic principles for adverse effects on upper and lower gastrointestinal tract in patients treated with opioid analgesics," Scandinavian Journal of Pain 1, S1, pp. 512-517 (2009).
Kanof et al., "Levels of Opioid Physical Dependence in Heroin Addicts," Drug and Alcohol Dependence, 27 (1991) 253-262.
Kanof, PD et al., "Clinical characteristics of naloxone-precipitated withdrawal in human opioid-dependent subjects", J. Pharmacol. Exper. Therapeut, 260(1): 355 (1992).
Kapoor, S., "Emerging New Therapeutic Options for the Management of Opioid Induced Constipation," J. of Pain and Palliative Case Pharmacotherapy, 24(1):98-99 (2010).
Kazis et al., "Effects sizes for interpreting changes in health status", Med. Care 27(3 Suppl.): S178-S189 (1989).
King et al., "Naltrexone Biotransformation and Incidence of Subjective Side Effects: A Preliminary Study"; Alcoholism: Clin and Exper Res (1997) vol. 21, No. 5, pp. 906-909.
Kogan et al., "Estimation of the Systemic Availability and Other Pharmacokinetic Parameters of Naltrexone in Man after Acute and Chronic Oral Administration"; Res. Comm. in Chem. Path. and Pharm (1977) vol. 18, No. 1, pp. 29-34.
Korean Official Action dated Jun. 12, 2012 corresponding to Korean Application Appeal No. 2011HUH10030 relating to the instant application.
Kosten et al., "Opioid antagonist challenges in buprenorphine maintained patients"; Drug and Alcohol Dependence (1990) vol. 25, pp. 73-78.
Kosten Thomas R., M.D.,"Buprenorphine for Benzodiazepine-Abusing Heroin Addicts"; Amer J of Psychiatry (1994) vol. 1, p. 151.
Kreek et al., "Drug Interactions with Methadone," *Ann. N.Y. Acad. Sci.*, 281, 350-371 (1976).
Krylov, Drug Register of Russia, Encyclopedia of Drugs, (2001) entries for "Nalbuphine," "Naloxone," and "Naltrexone" (English Translation).
Kurland et al., "Naloxone and the Narcotic Abuser: A Controlled Study of Partial Blockade"; Inter. J. of the Addictions (1974) vol. 9, No. 5, pp. 663-672.
Kurz et al., "Opioid-Induced Bowel Dysfunction: Pathophysiology and Potential New Therapies," Drugs, vol. 63, No. 7, pp. 649-671 (2003), Abstract.
Kuusniemi et al., "Prolonged-Release Oxycodone/Naloxone in postoperative pain management: From a randomized clinical trial to usual clinical practice,"Journal of International medical Research, vol. 40, No. 5, pp. 1775-1793 (2012).

(56) References Cited

OTHER PUBLICATIONS

Lapierre "Acetaminophen Boosts Liver Toxicity Alone, as Combination Therapy-Jama" Health News Daily, vol. 18 Issue 128 dated Jul. 6, 2006.

Latasch et al., "Aufhebun einer Morphin-induzierten Obstipation durch orales Naloxon," with translation ("Oral Naloxone Antagonizes Morphine-Induced Constipation"), Anaesthesist, 46, 191-194 (1997).

Lee et al., "Nalbuphine Coadministered with Morphine Prevents Tolerance and Dependence"; Anesth Analg (1997) vol. 84, pp. 810-815.

Leehey et al., "Naloxone increases water and electrolyte excretion after water loading in patients with cirrhosis and ascites," J. Lab. Clin. Med., vol. 118, No. 5, pp. 484-491 (1991).

Leeling et al., "Disposition and metabolism of codorphone in the rat, dog, and man"; Drug Metabolism and Disposition (1982) vol. 10, No. 6, pp. 649-653.

Lehman et al.,"Influence of Naloxone on the Postoperative Analgesic and Respiratory effects of Buprenorphine"; Eur. J. Clin Pharm (1988) vol. 34, pp. 343-352.

Leidy et al., "Recommendations for evaluating the validity of quality of life claims for labeling and promotion" Value in Health 2(2): 113-127 (1999).

Levine et al., "Potentiation of Pentazocine Analgesia by Low-dose Naloxone"; J Clin Invest (1988) vol. 82, pp. 1574-1577.

Levy M.H., "Advancement of opioid analgesia with controlled-release oxycodone," Eur. J. Pain, vol. 5, Suppl. A, pp. 113-116 (2001), Abstract.

Li Chen et al., "Oral naloxone reverses opioid-associated constipation" Foreign Medical Sciences: Anaesthesiology and Resuscitation, 21(5): 319 (2000).

Light et al., "Effects of Oral Morphine in Breathlessness and Exercise tolerance in Patients with Chronic Obstructive Pulmonary Disease," Am. Rev. Respir. Dis., (1989) vol. 139, pp. 126-133.

Liu et al., "Low dose oral naloxone reverses opioid-induced constipation and analgesia," Journal of Pain and Symptom Management, vol. 23, No. 1, pp. 48-53 (2002).

Loimer et al., "Combined Naloxone/Methadone Preparations for Opiate Substitution Therapy"; J. of Substance Abuse Treatment (1991) vol. 8, pp. 157-160.

Lorcet, Physicians' Desk Reference 48th ed., 1994; pp. 2388-2390.

Lortab, Physicians' Desk Reference 48th ed., 1994; pp. 2498-2500.

Lowenstein et al., "Combined prolonged release oxycodone and naloxone improves bowel function in patients receiving opioids for moderate-to-severe non-malignant chronic pain: a randomized controlled trial," Expert Opinion on Pharmacotherapy, 10(4):531-543 (2009).

Markman Opinion and Order (D.I. 156) in *King Pharm., Inc. et al. v. Purdue Pharma L.P.*, No. 1:08-cv-00050 (W.D. Va. Jun. 22, 2010).

Martin et al. "Bioavailability Investigation of a New Tilidine/Naloxone Liquid Formulation Compared to a Reference Formulation";Arzneim-Forsch./Drug Res. (1999) vol. 49, pp. 599-607.

Martin et al., "Demonstration of Tolerance to and Physical Dependence on N-allynormorphine (Nalorphine)";J. of Pharm and Exper Thera (1965) vol. 150, No. 3. pp. 437-442.

Medzon, R, "Naltrexone and Nalmefene," Clinical Toxicology Review, vol. 19, No. 3, Dec. 1996.

Meissner et al., "Oral naloxone reverses opioid-associated constipation", Pain, vol. 84, pp. 105-109 (2000).

Meissner, W et al., "A randomised controlled trial with prolonged-release oral oxycodone and naloxone to prevent and reverse opioid-induced constipation", Eur. J. Pain, 13: 56-64 (2009).

Mendelson et al., "Buprenophine and naloxone Interactions in Methadone Maintenance Patients"; Society of Biological Psychiatry (1997) vol. 41, pp. 1095-1101.

Mendelson et al., "Buprenorphine and naloxone combinations: the effects of three dose ratios in morphine stabilized, opiate-dependent volunteers"; Psychopharmacology (1999) vol. 141, pp. 37-46.

Mendelson J., et al, "Buprenorphine and Naloxone Interactions in Opiate Dependent Volunteers," Clin. Phar. Ther. (1996), 60;105-114.

Meng et al., "Morphine Induces bacterial translocation in mice by compromising Intestinal barrier function in a TLR-dependent manner," PLOS One, vol. 8, No. 1, pp. 1-13 (2013).

Miaskowski et al., "Inhibition of Spinal Opioid Analgesia by Supraspinal Administration of Selective Opioid Antagonists", Brain Research (1992), 596:41-45).

Mikus, G., "Combining Opioid Agonists and Antagonists as a Solution for Opioid-induced Constipation," European Gastroenterology and Hepatology Review, 4(2):71-74 (2008).

Mims, Jan. 2005, pp. 120-125.

Mollereau et al., "ORL 1, a novel member of the opioid receptor family: Cloning, functional expression and localization"; FEBS letters 341 (1994), pp. 33-38.

Mueller-Lissner, "Fixed Combination of Oxycodone with Naloxone: a New Way to Prevent and Treat Opioid-Induced Constipation." Adv. Ther. (2010) 27(9):581-590.

Muller-Lissner et al., "Oral Prolonged release (PR) oxycodone/naloxone combination reduced opioid-induced bowel dysfunction (OIBD) in patients with severe chronic pain (abstract 189)," Presented at the 2nd International Congress on Neuropathic Pain, Berlin, Germany, Published in Eur. J. Pain, 11 (S1): S82, Jun. 7-10, 2007.

Mundipharma Clinical Study Report A2-3759 "Validation of Bowel Function Index" dated Jun. 15, 2005 (Rev. Jul. 12, 2005).

Mundipharma Clinical Study Report OXN 2401 "Optimization of Naloxone-Oxycodone Ratio in Pain Patients" Final Version dated Jun. 3, 2005.

Mundipharma Pharmaceuticals Limited "Targin 5/2.5mg, 10mg/5mg, 20mg/10mg and 40/20mg prolonged release tablets" dated Jun. 7, 2013.

Nadstawek et al., "Patient assessment of the efficacy and tolerability of coadministered prolonged release oral oxycodone and naloxone in severe chronic pain (abstract SAT0375)," Presented at the 8th Annual European League Against Rheumatism (EULAR 2007), Barcelona, Spain, Published in Ann. Rheum Dis., 66(Suppl. 2):543, Jun. 13-16, 2007.

Nadstawek, J at al., "Patient assessment of a novel therapeutic approach for the treatment of severe chronic pain" Int. J. Clin. Pract., 62(8): 1159-1167 (2008).

Neunschwander et al., Palliative Medicine at a Glance, 1999 (whole book).

Nichols et al., "Improved bowel function with a combination of oxycodone and naloxone (OXN) as prolonged-release (PR) tablets in patients with moderate to severe chronic pain (abstract PT225)," Presented at the 12th World Congress on Pain, International Association for the Study of Pain (IASP), Glasgow, Scotland, UK, Aug. 17-22, 2008.

Nieuwenhuijs et al., "The role of interdigestive small bowel motility in the regulation of gut microflora, bacterial overgrowth, and bacterial translocation in rats," Annals of Surgery, vol. 228, No. 2, pp. 188-193 (1998).

Nolte, T., "Prolonged-release oxycodone/naloxone is effective and safe in cancer pain (abstract 66)," Encore presentation at the 12th World Congress on Pain, International Association for the Study of Pain (IASP), Glasgow, Scotland, UK, Aug. 17-22, 2008.

Nolte, T., "Prolonged-release oxycodone/naloxone is effective and safe in clinical use (abstract 275)," Encore presentation at the 5th Research Forum of the European Association for Palliative Care, Published in Palliative Medicine, 22(4):484-5 (2008).

Nolte, T., "Prolonged-release oxycodone/naloxone is effective and safe in clinical use (abstract PO325)," Presented at the 28th German Congress on Cancer, Published in Onkologie, Berlin, Germany, 31(Suppl. 1):165-6, Feb. 20-23, 2008.

Norman et al., "Interpretation of changes in health-related quality of life. The remarkable universality of half a standard deviation" Med. Care, 41: 582-592 (2003).

Nunnally et al., Psychometric Theory, (3rd ed.) NY: McGraw-Hill (1994).

(56) References Cited

OTHER PUBLICATIONS

Nutt et al., "Methadone-naloxone mixture for use in methadone maintenance programs"; Clin Pharm and Ther. vol. 15, No. 2., pp. 156-166 (1974).
Oppermann M., "Neue Arzneimittel zur Behandlung der Opioid-induzierten Obstipation: der Mechanismus-basierte Ansatz von Methylnaltrexon, Naloxon and Alvimopan," Fortbildungstelegramm Pharmazie; May 1; vol. 3, pp. 117-131 (2009).
Oxygesic® Product Information, 1997-2001 (in German, w/ English translation).
Package Insert for OxyContin®, Purdue Pharma L.P. (Mar. 18, 2004).
Paille et al., "An open six-month study of the safety of Transipeg for treating constipation in community medicine," J. Clin. Res., vol. 2, pp. 97-254 (1999).
Pamuk et al., "Revalidation of description of constipation in terms of recall bias and visual scale analog questionnaire," Journal of Gastroenterology and Hepatology (2003), 18, 1417-1422.
Pappagallo, M., "Incidence, prevalence, and management of opioid bowel dysfunction," Am. J. Surg. (2001) 182 suppl. 11S-18S.
Paronis et al., "Increased Analgesic Potency of Mu Agonists after Continuous Naloxone Infusion in Rats"; J for Pharm Exper Thera (1991), 259 (2), pp. 582-589.
Parwartikar et al., "Naloxone-Methadone Combination for the Treatment of Opiate Dependence"; Missouri Institute of Psychiatry, pp. 1350-1354, (1973).
Parwatikar et al., "Methadone-naloxone in combination for the Treatment of Heroin Addicts"; Clin. Pharm and Thera, vol. 14, No. 6, pp. 941-948, (1973).
PCT Application PCT/EP2003/003540: International Preliminary Examination Report dated Aug. 17, 2004.
PCT Application PCT/EP2005/006155: International Search Report and Written Opinion of the International Searching Authority dated Aug. 25, 2005.
PCT Application PCT/EP2005/006155: International Search Report dated Aug. 25, 2005 (2 pages).
PCT Application PCT/EP2006/060336: International Preliminary Report on Patentability and Written Opinion of the International Searching Authority dated May 18, 2007.
PCT Application PCT/EP2006/060341: International Preliminary Report on Patentability and Written Opinion of the International Searching Authority dated May 16, 2007.
PCT Application PCT/EP2008/062834: International Preliminary Report on Patentability and Written Opinion of the International Searching Authority dated Mar. 30, 2010.
PCT Application PCT/EP2009/058630: International Search Report and Written Opinion of the International Searching Authority dated Oct. 9, 2009.
Peachey et al., "Assessment of Opioid Dependence with Naloxone," British Journal of Addiction (1988) 83(2), 193-201.
Philippe et al., "Mu opoid receptor expression is increased in inflammatory bowel diseases: implications for homeostatic intestinal inflammation," Gut, vol. 55, No. 6, pp. 815-823 (2006).
Physician's Desk Reference (2001) see "Oxycontin," pp. 2697-2701.
Physician's Desk Reference (2001) see "Revia," pp. 1146-1149.
Physician's Desk Reference 48th ed.; 1994; "Talwin," 2120-2121, Montvale, NJ.
Pitts et al., "Antinociceptive and Response Rate-Altering Effects of Kappa Opioid Agonists, Spiradoline, Enadoline and U69,593, Alone and in Combination with Opioid Antagonists in Squirrel Monkeys"; J of Pharm and Exper Thera (1994) vol. 271, No. 3, pp. 1501-1508.
Poole et al., "The Effect of Sustained-Release Morphine on Breathlessness and Quality of Life in Severe Chronic Obstructive Pulmonary Disease," Am. J. Respir. Crit. Care Med, vol. 157, pp. 1877-1880 (1998).
Portenoy et al., "Breakthrough pain: characteristics and impact in patients with cancer pain," Pain, vol. 81, pp. 129-134 (1999).
Portenoy et al., "Breakthrough pain: definition, prevalence and characteristics," Pain, vol. 41, pp. 273-281 (1990).

Press Release "International Patent Application to Be Published on Abuse-Resistant Pain Reliever Being Developed by Perdue Pharma"; Aug. 8, 2001.
Preston et al., "Abuse liability and studies of opioid agonist-antagonists in humans"; Drug and Alcohol Dependence (1991) vol. 28, pp. 49-82.
Preston et al., "Buprenorphine and Naloxone alone and in combination in Opioid-dependant Humans"; Psychopharmacology (1988), vol. 94, pp. 484-490.
Preston et al., "Differential Naltrexone Antagonism of Hydromorphone and Pentazocine Effects in Human Volunteers"; J of Pharm and Ezper Thera (1993) vol. 264, No. 2 pp. 813-823.
Preston et al., "Effects of Sublingually given naloxone in Opioid-dependant human volunteers"; Drug and Alcohol Dependence (1990) vol. 25, pp. 27-34.
Rapaka et al., "Discovery of Novel Opioid Medications"; NIDA Research Monograph 147 (1995) p. 55-83.
Rawal, et al., "An experimental study of urodynamic effects of epidural morphine and of naloxone reversal", Anesth Analg. Jul. 1983;62(7):641-647.
Reents et al., "Naloxone and Naltrexone Application in COPD," Chest, vol. 92, No. 1, pp. 217-219 (1988).
Reimer et al., "Meeting the challenges of opioid-induced constipation in chronic pain management—a novel approach," Pharmacology, 83:10-17 (2009).
Rentz et al., "Validation of the Bowel Function Index to detect clinically meaningful changes in opioid-induced constipation," Journal of Medical Economics (JME), 12(0):371-383 (2009).
Resnick et al., "Naloxone Precipitated Withdrawal: A Method for Rapid Induction Onto Naltrexone," Clinical Pharmacology and Therapeutics, vol. 21, No. 4, pp. 409-413; received for publication Nov. 16, 1976.
Revicki et al., "Recommendation on health-related quality of life research to support labeling and promotional claims in the United States", OOL Research 9(8): 887-900 (2000).
Richter et al., "Clinical Investigation on the Development of Dependence during Oral Therapy with Tramadol"; Arzniem-Forsch/Drug Res. 35 (No. II)(1985)pp. 1742-1744.
Rosen et al., "A Pilot Study of Dextromethorphan in Naloxone-Precipitated Opiate Withdrawal"; European J. of Pharm. (1996) vol. 307, pp. 251-257.
Rosen et al., "The effect of Lamotrigine on Naloxone-precipitated Opiate withdrawal"; Drug and Alcohol Dependence (1998) vol. 52, pp. 173-176.
Rosow et al., "Reversal of opioid-induced bladder dysfunction by intravenous naloxone and methylnaltrexone," Clin. Pharm. & Ther., vol. 82, No. 1, pp. 48-53 (2007).
Rote Liste 2004, Jan. 1, 2004; Frankfurt/Main, vol. 2004, pp. 05001-05033.
Sandner F., "Hope for patients with chronic pain: naloxone and oxycodone fixed combination offers analgesia and prevention of constipation also during sleep," J. of Pham. and Therapy, vol. 16; No. 6; pp. 179-180 (2007).
Sandner-Kiesling et al., "Long-term efficacy and safety of combined prolonged-release oxycodone and naloxone in the management of non-cancer chronic pain," International Journal of Clinical Practice, 64(6):763-774 (2010).
Schenck et al., "Letter to the Editor," Sleep Med., vol. 4, No. 3, p. 251 (2003).
Schenck et al., "Severe, childhood-onset, idiopathic, life-long insomnia responding selectively to opiate therapy: case report with 19 year follow-up," Sleep Med., vol. 2, No. 6, pp. 531-536 (2001).
Schmidt, W.K. "Alvimopan (ADL Aug. 2698) Is a Novel Peripheral Opioid Antagonist," The American Journal of Surgery, 182 (Suppl. to Nov. 2001) 27S-38S (2001).
Schuh et al., "Buprenorphine, Morphine and Naloxone Effects during Ascending Morphine Maintenance in Humans"; J. Pharm and Exper Thera (1996) vol. 278, 2, pp. 836-846.
Schuh et al., "Onset, Magnitude and Duration of Opioid Blockade Produced by Buprenorphine and Naltrexone in Humans"; Psychopharmacology (1999) vol. 145, pp. 162-174.
Schutter et al., "Innovative pain therapy with a fixed combination of prolonged-release oxycodone/naloxone: a large observational study

(56) References Cited

OTHER PUBLICATIONS under conditions of daily practice," Current Medical Research and Opinion, 26(6) : 1377-1387 (2010).
Shen et al., "Ultra-Low Doses of Naltrexone or Etorphine Increase Morphine's Antinocieceptive Potencey and Attenuate Tolerance/Dependence in Mice," Brain Research (1997), 757;176-190.
Shin Yakuzaigaku Soron (3rd revised edition), 1987, p. 148-151.
Simpson et al., "Fixed-ratio combination oxycodone/naloxone compared with oxycodone alone for the relief of opiod induced constipation in moderate-to-severe non-cancer pain," Current Medical Research and Opinion (CMRO), 24(12):3503-3512 (2008).
Smith et al., "Low-dose naltrexone as a treatment for active Crohn's disease," AGA Abstracts, S1397, XP009095749, p. A-218 (2006).
Smith et al., "Low-dose naltrexone therapy improves active Crohn's disease," The American Journal of Gastroenterology, vol. 102, No. 4 pp. 820-828 (2007).
Smith et al., "Single and multiple-dose pharmacokinetic evaluation of oxycodone and naloxone in an opioid agonist/antagonist prolonged-release combination in healthy adult volunteers," Clinical Therapeutics, 30(11):2051-2068 (2008).
Smith et al., "Prolonged-release oxycodone/naloxone tablets: Dose-proportional pharmacokinetics (abstract PW 256)," Presented at the 12th World Congress on Pain, International Association for the Study of Pain (IASP), Glasgow, Scotland, UK (MIS 4790606), Aug. 17-22, 2008.
Stevens et al., Nonspecific Excitatory Effects of Morphine: Reverse-Order Precipitated Withdrawal and Dose-Dose Interactions: Psychopharmacology (1981) vol. 75, pp. 210-211.
Stine et al., "Reduction of Opiate Withdrawal-like Symptoms by Cocaine Abuse during Methadone and Buprenorphine Maintenance"; Am. J. Drug and Alcohol Abuse (1994) vol. 20, 4, pp. 445-458.
Stine et al., "Use of Drug Combinations in Treatment of Opioid Withdrawal"; J. Clinical Psych. (1992) vol. 12, No. 3, pp. 203-209.
Stoller et al., "Effects of buprenorphine/naloxone in opioid-dependent humans" Psychopharmacology (2001) vol. 154, pp. 230-242.
Strain et al., "Acute Effects of Buprenorphine, hydromorphone and naloxone in methadone-maintained volunteers"; J. Pharm and Exper Thera (1992) vol. 261, No. 3, pp. 985-993.
Strain et al., "Effects of buprenorphine versus buprenorphine/naloxone tablets in non-dependent opioid abusers"; Psychopharmacology (2000) vol. 148, pp. 374-383.
Strain et al., "Opioid antagonist effects of dezocine in opioid-dependent humans"; Clin Pharm and Thera (1996) vol. 60, No. 2, pp. 206-217.
Strain et al., "Precipitated Withdrawal by Pentazocine in Methadone-Maintained Volunteers"; J. Pharm and Exper Thera (1993) vol. 267, No. 2, pp. 624-634.
Sunshine et al., "Analgesic Efficacy of Pentazocine Versus a Pentazocine-Naloxone Combination Following Oral Administration," Clin. J. Pain (1988), 4:35-40.
Suzuki et al., "Morphine conditioned place preference after chronic treatment with naloxone in the rat"; Research Communications in Substance Abuse (1991) vol. 12., No. 3., pp. 119-131.
Sykes "An investigation of the ability of oral naloxone to correct opioid-related constipation in patients with advanced cancer," Palliative Medicine (1996), 10:134-144.
Sykes "Oral naloxone in opioid-associated constipation," Lancet (1991) vol. 337 p. 1475.
Sykes, N.P., "Using Oral Naloxone in Management of Opioid Bowel Dysfunction," in *Handbook of Opioid Bowel Syndrome*, Chapter 9, (Yuan, C.-S. ed., The Haworth Medical Press 2005).
Tai et al., "Naltrexone: An Antagonist Therapy for Heroin Addiction"; NIDA (1997) 5 pages.
Trzepacz et al., "Response to Opioids in Three Patients with Restless Legs Syndrome," Am. J. Psychiatry, vol. 141, pp. 993-999 (1984).

U.S. Appl. No. 13/329,218, filed Aug. 15, 2013 Reply to Non-Final Office Action dated Feb. 15, 2013 (application corresponds to US Publication Citation No. A36).
U.S. Appl. No. 13/329,218: Final Office Action dated Dec. 5, 2013.
U.S. Appl. No. 14/058,068: Non-Final Office Action dated Dec. 16, 2013.
U.S. Appl. No. 14/058,068, filed Nov. 22, 2013 Third Preliminary Amendment.
U.S. Appl. No. 60/290,439, filed May 11, 2001.
Umbricht et al., "Naltrexone shortened opioid detoxification with buprenorphine"; Drug and Alcohol Dependence (1999) vol. 56 pp. 181-190.
Vaccarino et al., "Endogenous Opiates: 1999"; Peptides 21 (2000) pp. 1975-2034.
Vaccarino et al.,"Analgesia Produced by Normal Doses of Opioid Antagonists Alone and in Combination with Morphine", Pain (1989), 36:103-109.
Valoron® Product Information, 1997-2001 (in German, w/ English translation).
Vicodin, Physicians' Desk Reference 48th ed., 1994; pp. 1143-1145.
Vondrackova, D. et al., "Analgesic efficacy and safety of oxycodonein combination with naloxone as prolonged release tablets in patients with moderate to severe chronic pain", J. Pain 9(12):1144-1154 (Dec. 2008).
Walsh et al., "Effects of Naltrexone on Response to Intravenous Cocain, Hydromorphone and their Combination in Humans," (1996).
Walters et al., "Successful Treatment of the Idiopathic Restless Legs Syndrome in a Randomized Double-Blind Trial of Oxycodone Versus Placebo," Sleep, vol. 16, No. 4, pp. 327-332 (1993).
Wang et al., "cDNA cloning of an orphan opiate receptor gene family member and its splice variant"; FEBS letters 348 (1994) pp. 75-79.
Wang et al., "Crossover and Parallel Study of Oral Analgesics," J. Clin. Pharmacol (1981), 21:162-168.
Wang et al., "Inverse Agonists and neutral antagonists at mu opioid receptor (MOR): possible role of basal receptor signaling in narcotic dependence"; J. Neurochemistry (2001) vol. 77, pp. 1590-1600.
Wang et al., "Rating the Presence and Severity of Opiate Dependence," Clinical Pharmacology and Therapeutics, vol. 16, No. 4, pp. 653-657; received for publication Jan. 21, 1974.
Watkins et al. "Aminotransferase Elevations in Healty Adults Receiving 4 Grams of Acetaminophen Daily" Jama, Jul. 5, 2006 vol. 296 No. 1.
Way et al., "Responsivity to Naloxone during Morphine Dependence"; Annals New York Academy of Sciences, pp. 252-261, (1976).
Weinberg et al., "Sublingual absorption of selected opioid analgesics"; Clin Pharm Thera (1988) vol. 44, No. 3, pp. 335-342.
Weinhold et al., "Buprenorphine Alone and in Combination with Naltrexone in Non-Dependent Humans," Drug and Alcohol Dependence (1992), 30:263-274.
Wells et al., "In vivo Pharmacological Characterization of SoRI 9409, a Nonpeptidic Opioid-Agonist/-Antagonist that Produces Limited Antinociceptive Tolerance and Attenuates Morphione Physical Dependence"; J. Pharm and Exper Thera (2001) vol. 297, No. 2, pp. 597-605.
Wiesen et al., "The Safety and Value of Naloxone as a Therapeutic Aid," Drug and Alcohol Dependence, 2 (1977) pp. 123-130.
Wikler et al., "N-Allylnormorphine: Effects of single dose and Precipitation of Acute "Abstinence Syndromes" during addiction to morphine, methadone or heroin in man (post addicts)"; J. Pharmacol. Exp. Ther., 109, 8-20 (1953).
Wilkinson, "The Dynamics of Drug Absorption, Distribution, and Elimination," Goodman and Gilman's The Pharmacological Basis of Therapeutics, Chapter 1, Pharmacokinetics, copyright page and pp. 3-29 (2001).
Wilmington, Del., PR Newswire; New Data Published Describing Favorable Safety Profile of REVIA (Naltrexone Hydrochloride Tablets) When Used to Treat Alcohol Dependence, Dec. 1997.
Wodak Alex, "Drug Treatment for Opioid Dependence"; Australian Prescriber (2001) vol. 24, No. 1, pp. 4-6.
Woodward et al., "Prolonged-release oxycodone/naloxone tablets: Pharmacokinetics in the elderly (abstract)," Presented at the 12th

(56) References Cited

OTHER PUBLICATIONS

World Congress on Pain, International Association for the Study of Pain (IASP), Glasgow, Scotland, UK, Abstract PW 255, (MIS 4789067), Aug. 17-22, 2008.

Wright et al., "Acute physical dependence in Humans; repeated naloxone-precipitated withdrawal after a single-dose of methadone"; Drug and Alcohol Dependence (1991) vol. 27, pp. 139-148.

Wyrwich et al,, "Further evidence supporting an SEM-based criterion for identifying meaningful intra-indivisual changes in health-related quality of life", J. Clin. Epidemiol., 52:861-873 (1991).

Yoburn et al., "Opioid Antagonist-induced Receptor Upregulation: Effects of Concurrent Agonist Administration"; Brain Research Bulletin (1994), vol. 33, pp. 237-240.

Yoburn et al., "Supersensitivity to Opioid Analgesics Following Chronic Opioid Antagonist Treatment: Relationship to Receptor Sensitivity"; Pharmacology Bio Beh (1995) vol. 51 No. 2, pp. 535-539.

Yuan et al., "Efficacy of Orally Administered Methylnaltrexone in Decreasing Subjective Effects After Intravenous Morphine", Drug and Alcohol Dependence (1998); 52:161-165.

Yuan et al., "The Safety and Efficacy of Oral Methylnaltrexone in Preventing Morphine-induced Delay in Oral-Cecal Transit Time", Clinical Trials and Therapeutics (1997), 61:467-475.

Zaks et al., "Naloxone Treatment of Opiate Dependence"; JAMA (1971) vol. 215, No. 13, pp. 2108-2110.

Zech et al., "Validation of World Health Organization Guidelines for Cancer Pain Relief: A 10-year prospective study" Pain 63: 65-76 (1995).

Zeppetella et al., "Opioids for cancer breakthrough pain: A pilot study reporting patient assessment of time to meaningful pain relief," J. of Pain and Symptom Management, vol. 25, No. 5, pp. 563-567 (2008).

Zhang et al., "Down-Regulation of-Opioid Receptors in Rat and Monkey Dorsal Root Ganglion Neurons and Spinal Cord After Peripheral Axotomy"; Neuroscience (1998) vol. 82, pp. 223-240.

Zhu et al., "Naltrexone-precipitated morphine withdrawal in infant rat is attenuated by acute administration if NOS inhibitors but not NMDA receptor antagonists"; Psychopharmacology (2000) vol. 150, pp. 325-336.

Zou, W "A clinical analysis of 18 cases of naloxone treating pruritus due to cholestia, hebei", Modern Journal of Integrated Traditional Chinese and Western Medicaine 8(1):43 (1999).

Achkar et al. "Candida Infections of the Genitourinary Tract", Clinical Microbiology Reviews, Apr. 2010, p. 253-273 vol. 23, No. 2.

Azcárate-Peril et al., "The Intestinal Microbiota, Gastrointestinal Environment and Colorectal Cancer: A Putative Role for Probiotics in Prevention of Colorectal Cancer?", Am J Physiol Gastrointest Liver Physiol 301: G401-G424, 2011.

Bures et al., "Small Intestinal Bacterial Overgrowth Syndrome", World J Gastroenterol 2010, 16(24): 2978-2990.

Grenham et al., "Brain—Gut—Microbe Communication in Health and Disease", Frontiers in Physiology Gastrointestinal Sciences, 2011, vol. 2, Article 94, 1-15.

Harari et al., "The effect of morphine on mast cell—mediated mucosal permeability", Surgery (2006) vol. 139, No. 1, 54-60.

Jost, W.H., "Gastrointestinal dysfunction in Parkinson's Disease", Journal of the Neurological Sciences 289 (2010) 69-73.

Larsen et al., "Gut Microbiota in Human Adults with Type 2 Diabetes Differs from Non-Diabetic Adults", PLoS One 5(2): e9085 (2010) (10 pages).

Ley et al., "Obesity alters gut microbial ecology", PNAS, 2005, vol. 102, No. 31, 11070-11075.

Noor et al., "Ulcerative Colitis and Irritable Bowel Patients Exhibit Distinct Abnormalities of the Gut Microbiota", BMC Gastroenterology 2010, 10:134 (9 pages).

Ponnusamy et al., "Microbial Community and Metabolomic Comparison of Irritable Bowel Syndrome Faeces", Journal of Medical Microbiology (2011), 60, 817-827.

Quigley et al., "Small Intestinal Bacterial Overgrowth", Infect Dis Clin Am 24 (2010) 943-959.

Rausch et al., "Colonic mucosa-associated microbiota is influenced by an interaction of Crohn disease and FUT2 (Secretor) genotype", PNAS, 2011, vol. 108, No. 47, 19030-19035.

Runkel et al., "Alterations in Rat Intestinal Transit by Morphine Promote Bacterial Translocation", Digestive Diseases and Sciences, vol. 38, No. 8 (1993), pp. 1530-1536.

Salzman et al., "Negative Interactions with the Microbiota: IBD", GI Microbiota and Regulation of the Immune System, Advances in Experimental Medicine and Biology, 2008,vol. 635, Chp. 6, 68-78.

Scher et al., "The Microbiome and Rheumatoid Arthritis", Nat. Rev. Rheumatol. 7, 569-578 (2011).

Schreiner et al., "The "Microflora Hypothesis" of Allergic Disease, GI Microbiota and Regulation of the Immune System", Advances in Experimental Medicine and Biology, 2008, Chp. 10, 114-134.

Zhu et al., "Gut Microbiota and Probiotics in Colon Tumorigenesis", Cancer Letters 309 (2011) 119-127.

\* cited by examiner

Figure 2

| Group | Route of Admin | Formulation | Study Design | # Mice/ Sex-Type | Conc. (mg/mL) | Dose Level mg/kg | Dose Level mL/kg | Day of Admin. | Tissue Collection Time Points Post-Dose |
|---|---|---|---|---|---|---|---|---|---|
| 1 | Not Applicable | NA | Sample prep. (Control) | 6M C57BL/6 RAG1 -/- | NA | NA | NA | NA | Day 8[b]: Immediately post AM dose, tissues and blood collected per text description |
| 2 | Oral (Gavage) | Vehicle | Charcoal Transit | 6M C57BL/6 RAG1 -/- | NA | NA | 10 | 1-8[a] | Day 8: 45 min post AM dose, small intestine collected |
| 3 | Oral (Gavage) | Vehicle | Sample Preparation | 6M C57BL/6 RAG1 -/- | NA | NA | 10 | 1-8[c] | Day 8: Immediately post AM dose, tissues and blood collected per text description |
| 4 | Oral (Gavage) | Oxycodone | Charcoal Transit | 6 M C57BL/6 RAG1 -/- | 1 | 10 | 10 | 1-8[a] | Day 8: 45 min post AM dose, small intestine collected |
| 5 | Oral (Gavage) | Oxycodone/ Naloxone 2:1 (w/w) | Charcoal Transit | 6 M C57BL/6 RAG1 -/- | 1/0.5 | 10/5 | 10 | 1-8[a] | Day 8: 45 min post AM dose, small intestine collected |
| 6 | Oral (Gavage) | Oxycodone | Sample Preparation | 8 M C57BL/6 RAG1 -/- | 1 | 10 | 10 | 1-8[a] | Day 8: Immediately post AM dose, tissues and blood collected per text description |
| 7 | Oral (Gavage) | Oxycodone/ Naloxone 2:1 (w/w) | Sample Preparation | 8 M C57BL/6 RAG1 -/- | 1/0.5 | 10/5 | 10 | 1-8[a] | Day 8: Immediately post AM dose, tissues and blood collected per text description | a. Animals in Groups 2-7 were orally administered the dose three times a day for seven days and once for the eighth day. For Groups 2, 4 and 5 fifteen minutes after the day 8 morning dosing, each mouse was fed a charcoal meal and 30 min following the charcoal meal each mouse was sacrificed and GI tract was collected for charcoal movement measurement.
b. Animals in Group 1 did not receive any treatment or vehicle and were removed from cage and weighed so they get same handling as dosed group
c. For Groups 1, 3, 6 and 7, animals were sacrificed after the first dose on day 8 and blood and tissue samples were collected and measured as described in example 2.

Figure 4

| Phase | Pre-Randomisation | | | Double-Blind | | | | | | | | | | |
|---|---|---|---|---|---|---|---|---|---|---|---|---|---|---|
| Period | Screening | Run-in[1] | | Cross-over Period 1[1] | | | | | | Cross-over Period 2[1] | | | | |
| Study Visit | Visit 1 | Visit 2 | Visit 3 | Visit 4, 5 | Visit 6 | Visit 7 | Visit 8 | Visit 9 | Visits 10, 11 | Visit 12 | Visit 13 | Visit 14 | Visit 15[2] | AE FU[6] |
| Study Day[3] | | | 0 | 2-6 | 7 | 14 | 21 | 24 | 26-30 | 31 | 38 | 45 | 48 | V15+7 |
| Duration | Up to 14 days | 7 to 28 days | | | 3.5 weeks | | | | | | 3.5 weeks | | | 7 days |
| Telephone visit | | | | x | | | | | x | | | | | |
| Investigational site visit at pain management clinic | x | x | x | | x | x | | x | | x | x | | x | x |
| Investigational site visit at gastroenterologist's clinic | | | | | | | x | | | | | x | | |
| Informed Consent (IC) | x | | | | | | | | | | | | | |
| IC for Pharmacogenetic Sampling | x | | | | | | | | | | | | | |
| Assess Inclusion/Exclusion Criteria | x | x | x | | | | | | | | | | | |
| Demography | x | | | | | | | | | | | | | |
| Physical Exam | x | | x | | | | | | | | | | | |
| Vital Signs Measurements | x | | x | | | | | x | | | | | x | |
| Medical History and Current Medical Conditions | x | | | | | | | | | | | | | |
| Assess Prior and Current Medication Use | x | | | | | | | | | | | | | |

Figure 4 cont.

| Phase | Pre-Randomisation | | | | Double-Blind | | | | | | | | | |
|---|---|---|---|---|---|---|---|---|---|---|---|---|---|---|
| Period | Screening | Run-in[1] | | | Cross-over Period 1[1] | | | | | | Cross-over Period 2[1] | | | |
| Study Visit | Visit 1 | Visit 2 | Visit 3 | Visit 4,5 | Visit 6 | Visit 7 | Visit 8 | Visit 9 | Visits 10, 11 | Visit 12 | Visit 13 | Visit 14 | Visit 15[2] | AE FU[6] |
| Study Day[3] | | | 0 | 2-6 | 7 | 14 | 21 | 24 | 26-30 | 31 | 38 | 45 | 48 | V15+7 |
| Duration | Up to 14 days | 7 to 28 days | | | 3.5 weeks | | | | | 3.5 weeks | | | | 7 days |
| Telephone visit | | | | x | | | | | x | | | | | |
| Investigational site visit at pain management clinic | x | x | x | | x | x | | x | | x | x | | x | x |
| Investigational site visit at gastroenterologist's clinic | | | | | | | x | | | | | x | | |
| Clinical Laboratory Tests (hematology, chemistry, urinalysis) | x | | | | | | | x | | | | | x | |
| Blood Sampling for Pharmacogenetic Analysis | | | x | | | | | | | | | | | |
| Pregnancy Test[4] | x (urine) | | | | | | | x (urine) | | | | | x (urine) | |
| 12-lead ECG | x | | | | | | | x | | | | | x | |
| Site Study Staff to Phone Subject | | Approx. every 2 - 4 days | | x | | | | | x | | | | | |
| DoloTest® | x | | x | | x | | | x | | x | | | x | |
| Pain Intensity Scale- "Average Pain over last 24 Hours" (subject) | | Daily in diary | | | | | | | | | | | | |
| Bowel Function Measures (subject)[5] | | Daily in diary | | | | | | | | | | | | |
| OxyIR Pain Rescue Medication Use (subject)[7] | | Daily on medication wallet | | | Daily on medication wallet | | | | | Daily on medication wallet | | | | |
| Bisacodyl Suppository Use (subject)[7] | | Daily on medication wallet | | | Daily on medication wallet | | | | | Daily on medication wallet | | | | |

Figure 4 cont.

| Phase | Pre-Randomisation | | | Double-Blind | | | | | | | | | | |
|---|---|---|---|---|---|---|---|---|---|---|---|---|---|---|
| Period | Screening | Run-in[1] | | Cross-over Period 1[1] | | | | | | Cross-over Period 2[1] | | | | |
| Study Visit | Visit 1 | Visit 2 | Visit 3 | Visit 4, 5 | Visit 6 | Visit 7 | Visit 8 | Visit 9 | Visits 10, 11 | Visit 12 | Visit 13 | Visit 14 | Visit 15[2] | AE FU[6] V15+7 |
| Study Day[3] | | | 0 | 2-6 | 7 | 14 | 21 | 24 | 26-30 | 31 | 38 | 45 | 48 | |
| Duration | Up to 14 days | 7 to 28 days | | 3.5 weeks | | | | | | 3.5 weeks | | | | 7 days |
| Telephone visit | | | | x | | | | | x | | | | | |
| Investigational site visit at pain management clinic | x | x | x | | x | x | | x | | x | x | | x | x |
| Investigational site visit at gastroenterologist's clinic | | | | | | | x | | | | | x | | |
| Bowel Function Index (BFI) (interviewer) | x | x | | | x | x | | x | | x | x | | x | |
| Bristol Stool Form Scale (BSFS) | | | x | | | | | x | | | | | x | |
| Stool sample (microbiota analysis & metabolomics)[8] | | | x | | | | x | | | | | x | | |
| Assess Concomitant Therapy Use | | x | x | | x | x | | x | | x | | | x | x[9] |
| H₂ Breath Test | | | | | | | x | | | | | x | | |
| CH₄ Breath Test | | | | | | | x | | | | | x | | |
| Gastric emptying ($^{13}C$-acetate Breath Test) | | | | | | | x | | | | | x | | |
| Blood sample (immune, inflammatory response parameters, and serum metabolome) | x | | x | | | | | x | | | | | x | |
| Abdominal girth | | | | | | | x | | | | | x | | |

Figure 4 cont.

| Phase | Pre-Randomisation | | | Double-Blind | | | | | | | | | |
|---|---|---|---|---|---|---|---|---|---|---|---|---|---|
| Period | Screening | Run-in[1] | | Cross-over Period 1[1] | | | | | | Cross-over Period 2[1] | | | |
| Study Visit | Visit 1 | Visit 2 | Visit 3 | Visit 4, 5 | Visit 6 | Visit 7 | Visit 8 | Visit 9 | Visits 10, 11 | Visit 12 | Visit 13 | Visit 14 | Visit 15[2] | AE FU[6] |
| Study Day[3] | | | 0 | 2-6 | 7 | 14 | 21 | 24 | 26-30 | 31 | 38 | 45 | 48 | V15+7 |
| Duration | Up to 14 days | 7 to 28 days | | 3.5 weeks | | | | | | 3.5 weeks | | | | 7 days |
| Telephone visit | | | | x | | | | | x | | | | | |
| Investigational site visit at pain management clinic | x | x | x | | x | | | x | | x | x | | x | x |
| Investigational site visit at gastroenterologist's clinic | | | | | | | x | | | | | x | | |
| Adverse Events (Non-elicited Reporting) | | x | x | x | x | x | x | x | x | x | x | | x | x[8] |
| Record subsequent analgesic therapy | | | | | | x | | x | | | | | x | x |
| Randomisation | | | x | | | | | | | | | | | |
| Call IRT to update subject status information | x | x | x | x | x | | | x | x | x | | | x | x |
| Study Medication Dispensed | | x | x | | x | x | | x | | x | x | | | |
| Drug Accountability | | | x | | x | x | | x | | x | x | | x | |
| Subject Diary Dispensed | | x | | | | | | | | | | | | |
| Subject Diary Collection | | | x | | | | | | | | | | x | |
| Discontinuation / End of Study | | | | | | | | | | | | | x | |

COMBINATION OF OXYCODONE AND NALOXONE FOR USE IN TREATING PAIN IN PATIENTS SUFFERING FROM PAIN AND A DISEASE RESULTING IN INTESTINAL DYSBIOSIS AND/OR INCREASING THE RISK FOR INTESTINAL BACTERIAL TRANSLOCATION

FIELD OF THE INVENTION

The present invention relates to an oral pharmaceutical dosage form comprising oxycodone or a pharmaceutically acceptable salt thereof and naloxone or a pharmaceutically acceptable salt thereof for use in the treatment of pain in patients suffering from i) pain and at least one further disease ii) resulting in intestinal dysbiosis and/or at least one further disease iii) increasing the risk for intestinal bacterial translocation resulting inter alia in peritonitis.

BACKGROUND OF THE INVENTION

It has been established over the last years that a number of diseases inter alia affect the intestinal microbiota. An example in this respect is colorectal cancer (Zhu et al., "*Gut microbiota and probiotics in colon tumorigeneses*", Cancer Letters, 2011, Vol. 309, pages 119-127). Further, it is known that a number of diseases increase the susceptibility for bacterial translocation resulting inter alia in peritonitis, (such as e.g. cirrhosis) or in systemic inflammatory response syndrome (SIRS) or sepsis (such as e.g. pancreatitis, cholangitis, burn injury or trauma) (Gatt et a., "*Review article: bacterial translocation in the critically ill—evidence and methods of prevention*", Aliment Pharmacol Ther 25, pages 741-757).

It has further been established that the intestinal microbiota plays an important role in several essential processes in the human body; thus, the microbiota inter alia performs a protective function, a metabolic function and a structural function. An impaired intestinal microbiota may thus result in changes in the metabolic profile, impairment of GI transit and pathogen overgrowth. Treatment regimens for diseases affecting the intestinal microbiota may include the administration of probiotics in order to restore or at least improve the impaired intestinal microbiota.

Patients suffering from a disease resulting in an impaired microbiota or increasing the susceptibility for intestinal bacterial translocation may not only suffer from the underlying disease but also from pain due to various reasons. Thus, a patient suffering from colorectal cancer may also suffer from severe back pain, wherein said back pain may have a completely different origin. The back pain may be that severe that the patient requires a long term analgesic therapy.

Opioids correspond to the most efficient analgesics if moderate to severe pain requires treatment. However, several side effect of opioid therapy are known; one of the most prominent side effects is opioid-induced constipation, which is also affecting the GI-tract.

If one were to treat the above mentioned patient suffering from colorectal cancer and back pain with an opioid, it can be expected that the impaired microbiota will likely not improve but, to the contrary, rather worsen. The same is true for a patient suffering from pain and a disease, which increases the risk for intestinal bacterial translocation; the use of an opioid in such a patient will even further increase the susceptibility to intestinal bacterial translocation. Further, patients suffering from pancreatitis, cholangitis, burn injury or trauma may be more susceptible to bacterial translocation resulting in systemic inflammatory response syndrome (SIRS) or sepsis; the use of an opioid in such patients will even further increase the susceptibility to systemic inflammatory response syndrome (SIRS) or sepsis. As a consequence, opioids may not be used for pain treatment in such patients, resulting in the undertreatment of pain.

It is evident from the above that there is a need for a pharmaceutical composition, which is capable of treating pain in a patient suffering from pain and a further disease, which is negatively affecting the intestinal microbiota and/or increasing the susceptibility for intestinal bacterial translocation (resulting inter alia in peritonitis), wherein the pharmaceutical composition fails to have a negative impact on the intestinal microbiota and may even improve the intestinal microbiota and/or decrease the risk for intestinal bacterial translocation.

OBJECTS AND SUMMARY OF THE INVENTION

The inventors of the present invention surprisingly found that a pharmaceutical dosage form comprising the active agents oxycodone and naloxone is suitable for treating pain in a specific patient population, namely patients suffering from pain and a further disease, which results in intestinal dysbiosis (i.e. a further disease, which is negatively affecting the intestinal microbiota) and/or a further disease, which increases the risk for intestinal bacterial translocation (potentially leading to SIRS, sepsis and/or peritonitis).

In a first object, the present invention is thus directed to a pharmaceutical dosage form for use in the treatment of pain in patients suffering from pain and at least one further disease resulting in intestinal dysbiosis and/or a further disease, which increases the risk for peritonitis.

In a second object, the present invention is concerned with methods of treating pain in a subject suffering from pain and at least one further disease resulting in intestinal dysbiosis and/or a further disease increasing the risk for peritonitis.

Thus, in the most preferred embodiment, the present invention relates to an oral pharmaceutical dosage form comprising oxycodone or a pharmaceutically acceptable salt thereof and naloxone or a pharmaceutically acceptable salt thereof for use in the treatment of pain in patients suffering from i) pain and at least one further disease ii) selected from the group consisting of colorectal cancer, inflammatory bowel disease including Crohn's disease and ulcerative colitis, obesity, autism, irritable bowel syndrome, metabolic syndrome, rheumatoid arthritis, allergy, diabetes mellitus including type 2 diabetes, sepsis, Parkinson's disease, autonomic neuropathy including autonomic neuropathy in type 2 diabetes, scleroderma, achlorhydria, pancreatic exocrine insufficiency, immune-deficiency syndromes, small intestinal obstruction, diverticulitis, fistulae, surgical blind loop, previous ileo-caecal resections, post-radiation enteropathy, small intestinal pseudo-obstruction, small intestinal bacterial overgrowth syndrome, vaginal mycosis, intestinal mycosis, multiple system atrophy, food intolerance, intestinal infections, gallstones and hyperactivity of the immune system, wherein said at least one further disease ii) results in intestinal dysbiosis, and/or at least one further disease iii) selected from the group consisting of cirrhosis, hepatitis, appendicitis, pancreatitis, chronic kidney disease and cholecystitis, wherein said at least one further disease iii) increases the risk for peritonitis.

The wording used above is to be understood in the following meaning, which is to be applied throughout the present specification: an oral pharmaceutical dosage form comprising oxycodone or a pharmaceutically acceptable salt thereof and naloxone or a pharmaceutically acceptable salt thereof for use in the treatment of pain in patients suffering from i) pain and at least one further disease ii) selected from the group consisting of colorectal cancer, inflammatory bowel disease including Crohn's disease and ulcerative colitis, obesity, autism, irritable bowel syndrome, metabolic syndrome, rheumatoid arthritis, allergy, diabetes mellitus including type 2 diabetes, sepsis, Parkinson's disease, autonomic neuropathy including autonomic neuropathy in type 2 diabetes, scleroderma, achlorhydria, pancreatic exocrine insufficiency, immune-deficiency syndromes, small intestinal obstruction, diverticulitis, fistulae, surgical blind loop, previous ileo-caecal resections, post-radiation enteropathy, small intestinal pseudo-obstruction, small intestinal bacterial overgrowth syndrome, vaginal mycosis, intestinal mycosis, multiple system atrophy, food intolerance, intestinal infections, gallstones and hyperactivity of the immune system, wherein said at least one further disease ii) results in intestinal dysbiosis, and/or for use in the treatment of pain in patients suffering from i) pain and at least one further disease iii) selected from the group consisting of cirrhosis, hepatitis, appendicitis, pancreatitis, chronic kidney disease and cholecystitis, wherein said at least one further disease iii) increases the risk for peritonitis.

Thus, there is no link at all between disease ii) and disease iii); rather, a patient may suffer from
i) pain and at least one further disease ii); or
i) pain and at least one further disease iii); or
i) pain and at least one further disease ii) and at least one further disease iii).

In other words, the presence of disease iii) is not an inevitable result of having disease ii).

In a preferred embodiment, the present invention relates to an oral pharmaceutical dosage form comprising oxycodone or a pharmaceutically acceptable salt thereof and naloxone or a pharmaceutically acceptable salt thereof for use in the treatment of pain in patients suffering from i) pain and at least one further disease ii) selected from the group consisting of colorectal cancer, inflammatory bowel disease including Crohn's disease and ulcerative colitis, obesity, autism, irritable bowel syndrome, metabolic syndrome, rheumatoid arthritis, allergy, diabetes mellitus including type 2 diabetes, sepsis, Parkinson's disease, autonomic neuropathy including autonomic neuropathy in type 2 diabetes, scleroderma, achlorhydria, pancreatic exocrine insufficiency, immune-deficiency syndromes, small intestinal obstruction, diverticulitis, fistulae, surgical blind loop, previous ileo-caecal resections, post-radiation enteropathy, small intestinal pseudo-obstruction, small intestinal bacterial overgrowth syndrome, vaginal mycosis, intestinal mycosis, multiple system atrophy, food intolerance, intestinal infections, gallstones and hyperactivity of the immune system, wherein said at least one further disease ii) results in intestinal dysbiosis.

In another preferred embodiment, said at least one further disease ii) is selected from the group consisting of colorectal cancer, obesity, autism, irritable bowel syndrome, metabolic syndrome, rheumatoid arthritis, allergy, type 2 diabetes, sepsis, autonomic neuropathy in type 2 diabetes, scleroderma, achlorhydria, pancreatic exocrine insufficiency, immune-deficiency syndromes, small intestinal obstruction, diverticulitis, fistulae, surgical blind loop, previous ileo-caecal resections, post-radiation enteropathy, small intestinal pseudo-obstruction, small intestinal bacterial overgrowth syndrome, vaginal mycosis, intestinal mycosis, multiple system atrophy, food intolerance, intestinal infections, gallstones and hyperactivity of the immune system.

In another preferred embodiment, said at least one further disease ii) is selected from the group consisting of colorectal cancer, obesity, autism, irritable bowel syndrome, metabolic syndrome, rheumatoid arthritis, allergy, type 2 diabetes, sepsis, autonomic neuropathy in type 2 diabetes, scleroderma, achlorhydria, pancreatic exocrine insufficiency, small intestinal obstruction, diverticulitis, fistulae, previous ileo-caecal resections, post-radiation enteropathy, small intestinal pseudo-obstruction and small intestinal bacterial overgrowth syndrome.

In yet another preferred embodiment, said at least one further disease ii) is selected from the group consisting of colorectal cancer, obesity, autism, irritable bowel syndrome, metabolic syndrome, sepsis and small intestinal bacterial overgrowth syndrome.

In a particularly preferred embodiment, said patient is suffering from i) pain and ii) diverticulitis. In another particularly preferred embodiment, said patient is suffering from i) pain and ii) small intestinal bacterial overgrowth syndrome. In yet another particularly preferred embodiment, said patient is suffering from i) pain and ii) ulcerative colitis. In another particularly preferred embodiment, said patient is suffering from i) pain and ii) colorectal cancer.

In yet another preferred embodiment, the present invention relates to an oral pharmaceutical dosage form comprising oxycodone or a pharmaceutically acceptable salt thereof and naloxone or a pharmaceutically acceptable salt thereof for use in the treatment of pain in patients suffering from i) pain and at least one further disease iii) selected from the group consisting of cirrhosis, pancreatitis, chronic kidney disease and cholecystitis, wherein said at least one further disease iii) increases the risk for peritonitis.

In yet another preferred embodiment, the present invention relates to an oral pharmaceutical dosage form comprising oxycodone or a pharmaceutically acceptable salt thereof and naloxone or a pharmaceutically acceptable salt thereof for use in the treatment of pain in patients suffering from i) pain and at least one further disease iii) increasing the risk for peritonitis, wherein said at least one further disease iii) is selected from the group consisting of cirrhosis, chronic kidney disease and cholecystitis. In a particularly preferred embodiment, said at least one further disease is cirrhosis.

The present invention is in particular directed in the first object to an oral pharmaceutical dosage form comprising oxycodone or a pharmaceutically acceptable salt thereof and naloxone or a pharmaceutically acceptable salt thereof for use in the treatment of pain in patients suffering from i) pain and at least one further disease ii), wherein said at least one further disease ii) results in intestinal dysbiosis, or for use in the treatment of pain in patients suffering from i) pain and at least one further disease iii), wherein said at least one further disease iii) increases the risk for intestinal bacterial translocation. One may also refer to said at least one further disease iii) as increasing the risk for intestinal bacterial translocation resulting in bacteriaemia and leading to sepsis, systemic inflammatory response syndrome (SIRS) and/or peritonitis. Alternatively, one may also refer to said at least one further disease iii) as increasing the risk for intestinal bacterial translocation, wherein said bacterial translocation would then result in peritonitis, systemic inflammatory response syndrome (SIRS) and/or sepsis. In consequence, one may also refer to said at least one further disease iii) as increasing the risk for peritonitis, systemic inflammatory response syndrome (SIRS) and/or sepsis. Said at least one further disease iii), which may also be designated as disease underlying or causing the increased risk for bacterial translocation (and thus for peritonitis, systemic inflammatory response syndrome (SIRS) and/or sepsis), is preferably selected from the group consisting of trauma, burn injury, pancreatitis and cholangitis.

Specific diseases ii) resulting in intestinal dysbiosis and specific diseases iii) increasing the risk for intestinal bacterial translocation are stated below and particularly in the dependent claims of the present application.

In a preferred embodiment, the present invention relates to an oral pharmaceutical dosage form comprising oxycodone or a pharmaceutically acceptable salt thereof and naloxone or a pharmaceutically acceptable salt thereof for use in the treatment of pain in patients suffering from i) pain and at least one further disease ii) selected from the group consisting of diseases linked to the stomach, small intestine, colon, colon and the small intestine, and diseases generally linked to the GI tract, wherein said at least one further disease ii) results in intestinal dysbiosis. The treatment of patients suffering from i) pain and at least one further disease ii) selected from the group consisting of diseases linked to the stomach, small intestine, colon and the small intestine, and diseases generally linked to the GI tract, wherein said at least one further disease ii) results in intestinal dysbiosis, can be preferred. Further, the treatment of patients suffering from i) pain and at least one further disease ii) selected from the group consisting of diseases linked to the stomach, small intestine, and colon and small intestine, wherein said at least one further disease ii) results in intestinal dysbiosis, is preferred. Particularly preferred is the treatment of patients suffering from i) pain and at least one further disease ii) selected from the group consisting of diseases linked to the stomach, and small intestine, wherein said at least one further disease ii) results in intestinal dysbiosis.

In a particularly preferred embodiment, i) pain is not a symptom of the at least one further disease ii) and/or the at least one further disease iii) (i.e. at least one disease selected from the groups as defined above). In this embodiment, the pain is not caused by the at least one further disease ii) or the at least one further disease iii). In other words, the pain is unrelated to the at least one further disease ii) or the at least one further disease iii) and has a different origin.

In other words, another embodiment of the present invention relates to an oral pharmaceutical dosage form comprising oxycodone or a pharmaceutically acceptable salt thereof and naloxone or a pharmaceutically acceptable salt thereof for use in the treatment of pain in patients which otherwise have to totally abstain from opioid-based pain therapy due to the presence of not opioid-induced intestinal dysbiosis as a result of at least one further disease ii) as defined above. Moreover, another embodiment of the present invention relates to an oral pharmaceutical dosage form comprising oxycodone or a pharmaceutically acceptable salt thereof and naloxone or a pharmaceutically acceptable salt thereof for use in the treatment of pain in patients which otherwise have to totally abstain from opioid-based pain therapy since said patients are already at increased risk for intestinal bacterial translocation (resulting inter alia in peritonitis, SIRS and/or sepsis), i.e. particularly susceptible for intestinal bacterial translocation (including susceptibility for peritonitis, SIRS and/or sepsis), as a results of at least one further disease iii) as defined above.

In another preferred embodiment, said intestinal dysbiosis is not induced by an opioid agonist but by said at least one further disease ii); one may also refer to said intestinal dysbiosis as being initially (i.e. prior to the treatment) not induced by an opioid agonist but by said at least one further disease ii).

In another preferred embodiment, said increased risk for intestinal bacterial translocation is not induced by an opioid agonist but by said at least one further disease iii); one may also refer to said increased risk for intestinal bacterial translocation as being initially (i.e. prior to the treatment) not induced by an opioid agonist but by said at least one further disease iii).

Thus, one may also refer to the above patients suffering from i) pain and the at least one further disease ii) and/or the at least one further disease iii) as defined above as opioid-naïve patients.

In a further preferred embodiment, said pain is moderate to severe pain.

In another preferred embodiment, oxycodone or a pharmaceutically acceptable salt thereof and naloxone or a pharmaceutically acceptable salt thereof are the only pharmaceutically active agents comprised in said dosage form.

Further, a co-administration of an active agent directed to the improvement of the intestinal dysbiosis (such as e.g. probiotics) and/or of an active agent directed to the improvement of opioid-induced constipation and/or opioid-induced bowel dysfunction (such as e.g. a laxative) may not be necessary. Thus, the pain treatment regimen in a patient population suffering from i) pain and a disease ii) resulting in intestinal dysbiosis as defined above may exclude the co-administration of an active agent directed to the improvement of the intestinal dysbiosis and/or of an active agent directed to the improvement of opioid-induced constipation and/or opioid-induced bowel dysfunction.

Also, a co-administration of an active agent decreasing the risk for intestinal bacterial translocation (such as e.g. antibiotics) and/or of an active agent directed to the improvement of opioid-induced constipation and/or opioid-induced bowel dysfunction (such as e.g. a laxative) may not be necessary. Thus, the pain treatment regimen in a patient population suffering from i) pain and a disease iii) increasing the risk for intestinal bacterial translocation as defined above may exclude the co-administration of an active agent directed at lowering the risk for intestinal bacterial translocation and/or of an active agent directed to the improvement of opioid-induced constipation and/or opioid-induced bowel dysfunction.

In another preferred embodiment, the dosage form comprises oxycodone or a pharmaceutically acceptable salt thereof in an amount range of equivalent to about 1 mg to about 160 mg oxycodone HCl and naloxone or a pharmaceutically acceptable salt thereof in an amount range of equivalent to about 0.5 mg to about 80 mg naloxone HCl.

The dosage form may preferably comprise oxycodone or a pharmaceutically acceptable salt thereof in an amount of equivalent to about 2.5 mg, to about 5 mg, to about 10 mg, to about 15 mg, to about 20 mg, to about 40 mg, to about 50 mg, to about 60 mg, to about 80 mg, to about 100 mg, to about 120 mg, to about 140 mg, or to about 160 mg oxycodone HCl. Naloxone or a pharmaceutically acceptable salt thereof may be present in an amount of equivalent to about 0.5 mg, to about 1 mg, to about 1.5 mg, to about 2 mg, to about 4 mg, to about 5 mg, to about 10 mg, to about 15 mg, to about 20 mg, to about 40 mg, to about 60 mg, or to about 80 mg naloxone HCl.

In yet another preferred embodiment, the dosage form comprises oxycodone or a pharmaceutically acceptable salt thereof and naloxone or a pharmaceutically acceptable salt thereof in a weight ratio range of from about 6:1 to about 1:1 (oxycodone:naloxone).

In another preferred embodiment, the dosage form comprises oxycodone or a pharmaceutically acceptable salt thereof and naloxone or a pharmaceutically acceptable salt thereof in a 2:1 ratio by weight.

Thus, preferred embodiments relate to dosage forms comprising amounts of equivalent to about 2.5 mg oxycodone HCl and about 1.25 mg naloxone HCl; about 5 mg oxycodone HCl and about 2.5 mg naloxone HCl; about 10 mg oxycodone HCl and about 5 mg naloxone HCl; about 20 mg oxycodone HCl and about 10 mg naloxone HCl; about 40 mg oxycodone HCl and about 20 mg naloxone HCl; about 80 mg oxycodone HCl and 40 mg naloxone HCl; and about 160 mg oxycodone HCl and about 80 mg naloxone HCl.

In another preferred embodiment, the pharmaceutically acceptable salt of the opioid agonist and/or the opioid antagonist is selected from the group comprising the hydrochloride, sulphate, bisulphate, tartrate, nitrate, citrate, bitartrate, phosphate, malate, maleate, hydrobromide, hydroiodide, fumerate and succinate salt. It can be particularly preferred that the salt is the hydrochloride salt.

Furthermore, in an also preferred embodiment, the dosage form may comprise further pharmaceutically acceptable ingredients and/or adjuvants, such as e.g. lubricants, fillers, binders, flowing agents, colorants, flavorants, surfactants, pH-adjusters, anti-tacking agents and/or combinations thereof.

In another preferred embodiment, the dosage form is a prolonged release dosage form.

It can be preferred that the prolonged release dosage form comprises a prolonged release matrix. It can further be preferred that said matrix comprises a fatty alcohol and/or a hydrophobic polymer, preferably an alkylcellulose and more preferably ethylcellulose.

It can also be preferred that the prolonged release dosage form comprises a prolonged release coating.

In a further preferred embodiment, the prolonged release dosage form is an osmotic prolonged release dosage form.

Further, the dosage form according to the present invention may also be an immediate release dosage form.

Preferably, the dosage form according to the present invention is a dosage form selected from the group consisting of a tablet, a capsule, a multi-particulate, a dragée, a granulate and a powder. A particularly preferred dosage form is a tablet or a multi-particulate. Since both active agents, i.e. oxycodone and naloxone, are comprised in a single dosage form, said two active agents are not administered sequentially.

In a second object, the present invention is concerned with a method of treating pain comprising administering an oral pharmaceutical dosage form comprising oxycodone or a pharmaceutically acceptable salt thereof and naloxone or a pharmaceutically acceptable salt thereof to a patient suffering from i) pain and at least one further disease ii) selected from the group consisting of colorectal cancer, inflammatory bowel disease including Crohn's disease and ulcerative colitis, obesity, autism, irritable bowel syndrome, metabolic syndrome, rheumatoid arthritis, allergy, diabetes including type 2 diabetes, sepsis, Parkinson's disease, autonomic neuropathy including autonomic neuropathy in type 2 diabetes, scleroderma, achlorhydria, pancreatic exocrine insufficiency, immune-deficiency syndromes, small intestinal obstruction, diverticulitis, fistulae, surgical blind loop, previous ileo-caecal resections, post-radiation enteropathy, small intestinal pseudo-obstruction, small intestinal bacterial overgrowth syndrome, vaginal mycosis, intestinal mycosis, multiple system atrophy, food intolerance, intestinal infections, gallstones and hyperactivity of the immune system, wherein said at least one further disease ii) results in intestinal dysbiosis, and/or at least one further disease iii) selected from the group consisting of cirrhosis, hepatitis, appendicitis, pancreatitis, chronic kidney disease and cholecystitis, wherein said at least one further disease iii) increases the risk for peritonitis.

In the second object, the present invention is also concerned with a method of treating pain comprising administering an oral pharmaceutical dosage form comprising oxycodone or a pharmaceutically acceptable salt thereof and naloxone or a pharmaceutically acceptable salt thereof to a patient suffering from i) pain and at least one further disease ii), wherein said at least one further disease ii) results in intestinal dysbiosis, or a method of treating pain comprising administering said oral pharmaceutical dosage form to a patient suffering from i) pain and at least one further disease iii), wherein said at least one further disease iii) increases the risk for intestinal bacterial translocation.

All embodiments mentioned above for the first object also apply for the second object of the present invention.

DESCRIPTION OF THE FIGURES

FIG. 2 shows the outline of the group, dosing regimens and study designs used in Example 3.

FIG. 4 lists the schedule of visits and procedures/CRF modules of the study described in Example 4. Procedures in italics will be collected in the CRF/diaries. All procedures (italic and non italic) will be collected in the source documents. The annotations are as follows:

1: Unscheduled visits are allowed during the course of the study if deemed necessary by the investigator. They are mandatory if a subject needs to be titrated for adequate pain control. Vital signs will be recorded as the only mandatory assessment. All other assessments are optional. If ever possible, uptitration (i.e. first intake of higher dose of study medication) should be performed at study site followed by assessments of vital signs.

2: End of Double-blind Phase: completed at the end of Double-blind Phase or as soon as possible after early discontinuation of study medication.

3: The study visit window for Visits 4-7 and Visit 10-13 is ±3 days. The study visit window for Visit 8, 9, 14 and 15 is ±2 days. Further visits to the study site will be conducted if considered necessary for the subject's welfare. The total duration of the Double-blind Phase from V3 to V15 should be 48 days±3 days.

4: Women of childbearing potential must have a negative urine pregnancy test prior to first dose of study medication. As required by the local regulations, more frequent pregnancy tests are permitted.

5: Recorded throughout the day, at the time of occurrence. It includes subject reports of the time point, completeness of bowel movement. The laxative intake will be recorded on the medication wallet. Straining or squeezing is recorded in the run-in period, only.

6: Follow-up visit to record subsequent analgesic therapy and adverse events. This visit may not be done earlier than seven days after the subject's last visit.

7: Rescue medication (bisacodyl suppository and OXY IR) intake will be transferred from the wallet into the CRF by site personnel.
8: A stool sample should be provided up to 3 times within the week preceding to Visit 8 and 14 of Double-blind Phase (i.e. between day 14 (Visit 7) and 21 (Visit 8) in Period 1, and day 38 (13) and 45 (Visit 14) in Period 2), and processed as per instructions by the laboratory.
9: Concomitant therapy will be recorded for any ongoing or new adverse events that require treatment.

Figure 5:
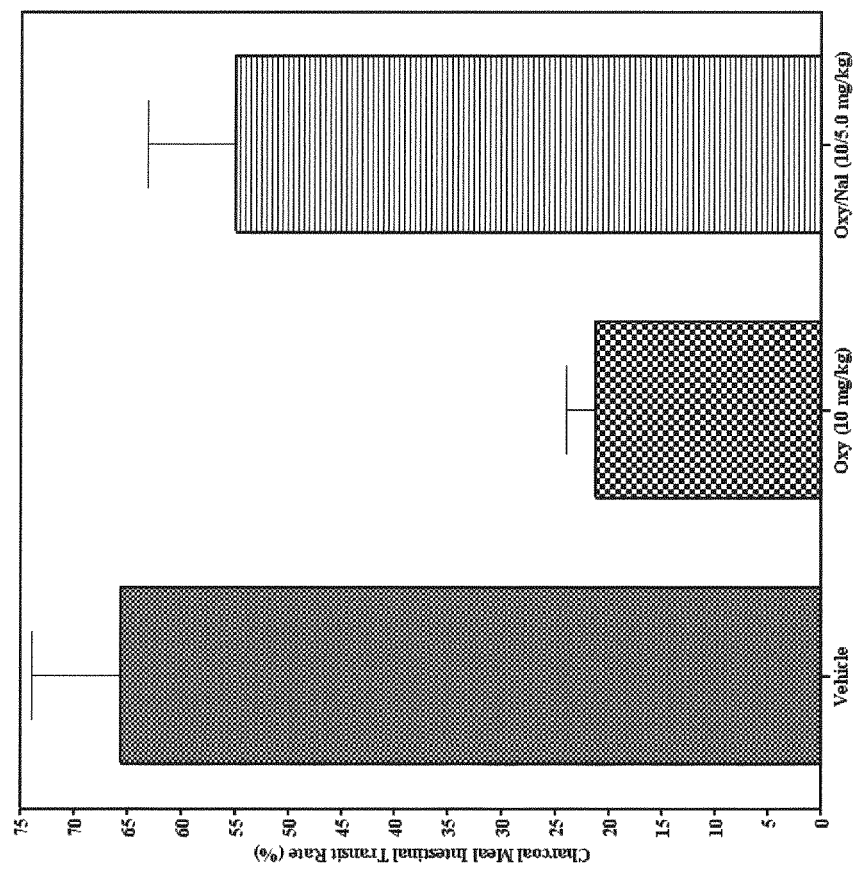

FIG. 5 depicts the transit rates of a charcoal meal administered following multiple oral gavage administrations of i) oxycodone or ii) oxycodone and naloxone in combination to male C57BL/6 RAG1−/−knockout mice (mean±SE). Note: n=6 for Vehicle; n=5 for Oxy (10 mg/kg); n=6 for Oxy/Nal (10/5.0 mg/kg) (see example 3 for further details).

Figure 6:
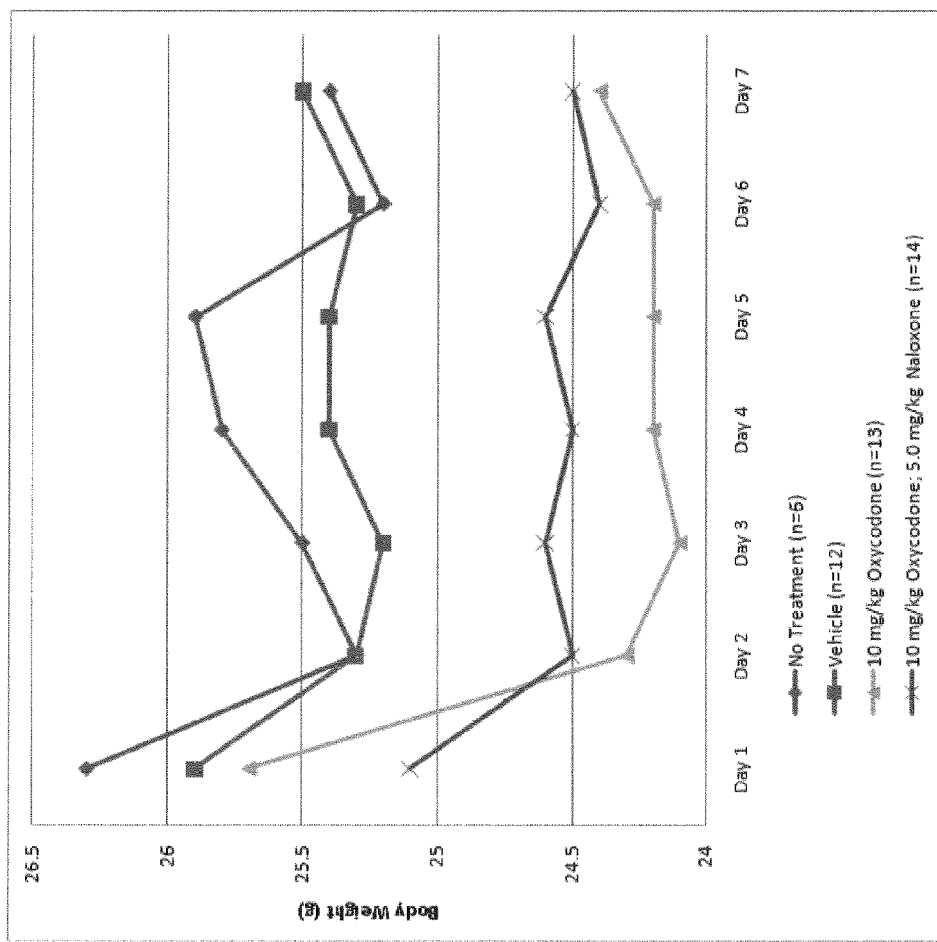

FIG. 6 depicts the mean daily animal body weights. The body weights were recorded as follows: day 1: prior to first dose of the day; days 2-7: after $2^{nd}$ dose of the day (see example 3 for further details).

Figure 7:
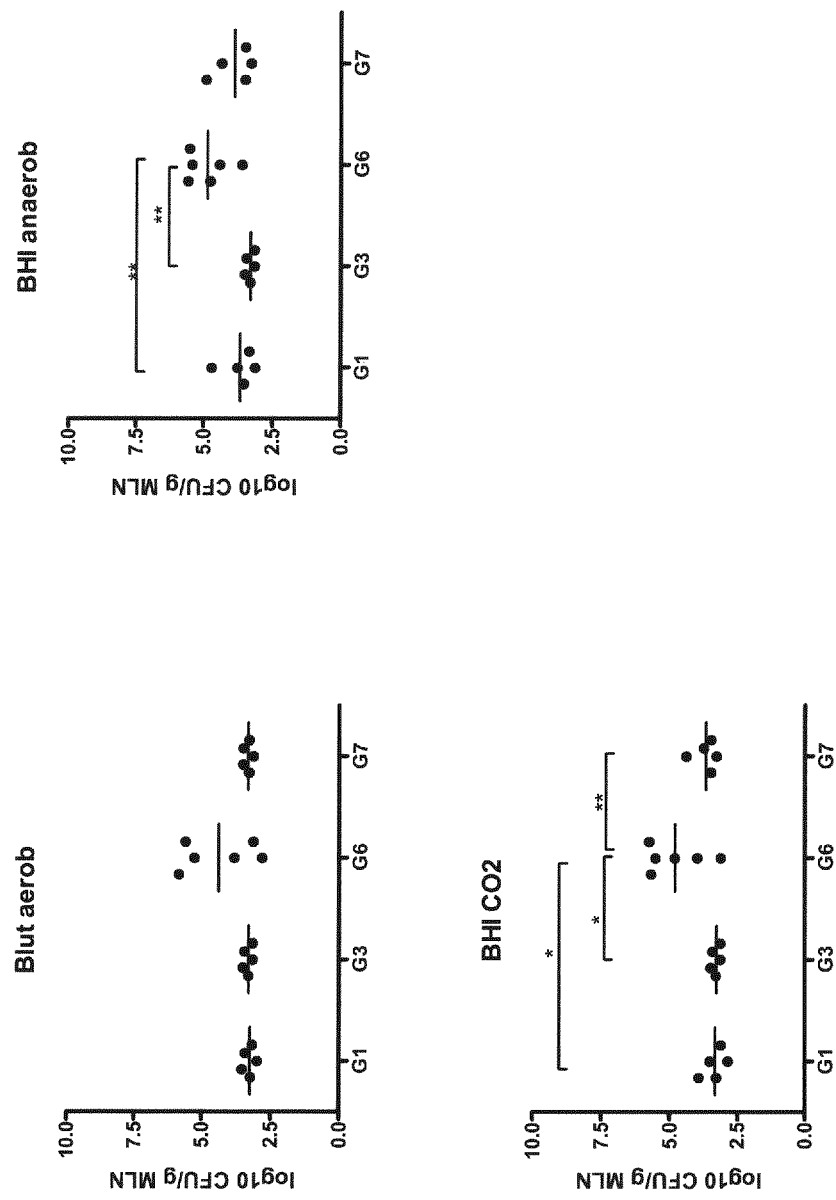

FIG. 7 depicts the colony forming units (CFU) in the mesenteric lymph nodes (MLNs) using different media/agar (blood and BHI [brain-heart-infusion]) under different conditions as stated (aerob=aerobic; anaerob=anaerobic; $CO2=CO_2$) (see example 3 for further details). The abbreviations on the x-axis are as follows:
G1: untreated animals
G3: vehicle-treated animals
G6: oxycodone-treated animals
G7: oxycodone and naloxone-treated animals.

Figure 8:
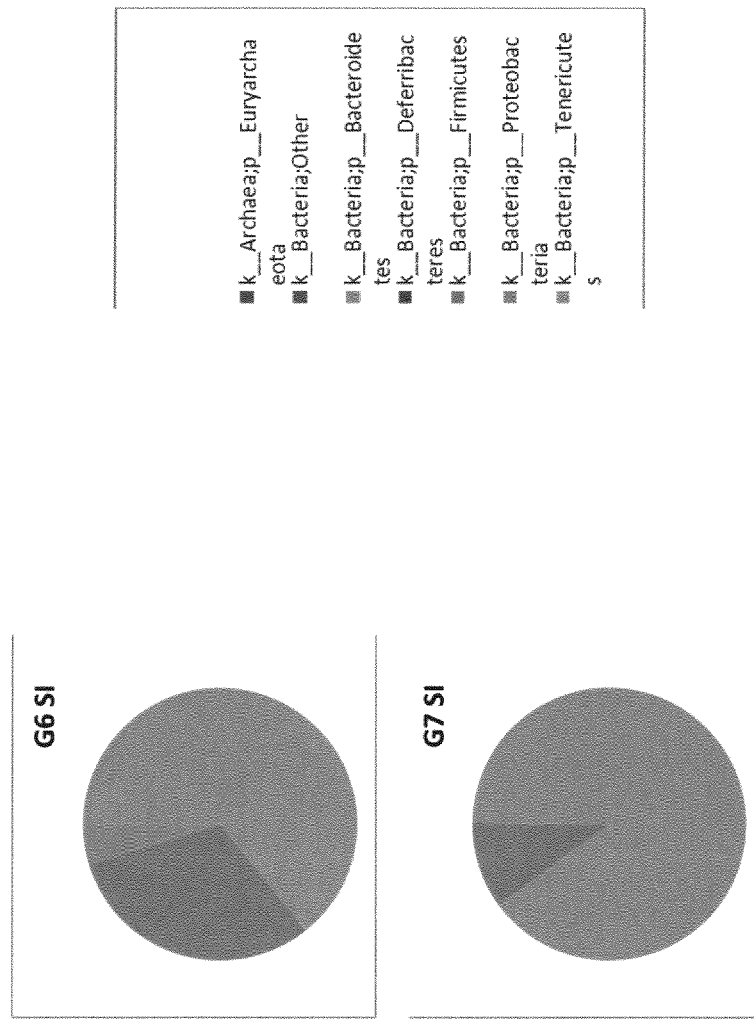

FIG. 8 depicts the phylum levels in the small intestine (SI) of oxycodone-treated animals (G6, n=7) compared to oxycodone and naloxone-treated animals (G7, n=4). The color code for the different phyla is given in the figure (see example 3 for further details).

Figure 9:
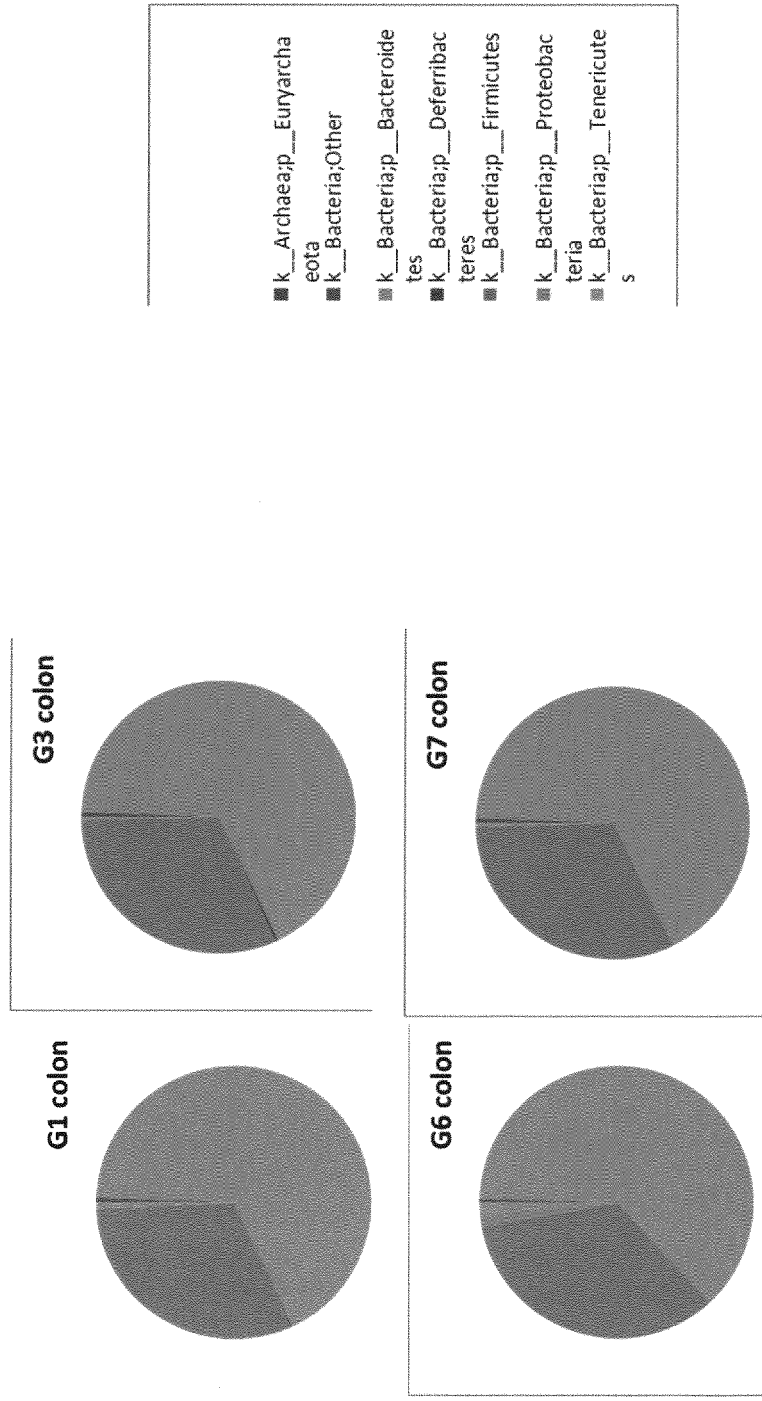

FIG. 9 depicts the phylum levels in the colon of oxycodone-treated animals (G6) compared to oxycodone and naloxone-treated animals (G7), untreated animals (G1) and vehicle-treated animals (G3). The color code for the different phyla is given in the figure (see example 3 for further details).

Figure 10:
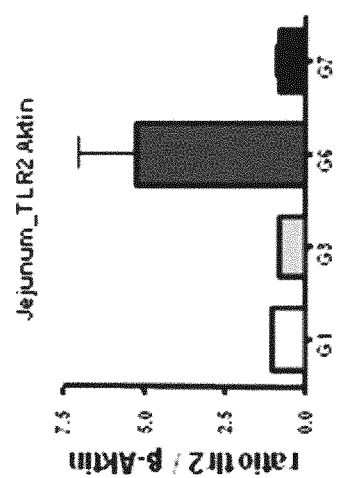

FIG. 10 depicts the results of a quantitative RT-PCR of TLR2 expression in the jejunum, a part of the small intestine. Normalization was carried out to β-actin-expression (see example 3 for further details). The abbreviations on the x-axis are as follows:
G1: untreated animals
G3: vehicle-treated animals
G6: oxycodone-treated animals
G7: oxycodone and naloxone-treated animals.

DETAILED DESCRIPTION OF THE INVENTION

The inventors of the present invention inter alia succeeded in providing a pharmaceutical dosage form for use in the treatment of pain in patients suffering from i) pain and at least one further disease ii), e.g. as defined herein, resulting in intestinal dysbiosis. Further, the inventors were successful in providing a pharmaceutical dosage form, which can be used for pain treatment in patients suffering from i) pain and are particularly susceptible for intestinal bacterial translocation (and thus e.g. peritonitis, SIRS and/or sepsis), e.g. due to at least one further disease iii) as defined herein.

Before some of the embodiments of the present invention are described in more detail, the following definitions are introduced.

Definitions

As used in the specification and the claims, the singular forms of "a" and "an" also include the corresponding plurals unless the context clearly dictates otherwise.

The term "about" in the context of the present invention denotes an interval of accuracy that a person skilled in the art will understand to still ensure the technical effect of the feature in question. The term typically indicates a deviation from the indicated numerical value of ±10% and preferably ±5%.

It needs to be understood that the term "comprising" is not limiting. For the purposes of the present invention, the term "consisting of" is considered to be a preferred embodiment of the term "comprising". If hereinafter a group is defined to comprise at least a certain number of embodiments, this is also meant to encompass a group which preferably consists of these embodiments only.

"Treatment of pain" is to be understood as referring to a general improvement or even cure of the patient's pain or to the alleviation of pain. Such an improvement/cure or alleviation can either be detected by the patient's subjective feeling or by external observations. The intensity of pain may e.g. be assessed using a pain intensity scale; this scale may refer to the average pain over the last 24 hours (Scale of 0-10, 0=no pain; 10=strong pain).

The term "microbiota" is interchangeably used herein with the terms "microbiome" and "(micro)flora" and refers to the totality of microbial cells in the human body, wherein the present invention has a particular focus on the totality of microbial cells in the GI tract or gut. The GI tract is inhabited with $10^{13}$ to $10^{14}$ microorganisms (thought to be 10 times that of the number of human cells in the body and 100 times as many genes as the human genome). The estimated species number varies greatly but it is generally accepted that the adult microbiota consists of greater than 1000 species and more than 700 strains. It is an environment dominated by bacteria, mainly strict anaerobes, but also including viruses, protozoa, archaea and fungi (see introductory part of Grenham et al., "*Brain-gut-microbe communication in health and disease*", Frontiers in physiology, 2011, Vol. 2, Article 94, for further details).

The term "intestinal dysbiosis" means an impaired or altered intestinal microbiota. It may also be described as a shift in the makeup of the commensal microflora to a nonphysiologic composition. This may e.g. mean that obligate bacteria, *Bifidobacteria, Lactobacilli* and *E. coli* (apathogenic) are reduced relative to the normal intestinal microflora, wherein obligate bacteria may partly disappear and *Bifidobacteria* are reduced or almost disappear. Aerobes and *Bacterioids, Clostridia, Streptococci, P. aeruginosa* and other pathogenic bacteria, fungi, mould, lactose-negative enterobacteria and *E. coli* (pathogenic) may be increased relative to the normal intestinal microflora. In Wikipedia, the term "dysbiosis" is defined as follows: "Dysbiosis (also called "dysbacteriosis") refers to microbial imbalance on or inside the body. Dysbiosis is most commonly reported as a condition in the digestive tract. It has been associated with illnesses, such as inflammatory bowel disease, chronic fatigue syndrome, obesity, cancer and colitis. Microbial colonies found on or in the body are normally benign or beneficial. These beneficial and appropriately sized microbial colonies carry out a series of helpful and necessary functions, such as aiding in digestion. They also protect the body from the penetration of pathogenic microbes. These beneficial microbial colonies compete with each other for space and resources and outnumber human cells by a factor 10:1. The term "dysbiosis" is not a standardized medical term. Apparently similar concepts are also described as "microbial imbalance", "bacterial imbalance", or "increased levels of harmful bacteria and reduced levels of the beneficial bacteria"."

"Peritonitis" is used herein in its general meaning, i.e. as corresponding to an inflammation of the peritoneum. "Systemic inflammatory response syndrome (SIRS)" and "sepsis" are used herein in the general meaning, i.e. that SIRS is a clinical syndrome that complicates a noninfectious insult (e.g., acute pancreatitis, pulmonary contusion) and sepsis a clinical syndrome that complicates severe infection, respectively. The patient population suffering from at least one disease as listed herein under disease iii) is particularly vulnerable to developing peritonitis, SIRS and/or sepsis. This means that the patient is not actually suffering from peritonitis, SIRS and/or sepsis but at a higher risk of developing peritonitis, SIRS and/or sepsis than a patient not suffering from at least one of the disease as listed herein under disease iii). The term "risk" and "susceptibility" are used interchangeably herein; "increased risk" or "increased susceptibility" means that patients are prone to a specific disease. The term "increases the risk for peritonitis" may also be understood as "results in a pre-condition of peritonitis" or as "makes the patient susceptible for peritonitis". The term "increases the risk for systemic inflammatory response syndrome (SIRS)" or "sepsis" may also be understood as "results in a pre-condition of SIRS or sepsis" or as "makes the patient susceptible for SIRS or sepsis".

The term "intestinal bacterial translocation" as used herein means that live bacteria and/or its products cross the intestinal barrier. Such a translocation will in almost all cases result in infectious complications. As noted above, specific diseases resulting from an intestinal bacterial translocation are peritonitis, SIRS and sepsis. Thus, the term "increases the risk for intestinal bacterial translocation" may also be understood as "results in a pre-condition of peritonitis, SIRS and/or sepsis" or "makes the patient susceptible for peritonitis, SIRS and/or sepsis".

The term "opioid-naïve patient" means that the patient has not recently taken an opioid on a regular basis.

The term "probiotics" refers to live microorganisms, which, when administered in adequate amounts, confer a health benefit on the host.

"Hyperactivity of the immune system" as used herein comprises one or more of the following: increase of CD3+, CD4+, CD8+ T-cells and activated CD25+, spontaneous proliferation of lymphocytes and increased titer of certain anti-bacterial antibodies, e.g. *E. coli* and *S. aureus* antibodies, increased values of IgA and IgM to gram negative enterobacteria or their endotoxins such as *Hafnia alvei, Pseudomonas aeruginosa, Morganella morganii, Proteus mirabilis, Pseudomonas putida, Citrobacter koseri* and/or *Klebsiella pneumoniae*.

In the context of the present invention, the term "prolonged release" refers to pharmaceutical dosage forms showing a slower release of the active agents than that of a conventional release pharmaceutical dosage forms administered by the same route. Prolonged release is achieved by a special formulation design and/or manufacturing method. In general, "prolonged release dosage forms" in the context of the present invention means that oxycodone and naloxone are released from the pharmaceutical dosage form over an extended period of time.

The term "immediate release" as used herein refers to pharmaceutical dosage forms showing a release of the active substances which is not deliberately modified by a special formulation design and/or manufacturing methods.

"Pharmaceutically acceptable salts" include, but are not limited to, inorganic acid salts such as hydrochloride, hydrobromide, hydroiodide, sulfate, bisulfate, phosphate and the like; organic acid salts such as formate, acetate, trifluoroacetate, malate, maleate, tartrate, bitartrate, fumerate, succinate, citrate and the like; sulfonates such as methanesulfonate, benzenesulfonate, p-toluenesulfonate, and the like; amino acid salts such as arginate, asparginate, glutamate and the like, and metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like.

Detailed Description of the Patient Population and the Oral Dosage Form

The oral pharmaceutical dosage form according to the present invention is intended for treatment of pain in a patient population suffering from i) pain and ii) at least one further disease resulting in intestinal dysbiosis and/or iii) at least one further disease increasing the risk for intestinal bacterial translocation.

A link to intestinal dysbiosis has been established for the following diseases: colorectal cancer (see e.g. Azcarate-Peril et al., "*The intestinal microbiota, gastrointestinal environment and colorectal cancer: a putative role for probiotics in prevention of colorectal cancer?*", Am J Physiol Gastrointest Liver Physiol, 2011, Vol. 301, No. 3, G401-24; Zhu et al., "*Gut microbiota and probiotics in colon tumorigeneses*", Cancer Letters, 2011, Vol. 309, pages 119-127), inflammatory bowel disease including Crohn's disease and ulcerative colitis (see e.g. Salzmann and Bevins "*Negative interactions with the microbiota: IBD*", Adv Exp Med Biol, 2008, Vol. 635, pages 67-78; Rausch et al., "*Colonic mucosa-associated microbiota is influenced by an interaction of Crohn's disease and FUT2 (Secretor) genotype*", 2011, Vol. 108, No. 47, pages 19030-5), obesity (see e.g. Ley et al., "*Obesity alters gut microbial ecology*", PNAS, 2005, Vol. 102, No. 31, pages 11070-11075), autism (see e.g. Grenham et al., "*Brain-gut-microbe communication in health and disease*", Frontiers in physiology, 2011, Vol. 2, Article 94), irritable bowel syndrome (see e.g. O Noor et al., "*Ulcerative colitis and irritable bowel patients exhibit distinct abnormalities of the gut and microbiota*", Gastroenterology, 2010, Vol. 10, No. 134; Ponnusamy et al., "*Microbial Community and metabolomic comparison of irritable bowel syndrome faeces*", Journ Med Microbiol, 2011, Vol. 60, pages 817-827), metabolic syndrome (see e.g. Zhu et al., "*Gut microbiota and probiotics in colon tumorigeneses*", Cancer Letters, 2011, Vol. 309, pages 119-127), rheumatoid arthritis (see e.g. Scher and Abramson, "*The microbiome and rheumatoid arthritis*", Nat Rev Rheumatol., 2011, Vol. 7, No. 10, Pages 569-578), allergy (see e.g. Shreiner et al., "*The 'microflora hypothesis' of allergic disease*", Adv Exp Med Bio, 2008, Vol. 635, pages 113-134), diabetes including type 2 diabetes (see e.g. Larsen et al., "*Gut microbiota in human adults with type 2 diabetes differs from non-diabetic adults*" PLOS ONE, 2010 (February), Vol. 5, No. 2), sepsis (see e.g. Harari et al., "*The effect of morphine on mast cell-mediated mucosal permeability*", 2006, Surgery, Vol. 139, No. 1, pages 54-60; Runkel et al., "*Alterations in rat intestinal transit by morphine promote bacterial translocation*", Dig Diseases and Sciences, 1993, Vol. 38, No. 8, pages 1530-1536), Parkinson's disease (see e.g. Jost, "*Gastrointestinal dysfunction in Parkinson's disease*", J Neurol Scie, 2010, Vol. 289, No. 1-2, pages 69-73), scleroderma, achlorhydria, pancreatic exocrine insufficiency, immune-deficiency syndromes, small intestinal obstruction, diverticulitis, fistulae, surgical blind loop, previous ileo-caecal resections, post-radiation enteropathy, small intestinal pseudo-obstruction, small intestinal bacterial overgrowth syndrome (see e.g. Kopacova, "*Small intestinal bacterial overgrowth syndrome*", 2010, Vo. 16, No. 24, pages 2978-2990 and Quigley E M and Abu-Shanab A, "*Small intestinal bacterial overgrowth*", Infect Dis Clin North Am, 2010, Vol. 24, No. 4, pages 943-59), autonomic neuropathy including autonomic neuropathy in type 2 diabetes (see e.g. Bures et al., "*small intestinal bacterial overgrowth syndrome*", 2010, World J Gastroenterol, Vol. 16, No. 24, pages 2978-2990), vaginal mycosis and intestinal mycosis (see e.g. Achkar and Fries, "*Candida infections of the genitourinary tract*", 2010, clinical microbiology reviews, Vol. 23, pages 253-273), multiple system atrophy, food intolerance, intestinal infections, gallstones and hyperactivity of the immune system.

As mentioned below, dysbiosis is known to affect the upper and mid GI tract including the stomach, the small intestine and the colon. If classified according to the region in the GI tract, achlorhydria is linked to dysbiosis in the stomach, whereas the following diseases are linked to dysbiosis in the small intestine: pancreatic exocrine insufficiency, small intestinal bacterial overgrowth syndrome, small intestinal pseudo-obstruction, surgical blind loop, small intestinal obstruction, scleroderma, food intolerance and hyperactivity of the immune system. The following diseases are linked to dysbiosis in the colon: colorectal cancer, ulcerative colitis, diverticulitis, Parkinson's disease and fistulae, whereas the following diseases are linked to dysbiosis in the colon and the small intestine: Crohn's disease, previous ileo-caecal resection, post-radiation enteropathy, autonomic neuropathy including autonomic neuropathy in type 1 and 2 diabetes, intestinal infections and intestinal mycosis. The following diseases are also linked to dysbiosis, wherein there appears to be no link to a specific region in the GI tract: obesity, autism, metabolic syndrome, rheumatoid arthritis, allergy, diabetes mellitus including type 2 diabetes and sepsis.

Thus, intestinal dysbiosis is present in the above mentioned patient population suffering from i) pain and ii) at least one further disease selected from the diseases outlined above.

The intestinal microbiota carries out important effects such as protective, structural and metabolic effects on the intestinal mucosa. The main functions appear to be the following: a protective function (pathogen displacement, nutrient competition, receptor competition, production of anti-microbial factors), a structural function (barrier fortification, induction of IgA, apical tightening of tight junctions, immune system development) and a metabolic function (control of epithelial cell differentiation and proliferation, metabolism of dietary carcinogens, synthesis of vitamins, fermentation of non-digestible dietary residue and epithelial-derived mucus, iron absorption, salvage of energy).

Intestinal dysbiosis therefore results in an impairment or even complete loss of the above functions and may particularly manifest in changes in the metabolic profile, gas production, impairment of GI transit, epithelial barrier dysfunction, pathogen overgrowth and mucosal immune equilibrium changes.

A patient suffering from at least one disease iii) as defined above is particularly susceptible for increased intestinal bacterial translocation and thus developing peritonitis, SIRS and/or sepsis. Generally, patients with an impaired liver function, e.g. due to cirrhosis or hepatitis, particularly hepatitis B and C, are at higher risk for an increased intestinal bacterial translocation and thus e.g. for peritonitis. This is also the case for patients suffering from chronic kidney disease. A particular patient population being at increased risk for an increased intestinal bacterial translocation and thus e.g. for peritonitis corresponds to patients undergoing peritoneal dialysis, e.g. as a treatment form of chronic kidney disease. Also, patients suffering from an infection in a specific organ, which may spread, are at higher risk for increased intestinal bacterial translocation resulting in peritonitis, SIRS and/or sepsis. Such patients may e.g. suffer from appendicitis, pancreatitis, and cholecystitis. It should be noted that patients suffering from Crohn's disease and diverticulitis, which are listed above under diseases resulting in intestinal dysbiosis, may also be at increased risk for increased intestinal bacterial translocation and thus e.g. may develop peritonitis, SIRS and/or sepsis.

Patients suffering from at least one disease iii) are thus particularly vulnerable to increased bacterial translocation and even a low number of bacterial translocation may suffice to actually induce peritonitis, SIRS and/or sepsis. If such a patient additionally suffers from pain, a pain treatment should be selected, which fails to further increase the risk of peritonitis, SIRS and/or sepsis, e.g. by inducing an increased bacterial translocation.

Efficient pain treatment, particularly treatment of moderate to severe pain, can generally be achieved by the administration of opioid analgesics, such as e.g. morphine or oxycodone. However, the administration of opioid analgesics may result in undesirable side effects, including undesirable side effects in the GI tract. Particularly prominent side effects are opioid-induced constipation (OIC) and opioid-induced bowel dysfunction (OIBD). Further, as inter alia shown herein, the administration of opioid analgesics also negatively affects the intestinal microbiota and results in an increased bacterial translocation.

It is important to note that no correlation or link between OIC or non-opioid induced constipation and intestinal dysbiosis has been established thus far. This is inter alia confirmed e.g. by the definition of the term "dysbiosis" in Wikipedia as recited above, wherein no link between constipation and dysbiosis is made. Rather, constipation is known as developing in the lower GI tract (the colon) only, whereas dysbiosis also affects the upper and mid GI tract including the stomach. Thus, e.g. achlorhydria linked to dysbiosis in the stomach or e.g. pancreatic exocrine insufficiency or small intestinal bacterial overgrowth syndrome linked to dysbiosis in the small intestine are completely unrelated to constipation and no conclusion or transfer can be made from constipation in the colon to any of these diseases. Further, it appears that constipation is not a precondition for intestinal dysbiosis; to the contrary, intestinal dysbiosis may be present without any constipation or even cause constipation.

Since OIC corresponds to a well-known side effect of opioid analgesic therapy, a physician confronted with the above mentioned patient population (in which intestinal dysbiosis is present and/or which is particularly vulnerable to bacterial translocation), will likely be reluctant to administer an active agent, for which a further worsening of a GI parameter, namely constipation, is known. Moreover, opioid analgesic therapy has a further negative impact on the intestinal dysbiosis and increases the risk for bacterial translocation, as shown in the present application and as discussed in the next paragraphs. In consequence, this will result in the undertreatment of pain in such patients since a physician is reluctant to prescribe the administration of e.g. oxycodone alone.

Alternatively, if the physician decides to administer an opioid analgesic in order to treat pain, the additional administration of an active agent alleviating the intestinal dysbiosis appears advisable in order to preemptively counter the further worsening of GI parameters. Such an additional therapy may reside in the administration of probiotics such as e.g. lactic acid bacteria or *Bifidobacteria* to improve dysbiosis. In case of a pain patient being particularly susceptible for peritonitis, the additional administration of an active agent decreasing this susceptibility appears advisable in order to preemptively address a possible peritonitis. Such an additional therapy may reside in the administration of antibiotics. Furthermore, it might even be advisable under the above circumstances to administer an active agent symptomatically counteracting the OIC, such as e.g. a laxative.

Clearly, either the undertreatment of pain or the additional administration of further active agents, which cause further side effects and additional direct or indirect costs (e.g. to treat or manage side effects, costs of additional medication) next to the opioid analgesic is undesirable.

The present inventors have now surprisingly found that the administration of a combination of the opioid agonist oxycodone and the opioid antagonist naloxone solves the above problem: the results of example 3 of the present application inter alia show that the administration of oxycodone alone results in i) a decrease in the body weight, ii) an increased translocation of bacteria into mesenteric lymph nodes, iii) a major change of the microbiome (in this case the bacterial composition) in the small intestine and the colon (wherein the fraction of pathogenic bacteria such as proteobacteria is increased), and iv) an upregulation of TLR2 in the small intestine (determined in the jejunum). All these effects induced by oxycodone are at least partly reversed by naloxone. Thus, as regards i), the decrease of the body weight is clearly not as pronounced if the combination of oxycodone and naloxone is administered; this may be due to differences in the GI microbiome and/or inflammatory reactions in the GI wall induced with oxycodone only. As regards ii), the addition of naloxone completely reverses the increased translocation induced by oxycodone to normal levels. It can be speculated that the effect ii) observed upon administration of oxycodone is linked to the observation iv) above. Thus, an increase in TLR2 activity appears to be involved in mucosal barrier defects that result in increased bacterial translocation into the mesenteric lymph nodes (see also Meng et al., "*Morphine induces bacterial translocation in mice by compromising intestinal barrier function in a TLR-dependent manner*", PLOS ONE, 2013, 8(1): e54040; the authors describe results observed with morphine, see below). The TLR2 levels are not increased upon administration of the combination of oxycodone and naloxone; accordingly, due to the presence of naloxone, TLR2 expression is not increased and, likely linked thereto, no increased bacterial translocation into mesenteric lymph nodes takes place.

Summarizing the above, oxycodone has several negative effects on the microbiome of the GI tract which manifest in or include a decrease in body weight, adverse changes in the microbiome towards pathogenic populations (particularly in the small intestine), and an increased translocation of bacteria into mesenteric lymph nodes (particularly in the small intestine). Particularly the adverse changes of the microbiome together with an impaired mucosal barrier function, both of which are observed upon administration of oxycodone, may result in severe infections ascending from the small intestine. This is of course particularly true if a patient already suffers from a disease negatively influencing the GI tract, i.e. a disease resulting in intestinal dysbiosis or an increased risk in peritonitis. It is noteworthy that studies with morphine in mice and rats also strongly suggest that morphine has a negative effect on the microbiome and the intestinal barrier function (see Meng et al. supra; Nieuwenhuijs et al., "*The role of interdigestive small bowel motility in the regulation of gut microflora, bacterial overgrowth, and bacterial translocation in rats*", Annals of Surgery, 1998, Vol. 228, No. 2, 188-193; Babrowski et al., "*Pseudomonas aeruginosa virulence expression is directly activated by morphine and is capable of causing lethal gut-derived sepsis in mice during chronic morphine administration*", Annals of Surgery, 2012, Vol. 255, No. 2, 386-393).

Thus, the combination is not only effective in counteracting the side effect OIC while maintaining analgesia without any substantial loss in the actual analgesia, but is also suitable for improving intestinal dysbiosis or at least not further worsening intestinal dysbiosis. This is achieved by the presence of naloxone in the combination, which has a positive effect particularly on the intestinal microbiome and results in a restored intestinal barrier function. This positive effect has been discussed above and can inter alia be derived from the results shown in example 3 of the present application.

The actual treatment of pain with a combination of oxycodone and naloxone is thus possible in the patient population with intestinal dysbiosis while the intestinal dysbiosis may even be improved or at least not further worsened; accordingly, the administration of additional active agents would be unnecessary with respect to the improvement of intestinal dysbiosis or OIC. A corresponding pain treatment regime in the patient population as set out above may thus rely on the administration of a dosage form comprising oxycodone and naloxone only.

Further, the combination of oxycodone and naloxone fails to induce an increased bacterial translocation and is thus even suitable for lowering the susceptibility particularly for peritonitis, SIRS and/or sepsis. As noted above, naloxone is responsible for counteracting the negative effect on the intestinal barrier function induced by oxycodone. The combination may thus also particularly be used in pain patients with an increased susceptibility for peritonitis, SIRS and/or sepsis as a prophylactic measure against an actual peritonitis, SIRS and/or sepsis. The administration of additional prophylactic active agents such as antibiotics would thus be unnecessary with respect to the prophylaxis of peritonitis, SIRS and/or sepsis if a combination of oxycodone and naloxone is administered. Pain treatment in a patient population suffering from pain and having an increased risk for intestinal bacterial translocation may thus rely on the administration of a dosage form comprising oxycodone and naloxone only.

More generally, one may thus refer to pain treatment by the combination of oxycodone and naloxone as efficient pain management while improving GI parameters; this not only refers to GI parameters in the lower GI tract, such as e.g. OIC, but also to GI parameters in the upper and mid GI tract (including the stomach and the small intestine), such as e.g. intestinal dysbiosis or an increased risk of bacterial translocation. An analysis of GI parameters in the upper and mid GI tract may inter alia be carried out by a quantitative analysis of intestinal microbiota, the orocaecal transit time, bacterial translocation and gastric emptying or parameters such as e.g. the intestinal and serum metabolome, the abdominal girth, stool consistency (using the Bristol Stool From Scale), immune and inflammatory responses, and correlations between said parameters. For correlation reasons, the analysis of parameters of the lower GI tract, such as e.g. OIC, may be included.

One may thus refer to the combination of oxycodone and naloxone as being suitable for the treatment of pain while not only improving OIC (and consequences of OIC such as hemorrhoids or hemorrhoidal bleeding) but also opioid-induced bowel dysfunction in the upper and mid GI tract. Opioid-induced bowel dysfunction may also be referred to as "GI dysfunction".

Release Behavior of the Dosage Form

In general, the release behavior of a dosage form can inter alia be determined by an in vitro release test.

In this regard, the term "in vitro release" refers to the release rate at which a pharmaceutically active agent, e.g. oxycodone HCl, is released from the pharmaceutical composition when the in vitro release rate is tested by the paddle method according to the European Pharmacopeia as described in the Ph. Eur. 2.9.3 $6^{th}$ edition. The paddle speed is set at 100 rpm in simulated gastric fluid (SGF) dissolution medium with pH 1.2. Aliquots of the dissolution media are withdrawn at the respective time points and analyzed by HPLC with a C18 column, eluted with 30 mM phosphate buffer in acetonitrile (70:70; pH 2.9) with a flow rate of 1.0 ml/min and detected at 220 nm. The term "Simulated Gastric Fluid, pH 1.2" refers to 0.1 N HCl, pH 1.2.

In contrast to an "immediate release", a "prolonged release" dosage form in accordance with the present invention refers to pharmaceutical compositions which release in vitro≤75% (by weight) of the pharmaceutically active agents, namely oxycodone and naloxone, at 45 min.

In the context of the present invention, the term "immediate release" refers to pharmaceutical compositions showing a release of the active substance(s) which is not deliberately modified by a special formulation design and/or manufacturing methods. For oral dosage forms this means that the dissolution profile of the active substance(s) depends essentially on its (theirs) intrinsic properties. Typically, the term "immediate release" refers to pharmaceutical compositions which release in vitro>75% (by weight) of the pharmaceutically active agent(s) at 45 min.

Prolonged release properties may be obtained by different means such as by a coating which is then designated as a prolonged release coating, a matrix which is then designated as a prolonged release matrix or e.g. by an osmotic structure of the pharmaceutical composition.

In order to obtain "prolonged release" properties, one typically uses materials which are known to prolong the release from a dosage form comprising e.g. a prolonged release matrix and/or prolonged release coating. Typical examples are set out further below. The nature of the "prolonged release material" may depend on whether the release properties are attained by a "prolonged release matrix" or a "prolonged release coating". The term "prolonged release materials" thus describes both types of materials. The term "prolonged release matrix material" indicates that a material is used for obtaining a prolonged release matrix. Likewise, the term "prolonged release coating material" indicate that a material is used for obtaining a prolonged release coating.

The term "prolonged release matrix formulation" refers to a pharmaceutical composition including at least one prolonged release material, and at least oxycodone and naloxone as the two pharmaceutically active agents. In a "prolonged release matrix formulation", the "prolonged release materials" are combined with the pharmaceutically active agents to form a mixture from which the pharmaceutically active agents are released over prolonged periods of time, such as e.g. 8, 10, 12, 14, 16, 18, 20, 22 or 24 hours.

It is to be understood that a material will be considered to act as prolonged release material if the dissolution profile of the pharmaceutically active agents is slowed down compared to an immediate or conventional release formulation. If a prolonged release material can be used for manufacturing a prolonged release matrix, it will be considered as a prolonged release matrix material.

Pharmaceutically acceptable excipients which are used to adjust an already prolonged release to a specific profile are not necessarily considered to be prolonged release materials.

It is to be understood that a prolonged release matrix does not necessarily consist only of the pharmaceutically active agents and the prolonged release material. The prolonged release matrix may comprise in addition pharmaceutically acceptable excipients such as fillers, lubricants, glidants, etc. Examples of such excipients are set out below.

The term "prolonged release coating formulation" refers to a pharmaceutical composition including at least one prolonged release material, and oxycodone and naloxone as the two pharmaceutically active agents. In a "prolonged release coating formulation", the "prolonged release materials" are disposed on the pharmaceutically active agents to form a diffusion barrier. Other than in prolonged release matrix formulation, the actives are not intimately mixed with the prolonged release material and the prolonged release coating does not form a three dimensional structure within which the actives are distributed. As the term implies, the prolonged release material forms a layer above the actives. The pharmaceutically active agents are released from a prolonged release coating formulation over prolonged periods of time, such as e.g. 8, 10, 12, 14, 16, 18, 20, 22 or 24 hours.

It is to be understood that a material will be considered to act as prolonged release material if the dissolution profile of the pharmaceutically active agents is slowed down compared to an immediate or conventional release formulation. If a prolonged release material can be used for manufacturing a prolonged release coating, it will be considered as a prolonged release coating material.

Pharmaceutically acceptable excipients which are used to adjust an already prolonged release to a specific profile are not necessarily considered to be prolonged release materials.

When it is mentioned that a prolonged release coating is disposed on pharmaceutically active agents, this is not to be construed as meaning that such a coating will necessarily be directly layered on such active pharmaceutically agents. Of course, if the pharmaceutically active agents oxycodone and naloxone are layered on a carries such as nu-Pareil beads, the coating may be disposed directly thereon.

However, the pharmaceutically active agents may also be first embedded in a polymer layer or e.g. a prolonged release matrix. Subsequently the prolonged release coating may be disposed on e.g. granules which comprise a prolonged release matrix or on tablets which are made from such granules by compression for example.

A pharmaceutical composition with a prolonged release coating may be obtained by combining the pharmaceutically active agents with a carries such as non-Pareil beads and disposing a prolonged release coating on said combinations. Such coating may be made from polymers such cellulose ethers with ethyl cellulose being preferred, acrylic resins, other polymers and mixtures thereof. Such prolonged release coatings may comprise additional excipients such as pore-formers, binders and the like.

It is further to be understood, that the term "prolonged release matrix formulation" does not exclude pharmaceutical compositions with a prolonged release matrix and an additional prolonged release coating being disposed on the matrix. Likewise the term "prolonged release coating formulation" does not exclude pharmaceutical compositions with a prolonged release coating which is disposed on prolonged release matrix.

The term "prolonged release dosage form" refers to the administration form of a pharmaceutical composition of the present invention comprising the two pharmaceutically active agents, i.e. oxycodone and naloxone, in prolonged release form as e.g. in form of a "prolonged release matrix formulation", in the form of a "prolonged release coating formulation", combinations thereof or in other prolonged release formulations such as osmotic formulations. The terms "prolonged release matrix formulation" and "prolonged release dosage form" can be used interchangeably if the prolonged release dosage form consists essentially of the prolonged release matrix formulation. This means that a prolonged release dosage form can comprise in addition to the prolonged release matrix e.g. cosmetic coatings and pharmaceutically acceptable excipients such fillers, lubricants, etc.

For some embodiments, the term "prolonged release matrix dosage form" may indicate that the dosage form comprises a prolonged release matrix as the sole structure being responsible for prolonging the release. This, however, does not exclude that the dosage form may comprise an immediate release portion.

For some embodiments, the term "prolonged release coating dosage form" may indicate that the dosage form comprises a prolonged release coating as the sole structure being responsible for prolonging the release. This, however, does not exclude that the dosage form may comprise an immediate release portion.

The release rates indicated always refer to the formulation such as a monolithic tablet or multi-particulates. The release rates will be chosen such that a pharmaceutical composition can be administered e.g. on a twice a day or once a day basis, i.e. every 12 hours or every 24 hours. Typically, the release will occur by diffusion through the prolonged release matrix and/or coating, erosion of the prolonged matrix and/or coating or combinations thereof.

Release Materials

The following description of suitable materials is to be understood as being not limiting. Rather, the release material may be any material that is known to be capable of imparting prolonged release properties on the active agents, oxycodone and naloxone, when being formulated into a dosage form.

Prolonged Release Matrix Materials

Suitable materials for inclusion in a prolonged release matrix in order to provide a prolonged release matrix dosage form comprising an opioid agonist and an opioid antagonist include:

Hydrophilic or hydrophobic polymers, such as gums, cellulose ethers, acrylic resins and protein derived materials. Of these polymers, the cellulose ethers, especially alkylcelluloses are preferred. The dosage form may conveniently contain between 1% and 80% (by weight) of one or more hydrophilic or hydrophobic polymers;

Substituted or unsubstituted hydrocarbons, such as fatty acids, fatty alcohols, glycerol esters of fatty acids, oils, and waxes. Hydrocarbons having a melting point of between 25 and 90° C. are preferred. The hydrocarbons may be long chain ($C_8$-$C_{50}$, preferably $C_{12}$-$C_{40}$) hydrocarbons. The hydrocarbons may be digestible. The oils and waxes may be vegetable, animal, mineral or synthetic oils and waxes. Of these hydrocarbon materials, fatty (aliphatic) alcohols are preferred. The dosage form may conveniently contain up to 60% (by weight) of at least one digestible, long chain hydrocarbon;

Polyalkylene glycols. The dosage form may suitably contain up to 60% (by weight) of one or more polyalkylene glycols.

In a preferred embodiment, the pharmaceutical dosage forms as described in the present invention will use a diffusion matrix for achieving prolonged release of oxycodone and naloxone from the pharmaceutical dosage form.

To this end, the diffusion matrix may be made from a hydrophobic polymer and/or a $C_{12}$-$C_{36}$ fatty alcohol.

As regards the hydrophobic polymer, use of a hydrophobic cellulose ether and particularly ethyl cellulose may be preferred.

As regards the fatty alcohol, use of lauryl, myristyl, stearyl, cetylstearyl, ceryl and/or cetylalcohol will be preferably considered. The use of stearyl alcohol is particularly preferred.

A particularly preferred embodiment relates to pharmaceutical dosage forms in which the prolonged release properties of oxycodone and naloxone are provided by a diffusion matrix which is made from a hydrophobic polymer such as from ethyl cellulose and a fatty alcohol. The matrices of some of the preferred embodiments of the invention, which may e.g. be made from the aforementioned combination of ethyl cellulose and stearyl alcohol, will be a substantially non-swellable diffusion matrix.

The term "substantially non-swellable diffusion matrix" indicates that the matrix will be substantially non-erosive, i.e. that the size of the matrix will not significantly increase upon contact with fluids. Typically, the volume of a substantially non-swellable diffusion matrix will increase at maximum up to 100%, preferably at maximum up to 75%, more preferably at maximum up to 50%, even more preferably at maximum up to 25% and most preferably at maximum up to 10% or at maximum up to 5% in volume upon contacting an aqueous solution.

Pharmaceutical dosage forms which comprise a hydrophobic polymer with hydrophobic cellulose ethers such as ethyl cellulose being preferred as the sole or one of the components for providing a prolonged release (non-swellable) diffusion matrix, will use an amount of such polymer of between 5 to 20%, preferably of between 6 and 15% by weight and more preferably of between 7 to 10% by weight. The percentages indicate the amount of the matrix-forming material with respect to the total weight of the pharmaceutical dosage form.

Pharmaceutical dosage forms, which comprise a fatty alcohol as the sole or one of the components for providing a prolonged release diffusion matrix, will use an amount of fatty alcohol in the matrix of between 10 to 40%, preferably of between 15 to 35% and more preferably of between 17 to 25% by weight. These percentages again indicate the amount of fatty alcohol based on the total weight of the dosage form.

The person skilled in the art is further aware that such a prolonged release matrix may also contain other pharmaceutically acceptable ingredients and excipients which are conventional in the pharmaceutical art such as lubricants, fillers, binders, flowing agents, colorants, flavorings, surfactants, pH-adjusters, anti-tacking agents and granulating aids. These excipients will typically have no substantial impact on the overall release behavior of the pharmaceutical dosage form.

Typical examples of fillers (diluents) comprise lactose, preferably anhydrous lactose, glucose, saccharose, starch and their hydrolysates, microcrystalline cellulose, cellatose, sugar alcohols such as sorbitol or mannitol, calcium salts like calcium hydrogen phosphate, dicalcium- or tricalcium phosphate. Granulating aids comprise inter alia povidone. Flowing agents and lubricants comprise inter alia highly dispersed silica, talcum, magnesium oxide, calcium stearate, magnesium stearate, sodium stearyl fumarate, fast like hydrated castor oil and glyceryl dibehenate. Binders can include hyproxypropylmethyl cellulose (hypromellose), hydroxypropyl cellulose (HPC), hydroxyethyl cellulose, polyvinyl pyrollidone (povidone), acetic acid vinyl ester (copovidone) and carboxymethycellulose sodium. Anti-tacking agents may include glycerol monostearate. Furthermore, a matrix-based dosage form may e.g. comprise a cosmetic coating.

Prolonged Release Coating Materials

As mentioned above, prolonged release characteristics of a pharmaceutical dosage form may also be achieved by a film coating that governs the release of the active agents from the dosage form. To this end, the pharmaceutical dosage form may comprise a carrier, which is associated with the oxycodone and naloxone. For example, one may use nonpareil beads, sugar beads etc. on and/or into which the pharmaceutically active agents are disposed.

Such active-associated carriers may then be overcoated with a coating that provides prolonged release characteristics. Suitable prolonged release coating materials include hydrophobic polymers such as cellulose ethers and/or acrylic polymer resins. Ethylcellulose may be preferred.

The prolonged release coatings may comprise other components such as hydrophilic substances including hydrophilic polymers such hydroxypropylmethylcellulose (HPMC), polyethylenglycols etc. These components may be used to adjust the prolonged release characteristics of the coatings. In case of e.g. HPMC, the substances may act as pore formers. The coating may, of course, also comprise additional pharmaceutically acceptable excipients, e.g. as set out above for the matrices.

Immediate Release Materials

Typical pharmaceutically acceptable excipients used in immediate release dosage forms are disintegrants, diluents, lubricants, glidants, anti-tacking agents, plasticizers, colorants, flavorants, binders, pH adjusters and the like. These excipients (with the exception of disintegrants) are to be chosen such that they do not substantially alter the immediate release in vitro release rates.

It can be preferred for the pharmaceutical compositions of the present invention to comprise at least a diluent and optionally a disintegrant as pharmaceutically acceptable excipients, particularly if the pharmaceutical compositions of the present invention are provided as a tablet. It can also be preferred for the pharmaceutical compositions of the present invention to comprise at least a disintegrant and optionally a diluent as pharmaceutically acceptable excipients, particularly if the pharmaceutical compositions of the present invention are provided as a tablet. It can further be preferred to use excipients which act both as a disintegrant and a diluent.

The disintegrant, for example, will ensure that the tablet after administration will rapidly disintegrate so that the active agents become readily available for absorption.

Diluents may be selected from but are not limited to lactose such as lactose monohydrate, lactose anhydrous, starch such as maize starch, pregelatinized starch, microcrystalline cellulose, glucose, Mannitol, Maltitol, StarLac® (85% spray dried lactose, 15% maize starch), saccharose, calcium salts like calcium hydrogen phosphate or any combinations of the above.

Disintegrants may be selected from but are not limited to inter alia StarLac® (85% spray dried lactose, 15% maize starch), croscarmellose such as croscarmellose sodium, sodium starch glycolate, crospovidone, alginic acid, or low substituted hydroxypropyl cellulose.

A combination of lactose and starch such as the Starlac® product can be particularly preferred as it combines the properties of a filler and a disintegrant.

Glidants and lubricants may be selected but are not limited to inter alia highly dispersed silica, talcum, magnesium oxide, magnesium stearate, sodium stearyl fumarate etc.

Flowing agents and lubricants comprise inter alia highly dispersed silica, talcum, magnesium oxide, magnesium stearate, sodium stearyl fumarate etc.

If pharmaceutical compositions of the present invention are provided as a tablet, they may be coated for identification purposes with a cosmetic coating. Such coatings will have no substantial impact on the immediate release properties of the pharmaceutical compositions in accordance with the invention.

Preferably, one can use a combination of e.g. starch and lactose as disintegrant. Lactose alone may at the same time function as a filler. A particularly preferred embodiment relies on the product Starlac®, a combination of lactose 85% and starch 15%, which may function both as a disintegrant and as a filler. The combined filler/disintegrant may be comprised within the pharmaceutical composition in an amount of about 40% to about 90%, preferably in an amount of about 50% to about 85% and even more preferably in an amount of about 60% to about 80% by weight based on the weight of the composition. These numbers particularly apply if an excipient having a dual function both as a disintegrant and a filler such as Starlac® is used.

Further particularly preferred embodiments of the present invention are mentioned in the following:

1. Oral pharmaceutical dosage form comprising oxycodone or a pharmaceutically acceptable salt thereof and naloxone or a pharmaceutically acceptable salt thereof for use in the treatment of pain in patients suffering from i) pain and at least one further disease ii) selected from the group consisting of colorectal cancer, inflammatory bowel disease including Crohn's disease and ulcerative colitis, obesity, autism, irritable bowel syndrome, metabolic syndrome, rheumatoid arthritis, allergy, diabetes mellitus including type 2 diabetes, sepsis, Parkinson's disease, autonomic neuropathy including autonomic neuropathy in type 2 diabetes, scleroderma, achlorhydria, pancreatic exocrine insufficiency, immune-deficiency syndromes, small intestinal obstruction, diverticulitis, fistulae, surgical blind loop, previous ileo-caecal resections, post-radiation enteropathy, small intestinal pseudo-obstruction, small intestinal bacterial overgrowth syndrome, vaginal mycosis, intestinal mycosis, multiple system atrophy, food intolerance, intestinal infections, gallstones and hyperactivity of the immune system, wherein said at least one further disease ii) results in intestinal dysbiosis, and/or at least one further disease iii) selected from the group consisting of cirrhosis, hepatitis, appendicitis, pancreatitis, chronic kidney disease and cholecystitis, wherein said at least one further disease iii) increases the risk for peritonitis.
2. Dosage form for use according to 1, wherein said at least one further disease ii) is selected from the group consisting of colorectal cancer, obesity, autism, irritable bowel syndrome, metabolic syndrome, rheumatoid arthritis, allergy, type 2 diabetes, sepsis, autonomic neuropathy in type 2 diabetes, scleroderma, achlorhydria, pancreatic exocrine insufficiency, immune-deficiency syndromes, small intestinal obstruction, diverticulitis, fistulae, surgical blind loop, previous ileocaecal resections, post-radiation enteropathy, small intestinal pseudo-obstruction, small intestinal bacterial overgrowth syndrome, vaginal mycosis, intestinal mycosis, multiple system atrophy, food intolerance, intestinal infections, gallstones and hyperactivity of the immune system, and/or wherein said at least one further disease iii) is selected from the group consisting of cirrhosis, pancreatitis, chronic kidney disease and cholecystitis.
3. Dosage form for use according to 1 or 2, wherein i) pain is not a symptom of the at least one further disease ii) and/or the at least one further disease iii).
4. Dosage form for use according to any one of 1 to 3, wherein said intestinal dysbiosis and/or said increased risk for peritonitis is not induced by an opioid agonist but by said at least one further disease ii) and/or iii).
5. Dosage form for use according to any one of 1 to 4, wherein said pain is moderate to severe pain.
6. Dosage form for use according to any one of 1 to 5, wherein oxycodone or a pharmaceutically acceptable salt thereof and naloxone or a pharmaceutically acceptable salt thereof are the only pharmaceutically active agents comprised in said dosage form.
7. Dosage form for use according to any one of 1 to 6, wherein the pain treatment regimen excludes the co-administration of an active agent directed to the improvement of the intestinal dysbiosis and/or of an active agent decreasing the risk for peritonitis and/or of an active agent directed to the improvement of opioid-induced constipation and/or opioid-induced bowel dysfunction.
8. Dosage form for use according to any one of 1 to 7, wherein the dosage form comprises oxycodone or a pharmaceutically acceptable salt thereof in an amount range of equivalent to about 1 mg to about 160 mg oxycodone HCl and naloxone or a pharmaceutically acceptable salt thereof in an amount range of equivalent to about 0.5 mg to about 80 mg naloxone HCl.
9. Dosage form for use according to any one of 1 to 8, wherein the dosage form comprises oxycodone or a pharmaceutically acceptable salt thereof and naloxone or a pharmaceutically acceptable salt thereof in a 2:1 ratio by weight.
10. Dosage form for use according to any one of 1 to 9, wherein the dosage form is a prolonged release dosage form.
11. Dosage form for use according to 10, wherein the dosage form comprises a prolonged release matrix.
12. Dosage form for use according to 11, wherein the matrix comprises a fatty alcohol and/or a hydrophobic polymer, preferably an alkylcellulose and more preferably ethylcellulose.
13. Dosage form for use according to 10, wherein the dosage form comprises a prolonged release coating.
14. Dosage form for use according to any one of 1 to 9, wherein the dosage form is an immediate release dosage form.
15. Dosage form for use according to any one of 1 to 14, wherein the dosage form is a dosage form selected from the group consisting of a tablet, a capsule, a multiparticulate, a dragée, a granulate and a powder.

EXAMPLES

Example 1

Influence of codeine on the gastrointestinal (GI) microbiota, the GI metagenome (i.e. the whole genetic information of the microbial community) and the host metabolome (i.e. products and/or metabolites produced by the microbial community).

Figure 1:
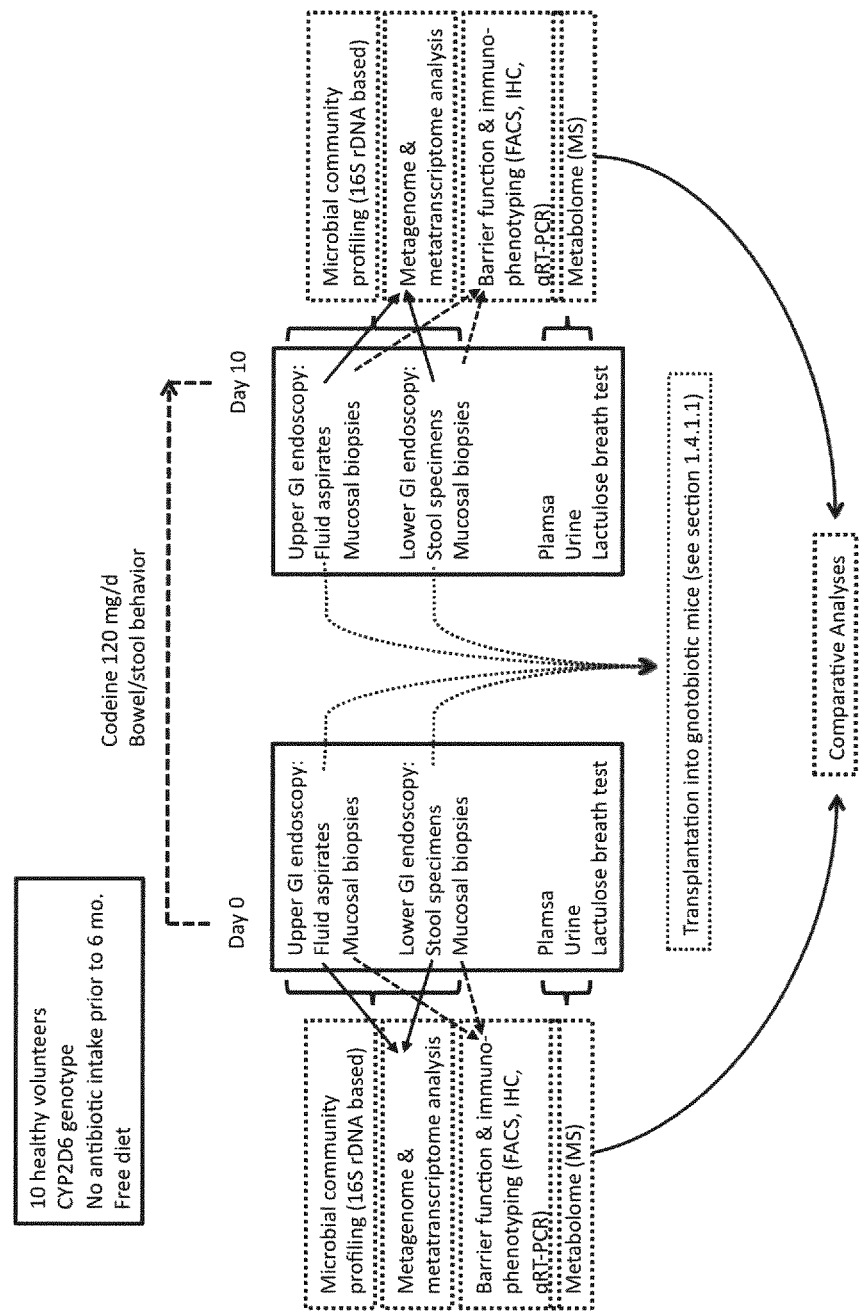
FIG. 1 depicts a graphic of the study design of Example 1.

The main goal of this example resides in the determination of upper and mid GI activity and structural integrity and several GI microbiota parameters including metabolomic parameters of plasma (as a result of bacterial metabolism in the upper/mid GI tract) in healthy subjects comparing the situation prior to and after opioid administration (see also FIG. 1).

Ten healthy volunteers will be recruited and a codeine-dose of 120 mg/d (30 mg four times daily) will be given for ten days. Diet will not be restricted and the bowel/stool behavior will be noted daily by the volunteers. Before the first dose and after the last dose, individuals will undergo upper- and lower-GI tract endoscopy and luminal contents and mucosal biopsies will be taken. Luminal contents will additionally be preserved with glycerol for subsequent transplantation into gnotobiotic mice (see Example 2). Plasma and urine samples will be collected. Volunteers will also undergo a $H_2$ breath test with oral lactulose to assess microbial metabolic activity (especially methane production) and orocoecal transit time. Since bowel preparation for lower GI endoscopy influences the results of $H_2$ breath tests, only a sigmoidoscopy without previous oral lavage will be performed for these experiments.

All of the following objectives are based on the comparison between day 0 and day 10 (see also FIG. 1).

Objective 1: Comparison of the small-bowel microbiota based on comparative 16S rDNA-based microbial community profiling.

Objective 2: Comparative metagenome and metatranscriptome (i.e. the transcriptome of the microbiota) analyses of individual samples (luminal contents only).

Objective 3: Comparative metabolome analyses by assessing the plasma and urine-samples for metabolome signatures based on MS-techniques. The comparison of the metabolome spectra will reveal altered metabolite profiles, which may then be correlated to changes in the individual metagenomes/metatranscriptomes to identify the molecular basis of microbiota caused changes in metabolism.

Objective 4: Assessing the epithelial barrier function of mucosal biopsies and performing a mucosal immune-phenotyping based on IHC and FACS; assessing of selected targets of barrier function (such as e.g. claudins) and the mucosal immune system (pro- vs. anti-inflammatory) based on qRT-PCR.

Objective 5: Transplantation of microbiota into gnotobiotic mice and analysis of gut motility, mucosal barrier function and the mucosal immune-system on the basis of this animal-model.

Example 2

Influence of oxycodone/naloxone on murine gut function, the GI microbiota and the gut-brain axis.

The main goal of this example resides in the determination of GI microbiota parameters and GI structural parameters including impact on local and systemic immune response/inflammation influenced thereby in an animal model comparing the effects of codeine, oxycodone, naloxone and oxycodone/naloxone on said parameters.

C57BL/6 mice (n=10/group) will receive either codeine (40 mg/kg twice daily), oxycodone (10 mg/kg twice daily) or naloxone (15 mg/kg twice daily), alone or in combination, by gavage for 10 days, the readouts being taken during days 8 to 10. A washout experiment will be conducted in which the mice will first be treated with the opioid agonist or antagonist for 10 days, followed by a 20 day washout period, the readouts being taken during days 18 to 20 of the washout period.

Objective 1: After sacrifice, GI specimen (stomach, upper small intestine, lower small intestine, caecum and colon) will be taken and comparative 16S rDNA-based microbial community profiling will be performed.

Objective 2: To test for GI transit time, expulsion of carmine red-stained faeces following transgastric administration of carmine red by gavage will be assessed. Further, to test for mucosal permeability, blood to gut lumen ratio of rhodamine-dextran following intragastric administration of rhodamine-dextran by gavage will be assessed.

Objective 3: To assess the impact of treatment on the gut-brain axis in the different experimental groups, corresponding tests will be performed with the animals: pain sensitivity, anxiety-like behavior, depression-like behavior and activity of the hypothalamus-pituitary-adrenal axis activity. Further, immunological parameters such as spleen weight and plasma levels of cytokines such as IL-6 will be assessed.

Example 3

Effects on intestinal microflora composition and bacterial translocation following multiple oral doses of oxycodone and oxycodone/naloxone combination in male C57BL/6 RAG1 knockout mice.

The main goal of this example resides in the determination of several GI microbiota parameters and GI structural parameters including impact on local and systemic immune response/inflammation in an animal model comparing the effects of oxycodone and oxycodone/naloxone on said parameters to baseline and placebo.

Groups and dosing regimens are depicted in FIG. 2. The objective is to demonstrate differences for the intestinal microflora composition and bacterial translocation between oxycodone and oxycodone/naloxone. To this aim, specified serum, gastrointestinal tract samples and mesenteric lymph nodes were collected according to the protocol as outlined in the following. Further, the intestinal motility was analyzed.

Male mice of the strain C57BL/6 RAG −/− (Taconic Model 4175-M, Taconic Laboratories) with an approximal weight at arrival of 20±7 g at an approximal age of 5 to 10 weeks were used in the present study.

Appropriate amounts of oxycodone and naloxone were dissolved in sterile water to make two dose formulations containing the following nominal concentrations of oxycodone and naloxone: (i) 1 mg/mL Oxycodone and (ii) 1 mg/mL Oxycodone+0.5 mg/mL Naloxone. The formulations were prepared on Day 0 and used for Day 1 to Day 8 dosing. Sterile water was used as vehicle. Each of the two dose formulations was transferred into eight individual sterile vials through sterilization filters, one designated for each day of dosing. The dose formulations were stored refrigerated and protected from light.

Dosing Procedures:

Animals were administered the dose by oral gavage three times a day (~4 hours apart) for 7 days and once on the $8^{th}$ day. Prior to the first dose administration of the day, the dose formulation vials designated for that day were removed from the refrigerator, briefly mixed, and allowed to come to room temperature, where the vials remained throughout the day. After the third dose on day 7, all animals fasted through euthanasia. The dose volume was based on the animal's body weight on Day 1. Dose volume was recorded.

Observation of Animals:
Antemortem Observations

During the post-dose, in-life portion of the study, observation of animals for general health and mortality were performed twice daily (AM and PM) on weekdays and once daily on weekends. During the acclimation period, animals were observed once daily. Only healthy animals were dosed.

Body Weights

Individual body weights were recorded prior to administration of the first dose on Day 1. The body weight determinations prior to Day 1 dose administration was used to determine the dose administered for all subsequent doses. Subsequent body weights were recorded daily after the $2^{nd}$ dose of the day on Days 2 through 7.

Sample Collection:
Groups 2, 4, and 5: Charcoal Test of Intestinal Motility

Fifteen minutes after the eighth day morning dosing, 0.1 mL of charcoal suspension (5% activated charcoal powder, 10% gum Arabic in water) were delivered to the stomach of each mouse using a gavage needle.

Thirty minutes after charcoal delivery, animals were euthanized by an overdose of $CO_2$. The abdominal cavity of each mouse was opened and the edge of the charcoal meal was tied off. The entire small intestine (from the stomach at the pylorus to the caecum) was removed. Its full length and the length of charcoal meal traveled were measured in centimeters. Intestinal transit was expressed as the percentage of intestine length containing the meal, i.e. 100×(pylorus to meal front/pylorus to caecum length). Following measurements, the small intestine was discarded, along with the carcass.

Groups 1, 3, 6, and 7: Serum; Mesenteric Lymph Nodes; Gastrointestinal Tract Luminal Content and Mucosal Scrapings In order to minimize contamination during sample collection, the following measures were invoked:

Sterile tubes (purchased pre-sterilized or autoclaved in-house) were used for all samples.

Samples were collected as soon after euthanasia as possible.

Sterile instruments were used to handle all samples. Instruments were disinfected and/or heat sterilized between each separate sample collection.

All personnel collecting samples wore disposable gloves, as well as sterilized disposable labcoats, shoe covers, masks, and bonnets. Gloves were sprayed with 70% isopropyl alcohol prior to sample collection.

Serum

Immediately after the eighth day dosing, each animal was anesthetized with $CO_2$ and blood (maximum obtainable volume) was collected by cardiac puncture into a syringe. Blood was transferred into centrifuge tubes and allowed to clot at room temperature for a minimum of 5 minutes, after which the blood was centrifuged for 10 min at 10,000 rpm at room temperature. Serum was collected and placed on dry ice prior to storage in a −80° C. freezer. Following blood collection, animals were euthanized via $CO_2$ overdose.

Mesenteric Lymph Nodes (MLNs)

Following euthanasia, the abdomen was opened. The mesenteric root was presented and the mesenteric net unfolded. The mesenteric lymph nodes (MLNs) were removed and surrounding fat was removed. The MLNs were then weighed into sterilized tubes. Following weighing, the MLNs were frozen in liquid nitrogen. Following freezing, the MLNs were placed on dry ice prior to storage in a −70° C. freezer (lymph nodes at −20° C.).

Stomach and Intestine

Following removal of the mesenteric lymph nodes, the gastrointestinal tract (from the stomach through the colon) was removed. The intestine was uncoiled with removal of mesenteric adhesions. The gastrointestinal tract was divided into the following sections: stomach; small intestine; caecum; colon. The stomach was discarded. The small intestine was spread in a meandering pattern and the colon was spread to its length. The small intestine and colon were placed alongside a ruler or similar reference, and photographed separately. The lengths of the small intestine and colon were recorded.

Luminal Contents (Small Intestine, Caecum, Colon)

The small intestine, caecum, and colon were cut longitudinally. The contents of each were individually collected into separate containers with a small spatula or similar instrument, taking care to cause as little injury to the tissue as possible. The weight of the contents collected from each portion was recorded. The weights of the small intestine, caecum, and colon following removal of the contents were also recorded. Collected luminal contents samples were then frozen in liquid nitrogen. Luminal contents samples were then placed on dry ice before transfer to a −80° C. freezer.

Mucosal Scraping (Small Intestine, Caecum, Colon)

A buffer solution for collection, storage, and shipment of collected mucosal scraping samples was prepared: RLT buffer (Qiagen; catalog number 79216) was fortified with 1% beta-Mercaptoethanol (Applichem; catalog number A1108) and thoroughly mixed, then filter sterilized into a sterile RNAse free Eppendorf cup, yielding sterile mucosal scraping buffer solution.

Following removal of the luminal contents from the small intestine, caecum, and colon, the small intestine were divided into the duodenum, jejunum, and ileum. Residual luminal content was removed from the duodenum, jejunum, ileum, caecum, and colon by swaying in phosphate buffered saline (PBS) 10% fetal calf serum (FCS) at approximately 37° C. Following removal of residual luminal contents, an approximately 2 cm length of the mucosa was separated from the remaining tissue by sweeping or scraping along the luminal tissue from proximal to distal using a long thin metal spatula or similar instrument. These mucosal scrapings were collected separately by organ (duodenum, jejunum, ileum, caecum, colon) and weighed into individual sterilized Eppendorf CABE safelock snap-cap tubes or similar containing 350 µL of the prepared sterile mucosal scraping buffer solution. The tubes were closed, vortexed, and the samples frozen in liquid nitrogen. Samples were then placed on dry ice before transfer to a −80° C. freezer. Remaining gastrointestinal tissue was discarded, along with the carcasses.

Read Out: The body weight was assessed daily; for the baseline group and the study end, the following parameters will be determined: length and weight of intestine/intestinal microbiota composition by 16SrDNA (small intestine and caecum)/microbial count in mesenteric lymph nodes (translocation)/concentration of LPS, sCD14, LBP, TNF-α (heart blood)/IL-6, TNFα mRNA expression in mucosal scrapings (small intestine, colon, caecum)/metabolome analysis.

Results:

Charcoal Test of Intestinal Motility

The results of the study relating to GI transit are shown in FIG. 5: the reduction with oxycodone was 67% compared to vehicle and was statistically significant. The reduction of GI transit with the combination of oxycodone and naloxone was 16% compared to vehicle and was not statistically significant. The reduction in GI transit with oxycodone compared to oxycodone/naloxone was statistically significant. The results show that oxycodone delays GI transit over a period of 7.5 days without an indication for tolerance development and that naloxone can reverse this effect.

Body Weights

The results of the body weights over 7 days are shown in FIG. 6. For all groups, a drop in the body weight can be observed starting from day 2, i.e. after start of the dosing. This loss of body weight can primarily be attributed to the stress associated with the repeated handling of all animals. Animals receiving 10 mg/kg oxycodone had the highest average percentage body weight loss, ranging from 1.09% to 9.23% with a mean of 4.17%. Body weight changes for animals receiving the 10 mg/kg oxycodone/5 mg/kg naloxone combination ranged from a gain of 5.96% to a loss of 8.16% with an average of 2.58% loss of body weight. The addition of naloxone thus partly reverses the loss in body weight induced by oxycodone. Differences in the GI microbiome and/or inflammatory reactions present in the mice receiving oxycodone might be responsible for the observed effects.

Analysis of the Mesenteric Lymph Nodes (as Parameter for Bacterial Translocation)

MLNs were obtained as indicated above and the amount of bacteria in the MLNs was analyzed by determining colony forming units (CFUs) per g MLN in different media and under different conditions as indicated in FIG. 7. Contaminated samples were not taken into account (contaminated samples in the different groups: 1 in G1, 1 in G3, 2 in G6 and 3 in G7). The statistical analysis was performed using one way ANCOVA. Increased CFUs in MLNs were determined in the group, where oxycodone was administered (G6, all groups are shown in the overview of FIG. 2).

Analysis of the Contents of the Small Intestine

The contents of the small intestine of the different groups were obtained as described above. The presence and the amount of bacteria of different phyla was then determined in the oxycodone (G6) and in the oxycodone/naloxone (G7) treated groups according to standard methods. The results are shown in FIG. 8, wherein FIG. 8 also shows the color code for the different phyla.

As can be derived from the graph of the G6-group, there is a clear increase in (pathogenic) proteobacteria compared to the G7-group. This increase has thus far not been described as a result of the administration of oxycodone. Further, a clear decrease in bacterioides in the G6-group compared to the G7-group can be observed. Again, such a change has thus far not been described as a result of the administration of oxycodone. Naloxone is capable of reversing these negative changes in the bacterial composition induced by oxycodone.

The results of the small intestine samples are shown in the following on an individual level for the mice of the two different groups (n=7 for G6 [oxycodone only] and n=4 for G7 [oxycodone/naloxone]).

| Mouse | MG6-01 | MG6-02 | MG6-03 | MG6-04 | MG6-06 | MG6-07 | MG6-08 |
|---|---|---|---|---|---|---|---|
| Bacteroidetes | 88.1 | 95.6 | 18.2 | 3.0 | 84.0 | 75.8 | 87.9 |
| Deferribacteres | — | — | 0.1 | — | — | — | — |
| Firmicutes | 11.8 | 4.3 | 64.5 | 96.5 | 12.0 | 22.3 | 11.1 |
| Tenericutes | — | — | — | — | — | — | — |
| Proteobacteria | 0.1 | 0.1 | 17.2 | 0.5 | 3.7 | 1.8 | 0.8 |
| others | — | — | — | — | 0.3 | 0.1 | 0.2 |

As can be derived from the above table, the two mice 03-SI and 04-SI of the G6-group show a completely altered small intestine composition hardly displaying any bacteroidetes but rather firmicutes and also proteobacteria. It is noted that mice 03 SI, 04SI, 06SI, 07SI and 08SI all show a significant amount of proteobacteria (0.5 to 17%). These data suggest that oxycodone can alter the composition of the small intestine microbiome dramatically (2/7) and give yield to pathogenic populations such as proteobacteria (5/7).

| Mouse | MG7-02 | MG7-04 | MG7-06 | MG7-08 |
|---|---|---|---|---|
| Bacteroidetes | 96.7 | 82.5 | 76.3 | 84.8 |
| Deferribacteres | — | — | 1.7 | — |
| Firmicutes | 3.2 | 17.5 | 20.3 | 15.2 |
| Tenericutes | — | — | 1.7 | — |
| Proteobacteria | — | — | — | — |
| others | 0.1 | 0.2 | — | — |

As can be derived from the above table, no completely altered composition was observed upon administration of the oxycodone/naloxone combination. Further, no pathogenic populations such as proteobacteria were detected in the mice treated with the oxycodone/naloxone combination.

Analysis of the Colon

The contents of the colon of the different groups were obtained as described above. The presence and the amount of bacteria of different phyla was then determined in the control [untreated] (G1), the vehicle-treated (G3), the oxycodone-treated (G6) and in the oxycodone/naloxone-treated (G7) groups according to standard methods. The results are shown in FIG. 9, wherein FIG. 9 also shows the color code for the different phyla.

An increase in proteobacteria in the G6-group was observed compared to the remaining groups. The addition of naloxone thus reverses the effect on the microbiome in the colon induced by oxycodone.

Analysis of the Mucosal Scraping of the Jejunum of the Small Intestine: TLR2-Expression The mucosal scraping of the jejunum was obtained as described above and the expression level of the TLR2-mRNA was determined by a quantitative RT-PCR according to standard methods using β-actin mRNA as normalization control. FIG. 10 shows the results of the quantitative RT-PCR, wherein the ratioTLR2/β-actin of the amounts of TLR2 and β-actin is given on the y-axis.

Clearly, TLR2-expression is upregulated in the jejunum in the oxycodone-treated mice, whereas the level of TLR2 is back to normal in the oxycodone/naloxone-treated mice. Naloxone is thus preventing an oxycodone-induced TLR2 upregulation. As can inter alia be derived from the publication by Meng et al., supra, a TLR2 upregulation is supposed to be involved in mucosal barrier defects resulting in bacterial translocation.

Example 4

An exploratory, double-blind, double-dummy, randomized, 2-period, crossover, Phase IIa study to assess the influence of oxycodone/naloxone prolonged release tablets (OXN PR) compared to oxycodone prolonged release tablets (OxyPR) on intestinal microbiota and other gastrointestinal (GI) parameters in subjects suffering from non-malignant pain requiring an equivalent of 20 to 50 mg oxycodone PR per day.

The main goal of this example resides in the comparison of several GI parameters in patients suffering from pain and constipation and being either treated with oxycodone or oxycodone/naloxone. Patients suffering from pain and opioid-induced constipation were chosen since it appears likely that other GI parameters apart from constipation (e.g. the microbiota) may also be altered in these patients and that a comparison of the effects of oxycodone and of oxycodone/naloxone on such other GI parameters may also be carried out and allow an analysis of the potential reversibility if a combination of oxycodone and naloxone is administered.

Objectives of main interest:
- Quantitative analysis of intestinal microbiota as determined in stool samples of subjects treated with OXN PR compared to those treated with OxyPR;
- To assess orocaecal transit time and gastric emptying on the basis of intestinal absorption and intermediary bacterial metabolism as determined by breath tests ($H_2$ breath test, $CH_4$ breath test and $^{13}C$-acetate breath test) in subjects treated with OXN PR compared to those treated with OxyPR.

Further Objectives:
- To explore the impact of OXN PR and OxyPR on the intestinal and serum metabolome by assessing the metabolites and mapping of respective compounds to corresponding metabolic pathways;
- To determine the change in abdominal girth in subjects treated with OXN PR compared to those treated with OxyPR;
- To assess the stool consistency based on the Bristol Stool Form Scale (BSFS) in subjects treated with OXN PR compared to those treated with OxyPR;
- To assess symptoms of constipation in subjects taking OXN PR compared to subjects taking OxyPR as measured by the Bowel Function Index (BFI);
- To assess pain and its impact on a subject's quality of life (QoL) following treatment with OXN PR compared to OxyPR as measured by the DoloTest®;
- To explore the correlation between intestinal microbiota and breath tests in subjects treated with OXN PR compared to those treated with OxyPR;
- To explore the correlation between intestinal microbiota and BFI in subjects treated with OXN PR compared to those treated with OxyPR;
- To explore the correlation between intestinal microbiota and metabolome (mapping of compounds) in subjects treated with OXN PR compared to those treated with OxyPR;
- To determine parameters of immune and inflammatory response in subjects treated with OXN PR compared to those treated with OxyPR, based on the following laboratory parameters: TNFα (tumor necrosis factor alpha), CRP (C-reactive protein), IL-6 (interleukin six), LPS (lipopolysaccharide), LPB (lipopolysaccharide binding protein), sCD 14 (soluble CD 14), GLP-2 (glucagon like protein two);

To explore the correlation between parameters of immune/inflammatory response and breath test results in subjects treated with OXN PR compared to those treated with OxyPR.

Study Design (Methodology):

This study is a multi-centre, exploratory, double-blind, double-dummy, randomized, 2-period, cross-over, Phase IIa study in subjects with severe non-malignant pain requiring a WHO step II/III opioid therapy in a daily dose of 20-50 mg oxycodone PR at randomization. During the Run-in Period subjects prestudy opioid treatment will be terminated and switched to oxycodone PR, which will be titrated to an effective analgesic dose between 20-50 mg/day of OxyPR. Oxycodone immediate release (OxyIR) is permitted as analgesic rescue medication during the study up to a maximum of 6 dosages per day. From Visit 2 (start of Run-in Period) onwards subjects will be allowed to take bisacodyl suppository only as rescue medication for constipation. Subjects will be randomized in a 1:1 ratio to two treatment groups and will receive study medication (either OXN PR or OxyPR). The starting dose is the OxyPR dose the subjects received at the end of the Run-in Period. The Double-blind Phase consists of 2 Periods of 24 days (Period 1: 24 days; Period 2: 24 days) and during each Period subjects will receive study medication. Subjects receiving OXN PR during the first Period will receive OxyPR in the subsequent Period and subjects receiving OxyPR during the first Period will receive OXN PR during the second one. During the Double-blind Phase no titration of the study medication dose is permitted. At the Follow-up Visit (AE-FU), which can be performed as an investigational site visit or telephone visit, safety assessment will be performed.

Figure 3:
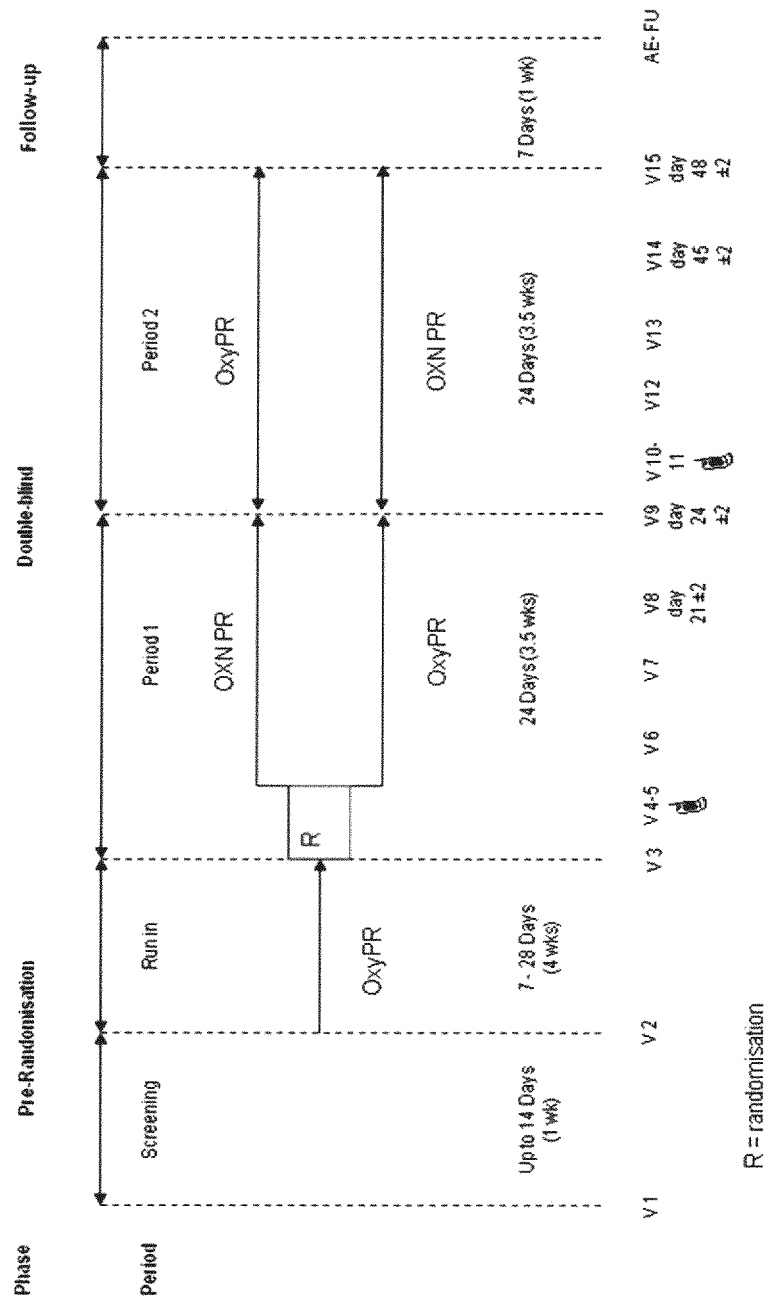
FIG. 3 depicts a graphic of the study design of Example 4.

Study Design: See FIG. 3. FIG. 4 depicts the schedule of visits and procedures.

Number of Subjects: The planned total number is 80 evaluable subjects. With respect to an assumed dropout rate of 20% of subjects, approximately 100 subjects will be randomized in total, and about 120-130 subjects will be screened.

Indication and Criteria for Inclusion/Exclusion:

Inclusion Criteria:
- Male or female subjects of at least 18 years (females less than one year post-menopausal must have a negative serum or urine pregnancy test prior to the first dose of study medication, be non-lactating, and willing to use adequate and highly effective methods of contraception throughout the study);
- Subjects who are receiving WHO step II/III opioid analgesic medication for the treatment of non-malignant pain;
- Documented history of non-malignant pain that requires around-the-clock opioid therapy (20-50 mg oxycodone PR equivalent per day for a minimum of study duration);
- Subjects with constipation caused or aggravated by opioids:
  i) Subject's medical need of regular intake of laxatives to have at least 3 bowel evacuations per week, or having less than 3 bowel evacuations when not taking a laxative;
  ii) In the opinion of the subject and investigator confirm that the subjects' constipation is induced, or worsened by the subjects' prestudy opioid medication (present at Screening).
- Subjects must be willing to discontinue their current opioid analgesic routine;
- Subjects must be willing to discontinue their current laxative regimen and willing to comply with the use of bisacodyl suppository as laxative rescue medication;
- Subjects taking daily natural dietary fiber supplementation are eligible if they can maintain their diet throughout the study, and in the investigator's opinion are willing and able to maintain adequate hydration;
- Subjects willing to remain stable on their routine dietary habit;
- Subjects must be willing and able (e.g. mental and physical condition) to participate in all aspects of the study, including use of medication, completion of subjective evaluations, attending scheduled visits at pain management and gastroenterologist clinics, completing telephone contacts, and compliance with protocol requirements as evidenced by providing written, informed consent;
- In the investigator's opinion the subject's non-analgesic concomitant medications, including those medications for the treatment of depression are thought to be stable, and will remain stable throughout the Double-blind Phase of the study;
- In the investigator's opinion the non opioid analgesic medication dose will remain stable during the Double-blind Phase;
- Subjects, who are dissatisfied (lack of efficacy or unacceptable tolerability) with their current WHO step II/III opioid analgesic medication.

Screening Exclusion Criteria:
- Any history of hypersensitivity to oxycodone, naloxone, related products or other ingredients of the study medication;
- Any contraindication to oxycodone, naloxone, bisacodyl and other ingredients of the study medication;
- Active alcohol or drug abuse and/or history of opioid abuse;
- Subjects with a positive urine drug test at screening visit (Visit 1), which indicates unreported illicit drug use or unreported use of a concomitant medication not required to treat the subjects' medical condition(s);
- Subjects receiving hypnotics or other central nervous system (CNS) depressants that, in the investigator's opinion, may pose a risk of additional CNS depression with opioid study medication;
- Subjects presently taking, or who have taken naloxone and naltrexone ≤30 days prior to the start of the Screening Period;
- Subjects receiving enemas on regular basis within the last 4 weeks prior to the start of the Screening Period;
- Subjects with any situation in which opioids are contraindicated (e.g. severe respiratory depression with hypoxia and/or hypercapnia, paralytic ileus);
- Continuous systemic use of antibiotics and/or steroids within the last 4 weeks prior to the start of the Screening Period;
- Evidence of clinically significant cardiovascular, renal, hepatic, gastrointestinal (e.g. paralytic ileus), or psychiatric disease, as determined by medical history, clinical laboratory tests, ECG results, and physical examination;

Chronic or intermittent pain that results from Fibromyalgia or Rheumatoid Arthritis;

Subjects with uncontrolled seizures or convulsive disorder;

Surgery within 2 months prior to the start of the Screening Period, or planned surgery during the 7-week Double-blind Phase that may affect GI motility or pain;

Subjects suffering from diarrhea;

Subjects suffering from colitis ulcerosa or Morbus Crohn;

Subjects with a diagnosis of a clinically relevant hereditary or acquired autonomic neuropathies;

Subjects with a diagnosis of food intolerance, inflammatory and/or autoimmune diseases;

Subjects with untreated hypothyroidism, Addison's disease, increase of intracranial pressure;

Subjects with known or suspected hereditary fructose intolerance;

Subjects who are unable to perform breath test;

Subjects having abnormal aspartate aminotransferase (AST; SGOT), alanine aminotransferase (ALT; SGPT), or alkaline phosphatase levels (>3 times the upper limit of normal) or an abnormal total bilirubin and/or creatinine level(s) (>1.5 times the upper limit of normal), gamma glutamyl transpeptidase (GGT or GGTP)≥3 times the upper limit of normal;

Subjects who participated in a clinical research study involving a new chemical entity or an experimental drug within 30 days of study entry.

Criteria for Entry to the Double-blind Phase:

Subjects continue to satisfy Screening Inclusion criteria without compromising any of the Exclusion criteria;

Subjects should be on a stable dose of 10, 15, 20 or 25 mg oxycodone PR twice daily on at least 4 consecutive days prior to randomization;

Subjects must rate their pain ("average pain" over the last 24 hours) as ≤4 on 0-10 scale with less than or equal to 2 doses of OxyIR analgesic rescue medication/day for either the last 3 consecutive days or 4 of the last 7 days;

Subjects with a BFI>30 at the randomization visit (Visit 3);

Subjects must have confirmed opioid related constipation, which is defined as having less than 3 CSBMs during the last 7 days of the Run-in Period;

Subjects demonstrate compliance with laxative use (bisacodyl suppository), taking open-label OxyPR and OxyIR, and completing daily diaries;

During the Run-in Period the maximum allowed number of bisacodyl suppository intakes is 4 dosages within the last 7 days of the Run-in Period.

Test Treatment, Dose, and Mode of Administration:

| Double-blind Phase | | | | |
|---|---|---|---|---|
| IMP | Dosage Form | Unit Strength | Dosing Frequency | Mode of Administration |
| Prolonged-release oxycodone/naloxone (OXN PR) | Tablets | 5/2.5, 10/5 and 20/10 mg oxycodone/naloxone combination | q12h | Oral |
| Matched placebo for OxyPR | Tablets | matching placebos for 5, 10 and 20 mg OxyPR tablets | q12h | Oral |

Reference Treatment, Dose, and Mode of Administration:

| Pre-Randomization Run-in Phase (open-label) | | | | |
|---|---|---|---|---|
| IMP | Dosage Form | Unit Strength | Dosing Frequency | Mode of Administration |
| Prolonged release oxycodone (OxyPR) | Tablets | 5, 10 and 20 mg oxycodone | q12h | Oral |

During the Run-in Period dosing is fixed and symmetrical (20, 30, 40 and 50 mg/day OxyPR). The OxyPR dose should be titrated until an effective analgesic dose has been established.

| Double-blind Phase | | | | |
|---|---|---|---|---|
| IMP | Dosage Form | Unit Strength | Dosing Frequency | Mode of Administration |
| Prolonged release oxycodone (OxyPR) | Tablets | 5, 10 and 20 mg oxycodone | q12h | Oral |
| Matched placebo for OXN PR | Tablets | Matching placebos for 5/2.5, 10/5 and 20/10 mg OXN PR tablets | q12h | Oral |

During the Double-blind Phase dosing is fixed and symmetrical (20, 30, 40 and 50 mg/day OxyPR for subjects receiving OxyPR and 20/10, 30/15, 40/20 and 50/25 mg/day for subjects receiving OXN PR). Subjects will start the Double-blind Phase with the OxyPR dose, which they received at the end of the Run-in Period.

Concomitant Medication Including Rescue:

All other medications not prohibited by the protocol and considered necessary for the subject's welfare may be administered and/or continued under the supervision of the investigator.

| Analgesic rescue medication (Run-in Period, Double-blind Phase) | | | | |
|---|---|---|---|---|
| Rescue Medication | Dosage Form | Unit Strength | Dosing Frequency | Mode of Administration |
| Oxycodone immediate release (OxyIR; i.e., OxyNorm ®) | Capsules | 5 mg | q4-6h PRN | Oral |

| Laxative rescue medication (Run-in Period, Double-blind Phase) | | | | |
|---|---|---|---|---|
| Rescue Medication | Dosage Form | Unit Strength | Dosing Frequency | Mode of Administration |
| Bisacodyl | Suppository | 10 mg | q3d PRN | Rectal |

Duration of Treatment and Study Duration:

Pre-randomization Phase:

Screening Period: up to 14 days/Run-in Period: 7 to 28 days

Double-blind Phase:

Period 1: 3.5 weeks (approximately 24 days)

Period 2: 3.5 weeks (approximately 24 days)

AE Follow-up Period: 7 Days

Total Duration: Up to approximately 97 days

Treatment Schedule (Procedure):

Pre-randomization Phase (up to 42 days):

Screening (Up to 14 Days): At Visit 1, after written informed consent is obtained, subjects will undergo complete evaluation for eligibility. Subjects meeting the pre-defined assessment criteria (inclusion/exclusion) may continue the study. A blood sample for genetic analysis will be drawn at Visit 3 from those subjects who voluntarily provide a separate informed consent. Subjects will stay with their prestudy medication until Visit 2.

Run-in Period (7 to 28 Days): At Visit 2, subjects will have their opioid therapy converted to open-label OxyPR, which will be titrated to an effective analgesic dose between 20-50 mg/day of OxyPR. OxyIR will be available as analgesic rescue medication. Subjects will also have their prestudy laxative therapy converted to the study laxative (bisacodyl suppository) to be used per the study routine for constipation during this period (no sooner than 72 hours after their most recent BM as rescue medication for constipation). The 7-day baseline assessment in the Run-In Period will start no sooner than the day of the initial dose conversion to OxyPR.

Double-blind Phase (7 Weeks):

Subjects will be randomised at Visit 3 to OXN PR or OxyPR in a 1:1 ratio. Subjects will start the Double-blind Phase at the same dose of OxyPR that they received at the end of the Run-in Period. Subjects will receive during Period 1 either OXN PR or OxyPR. After approximately 3.5 weeks of treatment subjects will enter Period 2 of the Double-blind Phase, in which the treatment will be switched. Subjects receiving OXN PR in Period 1 will receive OxyPR in Period 2, while Subjects receiving OxyPR in Period 1 will receive OXN PR in Period 2. Double-blind study medication will be administered in a double-dummy manner. Subjects will be permitted to take OxyIR as analgesic rescue; it may be dosed every 4 hours as needed.

Titration of the study medication dose is not permitted during the Double-blind Phase. During the Double-blind Phase subjects will follow the laxative regimen.

Other laxatives, except for regular natural dietary fibre supplementation, will not be permitted. During each crossover period the subject will attend 4 investigational site visits and 2 telephone visits. The subjects will attend the investigational site visits at a pain management clinic 7 (Visit 6 and 12), 14 (Visit 7 and 13) and 24 (Visit 9 and 15) days following the start of each period. Furthermore, 21 days (Visit 8 and 14) following the start of each period the subject will attend a visit at the gastroenterologist site.

Safety Follow-up (7 days): Subjects will be followed up for safety 7 days after receiving the last dose of study medication.

General Guidance for Breath Test:

Subjects are not allowed to eat anything for at least 12 hours prior to the breath test; moreover, they will receive detailed dietary advice to avoid carbohydrates, in particular dietary fibres before the test.

Subjects will not be allowed to drink for at least 2 hours prior to the test; on the morning of the study day, small amounts of acaloric fluids are allowed.

Subjects are not allowed to take metoclopramide and domperidone the day before and the morning of breath test;

Laxatives (bisacodyl suppository, enema) should not be taken one day before and the morning of the breath test;

Bowel lavage (e.g. colonoscopy) should be avoided 1 week before the test.

Criteria for Evaluation

Analysis Populations:

Enrolled Population—The enrolled population is defined as all subjects who signed informed consent;

Full Analysis Population—The full analysis population is defined as all randomized subjects who receive at least one dose of IMP and have at least one post-baseline endpoint;

Run-in Period Safety Population—The safety population is defined as all subjects who receive at least one dose of study medication in Run-in Period;

Double-blind Safety Population—The safety population is defined as all randomized subjects who receive at least one dose of IMP in Double-blind Phase.

Parameters of Main Interest:

Intestinal Microbiota Analysis: For each subject stool samples will be collected during the week prior to randomization, between Visit 7 and 8 during Period 1, and between Visit 13 and 14 during Period 2. The effect of OXN PR and OxyPR on intestinal microbiota will be explored. 16S rRNA based deep-sequencing technique will be used for the quantitative gene expression analysis to examine the diversity of gut microbiota targeting specific bacterial phylogenetic groups (phylum-level classification) and selected species (genus or species-level classification). Analyses will be performed for the following bacterial groups/individual bacteria: *Bacteroides* (*B. vulgates* or *B. fragilis*), *Bifidobacteria*, *Enterococci*, *Escherichia coli*, *Lactobacilli*, *Clostridia* (*C. perfringes*, *C. difficile*) and *Eubacteria*.

Combined Measurement of Orocaecal Transit Time and Gastric Emptying:

Lactulose—$H_2$ breath test: Lactulose is a synthetic disaccharide which cannot be hydrolyzed and absorbed in human small intestine. It is fermented by the colonic bacterial flora producing acids, water and gases ($H_2$, $CH_4$, $CO_2$ etc.). Appearance of $H_2$ (or $CH_4$) in alveolar gas (expired air) after ingestion of lactulose reflects that lactulose has reached the cecum and has been fermented by the colonic anaerobic bacteria. Thus, the lactulose-$H_2$-breath test is used as a marker/measure of orocecal transit time. Early ascent of $H_2$ in alveolar gas indicates accelerated orocecal transit usually associated with increased small bowel motility. However, it can also be the result of small intestinal bacterial overgrowth (SIBO). Retarded increase in $H_2$ concentration in the alveolar gas usually indicates decreased small intestinal motility resulting in prolonged orocaecal transit time.

$CH_4$-breath test (based on lactulose—$H_2$ breath test): $CH_4$ is produced by methanogenic colonic flora instead of $H_2$ producing bacteria in colon. Therefore measurement of $CH_4$ along with $H_2$ concentration in alveolar air will enhance the accuracy and reliability of lactulose—$H_2$ breath test. $CH_4$ appears to slow down intestinal transit time and its production is associated with constipation as symptom.

$^{13}$C-acetate breath test (gastric emptying of liquids): Once $^{13}$C-acetate passes from the stomach, it is absorbed in the duodenum and metabolized in the liver forming $^{13}$C-carbon dioxide ($^{13}CO_2$) which is exhaled rapidly. Appearance of $^{13}$C in breath $CO_2$ reflects the rate of gastric emptying of liquid and semi solid food.

To determine the effect of OXN PR and OxyPR on gastric emptying and orocecal transit time a combined breath test with lactulose and $^{13}$C-acetate will be performed at investigational site visits (Visit 8 and 14) at gastroenterologist's clinic. Following an overnight fast, breath samples will be collected before and after the ingestion of a solution containing 10 g lactulose, 150 mg $^{13}$C-acetate and 15 g glucose in 200 ml water. The time of a predefined increase in breath $H_2$-concentration will serve as marker of orocecal transit time. In patients who do not exhale $H_2$ (2-5% of population), $CH_4$ exhalation will serve to estimate orocecal transit time. Based on the kinetics of appearance of $^{13}C$ in breath $CO_2$, rate of gastric emptying will be estimated. Moreover, small bowel transit time will be calculated by subtracting gastric emptying time from orocecal transit time.

Further Parameters:

Intestinal Metabolomics: For each subject stool samples will be collected during the week prior to randomization, between Visit 7 and 8 during Period 1, and between Visit 13 and 14 during Period 2 (same stool samples will be used as for microbiota analyses). The effect of OXN PR and OxyPR on intestinal metabolome will be explored. Metabolomic technology will be used to assess the biochemical composition of intestine based on metabolite assessment and mapping of respective compounds to corresponding metabolic pathways.

Serum Metabolomics: For each subject blood samples will be collected at Visit 1, 9 and 15. The effect of OXN PR and OxyPR on serum metabolome will be explored. Metabolomic technology will be used to assess the biochemical composition of the serum based on metabolite assessment and mapping of respective compounds to corresponding metabolic pathways.

Abdominal Girth: Abdominal girth of each patient will be measured before and 2 hours after the ingestion of test meal at Visit 8 and Visit 14. Any change in the buildup of intestinal gas, abdominal distension and bloating in subjects receiving OXN PR or Oxy PR will be determined. Abdominal girth will be measured as distance around the abdomen at the level of navel (belly button).

Stool Consistency: Stool consistency will be assessed at randomization (Visit 3), and end of Period 1 (Visit 9) and Period 2 (Visit 15) of Double-blind Phase.

Subjective Assessment of Constipation: This will be measured by BFI, a validated scale for the assessment of opioid-induced constipation. BFI will be measured at Screening (Visit 1), start of Run-in Period (visit 2), randomization (Visit 3), and Visit 6, 7, 9, 12, 13 and 15. BFI will be the mean of the following items (assessed at each visit): Ease of defecation (numerical analogue scale [NAS], 0=easy/no difficulty; 100=severe difficulty), Feeling of incomplete bowel evacuation (NAS, 0=not at all, 100=very strong), Personal judgment of constipation (NAS, 0=not at all, 100=very strong).

DoloTest®: DoloTest® is a validated visual health related (HR) QoL measurement tool used in pain patients providing subjective pain assessment and its impact on QoL. The test is composed of 8 domains represented by 8 Visual Analogue Scale (VAS) lines arranged in a radar plot. The radar plot shape of the test provides a graphical presentation of the test called DoloTest® Profile. The VAS lines are used to score the corresponding domains including pain. Addition of each scored domain provides a sum score called DoloTest® Score. To compare the impact of pain on QoL in subjects treated with OXN PR compared to those treated with Oxy PR, DoloTest® will be conducted at Screening (Visit 1), randomization (Visit 3), and end of Period 1 (Visit 9) and Period 2 (Visit 15) of Double-blind Phase.

Intestinal Microbiota and GI Parameters (Breath Tests) Correlation: The results of intestinal microbiota analysis will be correlated with the results of breath tests in an exploratory manner. The result of OXN PR and OxyPR treatments will be compared.

Intestinal Microbiota and BFI Correlation: The results of intestinal microbiota analysis will be correlated with the results of BFI in an exploratory manner. The result of OXN PR and OxyPR treatments will be compared.

Intestinal Microbiota and Metabolome Correlation: The results of intestinal microbiota analysis will be correlated with the results of intestinal metabolome analysis in an exploratory manner. The result of OXN PR and OxyPR treatments will be compared.

Immune and Inflammatory Response Parameters (Microbiota Correlation): For each subject blood samples will be collected at Screening (Visit 1), Visit 9 and Visit 15. To compare the effect of OXN PR with OxyPR serum level of following parameters will be estimated: TNFα (acts as inflammatory mediator in acute-phase, produced by macrophages), CRP (a classical acute-phase protein synthesized by the liver in response to factors released by fat cells), IL-6 (acute-phase cytokine produced by T cells and macrophages), LPS (plasma endotoxin and major component of the cell wall of gram-negative bacteria), LBP (acute-phase protein produced mainly by hepatocytes), sCD14 (CD14 exists in two forms, a membrane fixed CD14 (mCD14) glycophosphatidylinosital anchored protein also found on the surface of human intestinal epithelial cell lines (Funda D P, 2001) and a soluble form (sCD14). mCD14 acts as a receptor for LPS (endotoxin)-LBP (septin)-complex and the presence of LPS in blood increases synthesis of mCD14 in that region. Apart from protease-mediated shedding from leucocytes, sCD14 is also produced by hepatocytes (Matsuura K 1994; Fearns C, 1995; Liu S, 1998; Su G L, 1999; Pan Z, 2000; Bas S, 2004), which represents the major source of acute-phase protein (Baumann H, 1994). Synthesis of sCD 14 in the liver is regulated by IL-6 (Dinarello C A, 1984; Baumann H, 1987), IL-1β (Dinarello C A, 1984; Baumann H, 1990), TNFα (Perlmutter D H, 1986), and glucocorticoids (dexamethasone) (Baumann H, 1987; Gabay C, 1999). sCD 14 can interact directly with T and B cells (Arias M A, 2000; Rey Nores J E, 1999) leading to immune and/or inflammatory response. [LPS, LBP and sCD14 are described as 'signs of endotoxin-signaling cascade activation'], GLP-2 (GLP-2 is secreted by enteroendocrine cells in a nutrient dependent-manner (Orskov C, 1987; Brubaker P L, 1997). It is trophic to the intestinal mucosa, reduces epithelial permeability, and decreases meal-stimulated gastric acid secretion and gastrointestinal motility (Drucker D J, 2002, online 2007)).

Immune and Inflammatory Response Parameters and GI Parameters (Breath Tests) Correlation: There is evidence that gastric emptying is impaired in patients with inflammatory bowel disease and diverticulitis (Keller J, 2009). The results of immune and inflammatory parameters will be correlated with the results of breath tests in an exploratory manner. The result of OXN PR and OxyPR treatments will be compared.

Safety Assessments: Safety will be assessed by documentation of adverse events (AEs), clinical laboratory results, vital signs, physical examinations, electrocardiograms (ECGs).

Statistical Methods:

Efficacy Analyses: All parameters will be analyzed in a descriptive/exploratory manner. Statistics including 95% CI by treatment will be provided. At least for the parameters of main interest an ANCOVA with treatment, period and/or sequence factors will also be performed.

Safety Analyses: The number and percentage of subjects reporting AEs will be summarized by treatment group. In addition, AEs by severity, AEs by relationship to study medication, AEs leading to discontinuation from the study, and serious AEs will be summarized. AE rates in relation to study day, e.g. cumulative incidence, will also be summarized. Clinical laboratory parameters and vital signs will be summarized descriptively. The frequency of laboratory and vital signs results with respect to normal ranges will also be presented.

Sample Size Rationale:

The sample size of 80 evaluable subjects was not statistically estimated as this study serves as an exploratory hypothesis generating study, but this sample size is considered as providing sufficient evidence from clinical point of view.

The invention claimed is:

1. A method for the treatment of pain in a patient suffering from pain and diverticulitis, comprising administering to said patient an oral pharmaceutical dosage form comprising:
    oxycodone or a pharmaceutically acceptable salt thereof in an amount equivalent to about 1 mg to about 160 mg oxycodone HCl; and
    naloxone or a pharmaceutically acceptable salt thereof in an amount equivalent to about 0.5 mg to about 80 mg naloxone HCl; wherein the oxycodone or pharmaceutically acceptable salt thereof and the naloxone or pharmaceutically acceptable salt thereof are the only pharmaceutically active agents comprised in said dosage form.

2. The method according to claim 1, wherein the patient exhibits intestinal dysbiosis or increased risk for intestinal bacterial translocation that is induced by the diverticulitis not by an opioid agonist.

3. The method according to claim 1, wherein said pain is moderate to severe pain.

4. The method according to claim 1, wherein the method excludes co-administration of
    an active agent directed to improvement of intestinal dysbiosis or to decreasing risk for intestinal bacterial translocation; or
    an active agent directed to improvement of opioid-induced constipation or opioid-induced bowel dysfunction.

5. The method according to claim 1, wherein the dosage form comprises oxycodone or a pharmaceutically acceptable salt thereof and naloxone or a pharmaceutically acceptable salt thereof in a 2:1 ratio by weight.

6. The method according to claim 1, wherein the dosage form is a prolonged release dosage form.

7. The method according to claim 6, wherein the dosage form comprises a prolonged release matrix.

8. The method according to claim 7, wherein the matrix comprises a fatty alcohol or a hydrophobic polymer.

9. The method according to claim 6, wherein the dosage form comprises a prolonged release coating.

10. The method according to claim 1, wherein the dosage form is selected from a tablet, a capsule, a multi-particulate, a dragée, a granulate, and a powder.

11. The method according to claim 7, wherein the matrix comprises an alkylcellulose.

12. The method according to claim 7, wherein the matrix comprises ethylcellulose.

13. A method for the treatment of pain in a patient suffering from pain and diverticulitis, comprising administering to said patient a prolonged release oral pharmaceutical dosage form comprising:
    oxycodone or a pharmaceutically acceptable salt thereof in an amount equivalent to about 1 mg to about 160 mg oxycodone HCl; and
    naloxone or a pharmaceutically acceptable salt thereof in an amount equivalent to about 0.5 mg to about 80 mg naloxone HCl;
    wherein the dosage form comprises the oxycodone or pharmaceutically acceptable salt thereof and the naloxone or pharmaceutically acceptable salt thereof in a 2:1 ratio by weight; and wherein the oxycodone or pharmaceutically acceptable salt thereof and the naloxone or pharmaceutically acceptable salt thereof are the only pharmaceutically active agents comprised in said dosage form.

14. The method according to claim 13, wherein the dosage form comprises:
    oxycodone or a pharmaceutically acceptable salt thereof in an amount equivalent to about 1 mg to about 80 mg oxycodone HCl; and
    naloxone or a pharmaceutically acceptable salt thereof in an amount equivalent to about 0.5 mg to about 40 mg naloxone HCl.

15. The method according to claim 13, wherein the dosage form comprises:
    oxycodone or a pharmaceutically acceptable salt thereof in an amount equivalent to about 2.5 mg oxycodone HCl; and
    naloxone or a pharmaceutically acceptable salt thereof in an amount equivalent to about 1.25 mg naloxone HCl.

16. The method according to claim 13, wherein the dosage form comprises:
    oxycodone or a pharmaceutically acceptable salt thereof in an amount equivalent to about 5 mg oxycodone HCl; and
    naloxone or a pharmaceutically acceptable salt thereof in an amount equivalent to about 2.5 mg naloxone HCl.

17. The method according to claim 13, wherein the dosage form comprises:
    oxycodone or a pharmaceutically acceptable salt thereof in an amount equivalent to about 10 mg oxycodone HCl; and
    naloxone or a pharmaceutically acceptable salt thereof in an amount equivalent to about 5 mg naloxone HCl.

18. The method according to claim 13, wherein the dosage form comprises:
    oxycodone or a pharmaceutically acceptable salt thereof in an amount equivalent to about 20 mg oxycodone HCl; and
    naloxone or a pharmaceutically acceptable salt thereof in an amount equivalent to about 10 mg naloxone HCl.

19. The method according to claim 13, wherein the dosage form comprises:
    oxycodone or a pharmaceutically acceptable salt thereof in an amount equivalent to about 40 mg oxycodone HCl; and
    naloxone or a pharmaceutically acceptable salt thereof in an amount equivalent to about 20 mg naloxone HCl.

20. The method according to claim 13, wherein the dosage form comprises:
    oxycodone or a pharmaceutically acceptable salt thereof in an amount equivalent to about 80 mg oxycodone HCl; and
    naloxone or a pharmaceutically acceptable salt thereof in an amount equivalent to about 40 mg naloxone HCl.

21. The method according to claim 13, wherein the dosage form comprises:
    oxycodone or a pharmaceutically acceptable salt thereof in an amount equivalent to about 160 mg oxycodone HCl; and
    naloxone or a pharmaceutically acceptable salt thereof in an amount equivalent to about 80 mg naloxone HCl.

* * * * *